(12) United States Patent
Kimura et al.

(10) Patent No.: US 8,325,318 B2
(45) Date of Patent: Dec. 4, 2012

(54) INFORMATION STORAGE/READOUT DEVICE FOR USE IN CONTINUOUSLY MANUFACTURING SYSTEM FOR LIQUID-CRYSTAL DISPLAY ELEMENTS, AND METHOD AND SYSTEM FOR PRODUCING THE SAME

(75) Inventors: Kouji Kimura, Ibaraki (JP); Kazuo Kitada, Ibaraki (JP); Tomokazu Yura, Ibaraki (JP); Satoru Koshio, Ibaraki (JP); Fumihito Shimanoe, Ibaraki (JP); Takuya Nakazono, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 13/230,470

(22) Filed: Sep. 12, 2011

(65) Prior Publication Data

US 2012/0002154 A1    Jan. 5, 2012

Related U.S. Application Data

(62) Division of application No. 12/903,977, filed on Oct. 13, 2010.

(30) Foreign Application Priority Data

Oct. 13, 2009    (JP) ................... 2009-236089

(51) Int. Cl.
*G02F 1/13* (2006.01)
*G02F 1/1335* (2006.01)

(52) U.S. Cl. ............... 349/187; 349/96; 359/437

(58) Field of Classification Search .......... 349/96, 349/187; 359/437
See application file for complete search history.

(56) References Cited

U.S. PATENT DOCUMENTS

| 7,163,599 B2 | 1/2007 | Nagata et al. |
| 2004/0095526 A1 | 5/2004 | Yamabuchi et al. |
| 2004/0169809 A1 | 9/2004 | Yamabuchi et al. |
| 2005/0199337 A1 | 9/2005 | Nishikubo et al. |

(Continued)

FOREIGN PATENT DOCUMENTS

EP    2267516    12/2010

(Continued)

OTHER PUBLICATIONS

Korean Notice of Allowance for application No. 10-2010-0052547, citing the above reference(s).

(Continued)

*Primary Examiner* — Lauren Nguyen
(74) *Attorney, Agent, or Firm* — Lowe Hauptman Ham & Berner, LLP

(57) ABSTRACT

An information storage/readout device for use in a system for continuously manufacturing liquid-crystal display elements comprises an information storage medium which stores therein slitting position information created based on the position of a defect detected by an inspection of a continuous polarizing composite film included in a continuous optical film laminate including a continuous polarizing composite film formed with an adhesive layer and a continuous carrier film releasably laminated on the adhesive layer, to indicate defective-polarizing-sheet slitting positions defining a defective or defect-containing polarizing sheet, and normal-polarizing-sheet slitting positions defining a normal or defect-free polarizing sheet, in the continuous inspected optical film laminate, and a roll of the continuous inspected optical film laminate which is provided with an identification indicia. In continuous manufacturing of liquid-crystal display elements, the present invention can dramatically enhance product accuracy and manufacturing speed and drastically improve product yield.

8 Claims, 23 Drawing Sheets

U.S. PATENT DOCUMENTS

| | | | |
|---|---|---|---|
| 2007/0013858 A1 | 1/2007 | Yamabuchi et al. | |
| 2009/0159175 A1* | 6/2009 | Nakahira et al. | 156/64 |
| 2009/0199950 A1* | 8/2009 | Kitada et al. | 156/64 |
| 2010/0165333 A1 | 7/2010 | Ohashi et al. | |

FOREIGN PATENT DOCUMENTS

| | | |
|---|---|---|
| JP | 57-52017 | 3/1982 |
| JP | 57-052017 | 3/1982 |
| JP | 11-095028 | 4/1999 |
| JP | 2002-023151 | 1/2002 |
| JP | 2003-161935 | 6/2003 |
| JP | 2003-202298 | 7/2003 |
| JP | 2003-344302 | 12/2003 |
| JP | 2004-144913 | 5/2004 |
| JP | 2004-361741 | 12/2004 |
| JP | 2005-32165 | 2/2005 |
| JP | 2005-62165 | 3/2005 |
| JP | 2005-062165 | 3/2005 |
| JP | 2005-114624 | 4/2005 |
| JP | 2005-298208 | 10/2005 |
| JP | 2006-058411 | 3/2006 |
| JP | 2007-064989 | 3/2007 |
| JP | 2007-140046 | 6/2007 |
| JP | 2009-061498 | 3/2009 |
| JP | 2009-069142 | 4/2009 |
| KR | 20030042760 | 6/2003 |
| TW | 200502649 | 1/2005 |
| TW | 200634358 | 10/2006 |
| WO | 2007/058023 | 5/2007 |
| WO | 2009/123002 | 10/2009 |
| WO | 2009/128115 | 10/2009 |

OTHER PUBLICATIONS

European Search Report for EP10186867, citing the above reference(s).

Taiwanese office action for 099129092, citing the above reference(s).

* cited by examiner

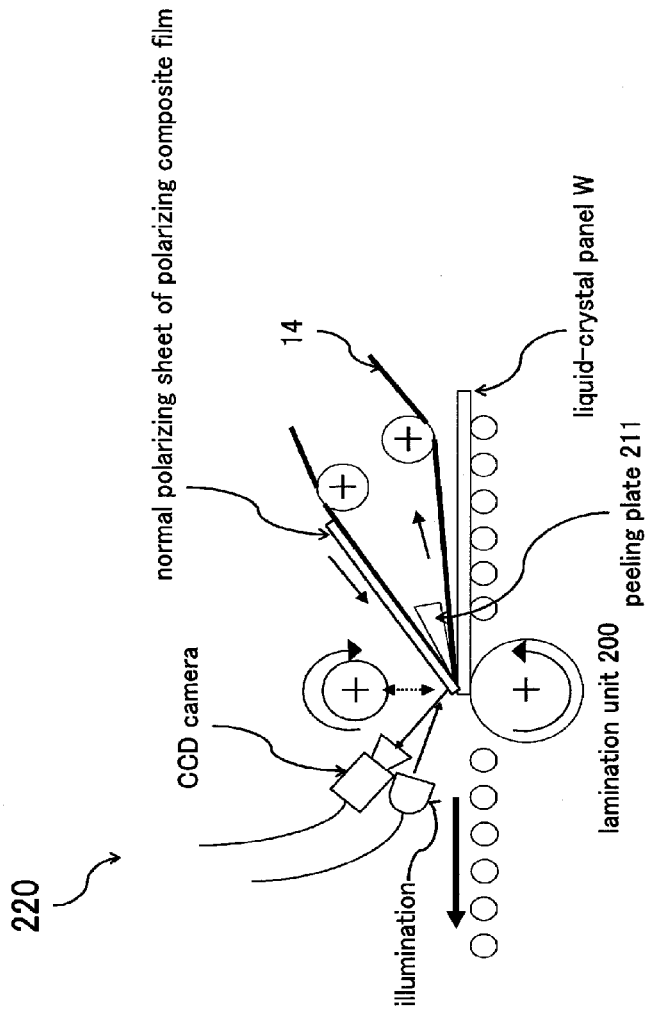

FIG.15 types of identification indicia

| No | type | | type of information | data contents | effectiveness |
|---|---|---|---|---|---|
| 1 | one dimensional code<br>example: | 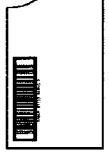 | alphameric characters | LOT No<br>No | ○ |
| 2 | two dimensional code<br>example: |  | alphameric characters<br>kana (Japanese syllabary)<br>kanji (Chinese character) | LOT No<br>No<br>distance | ○ |
| 3 | IC tag<br>example: |  | alphameric characters<br>kana (Japanese syllabary)<br>kanji (Chinese character) | LOT No<br>No<br>distance | ○ |
| 4 | label | 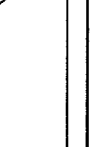 | existence or nonexistence determination | starting point | △ |
| 5 | hole |  | existence or nonexistence determination | starting point | △ |

FIG.20

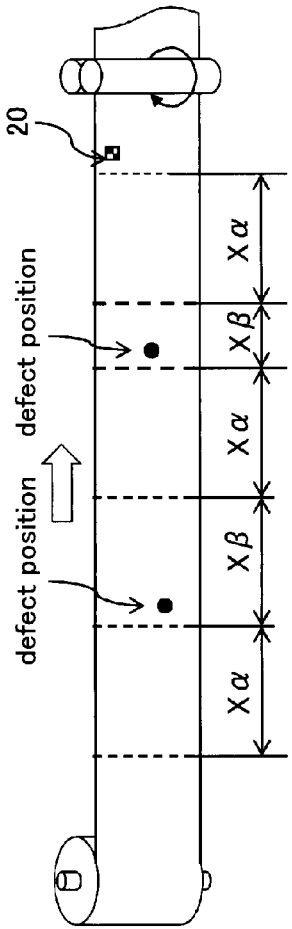

example of defect position information examples of information in information storage medium

| lot number | slitting position | identification information Xγ | determination |
|---|---|---|---|
| #A0001 | 0 | — | — |
| | 220 | 1 | Xβ |
| | 400 | 0 | Xα |
| | 400 | 1 | Xβ |
| | 400 | 0 | Xα |

Xα = size of product
Xβ = defective polarizing sheet $(X' + X_0)$
Xγ = identification information of defective polarizing sheet examples of recording identification indicia to inspected optical film laminate

Data Code

20 → 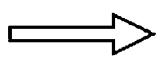 = #A0001 } production LOT

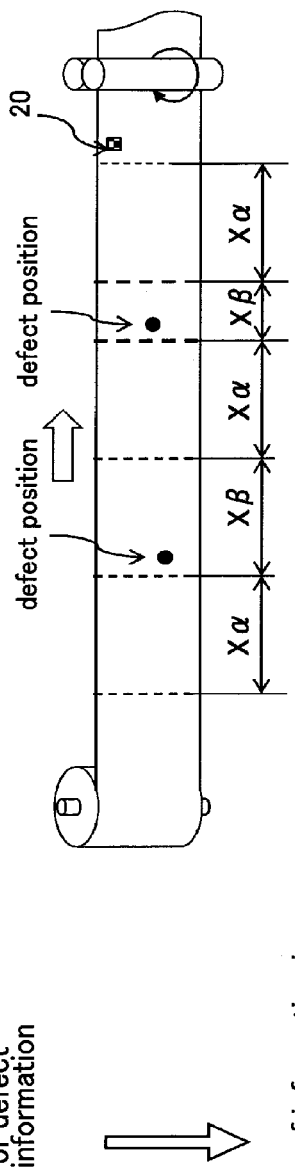

FIG.21 example of defect position information

⇩ examples of information in information storage medium

| lot number | slitting position (serve as identification information) | determination |
|---|---|---|
| #A0001 | 0 | — |
| | 220 | $X\beta$ |
| | 400 | $X\alpha$ |
| | 405 | $X\beta$ |
| | 400 | $X\alpha$ |

$X\alpha$ = size of product $X\beta$ = defective polarizing sheet $(X'+X_0)$ $(X' \leq X\alpha)$ ※ when $X\beta$ $(X'+X_0) = X\alpha$, $X\beta = X' + X_0'$ $(X_0 < X_0') > X\alpha$ (in the table on left, $X_0' = X_0 + 5mm$)

⇩ examples of recording identification indicia to inspected optical film laminate

20 ⟶ Data Code = #A0001 } production LOT

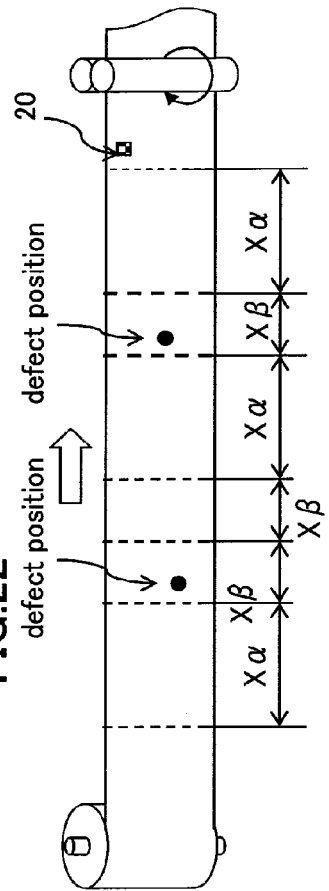

FIG.22 example of defect position information

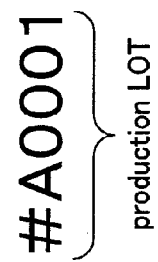

examples of information in information storage medium

| lot number | slitting position (serve as identification information) | determination |
|---|---|---|
| #A0001 | 0 | – |
|  | 220 | $X\beta$ |
|  | 400 | $X\alpha$ |
|  | 200 | $X\beta$ |
|  | 200 | $X\beta$ |
|  | 400 | $X\alpha$ |

$X\alpha$ = size of product
$X\beta$ = defective polarizing sheet ($X' \leqq X\alpha$)
※when $X\beta$ ($X'+X_0$) = $X\alpha$,
$X\beta$ = ($X' + X_0$)/m < $X\alpha$
(in the table on left,
when m=2, $X\beta$ = 400 / 2 = 200)

examples of recording identification indicia to inspected optical film laminate

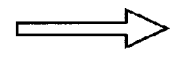 = #A0001 production LOT

FIG.23

| inspection unit | types of defect | | | | |
| --- | --- | --- | --- | --- | --- |
| | internal foreign substances | internal pores | bright spots | surface irregularities | flaw/undulation |
| reflection | △ | △ | × | ○ | ○ |
| transmission | ○ | ○ | △ | △ | × |
| Cross-Nichol transmission | ○ | ○ | ○ | × | ○ |

INFORMATION STORAGE/READOUT DEVICE FOR USE IN CONTINUOUSLY MANUFACTURING SYSTEM FOR LIQUID-CRYSTAL DISPLAY ELEMENTS, AND METHOD AND SYSTEM FOR PRODUCING THE SAME

CROSS-REFERENCE TO RELATED APPLICATIONS

The present application is a Divisional Application of U.S. patent application Ser. No. 12/903,977, filed Oct. 13, 2010, which claims priority to Japanese patent application number 2009-236089, filed on Oct. 13, 2009, which is incorporated by reference in its entirety.

TECHNICAL FIELD

The present invention relates to an information storage/readout device for use in a continuous manufacturing system for liquid-crystal display elements, wherein the continuous manufacturing system is configured to work with a roll of a continuous optical film laminate which comprises a continuous polarizing composite film including an adhesive layer and having a width conforming to a long or short side of a liquid-crystal panel formed in a given size, and a continuous carrier film releasably laminated on the adhesive layer, the system being operative to form a plurality of slits in the continuous optical film laminate fed out from the roll, along a direction perpendicular to a longitudinal direction thereof, to allow a plurality of polarizing sheets each having a given length corresponding to the long or short side of the liquid-crystal panel to be sequentially cut from the continuous optical film laminate and laminated to respective ones of a plurality of liquid-crystal panels so as to continuously manufacture liquid-crystal display elements. More specifically, the present invention relates to an information storage/readout device for use in the continuous manufacturing system for liquid-crystal display elements, wherein the information storage/readout device comprises an information storage medium which stores therein slitting position information created based on the position of a defect detected by an inspection of a continuous polarizing composite film included in a continuous optical film laminate to indicate a defective-polarizing-sheet slitting position defining a defective or defect-containing polarizing sheet, and a normal-polarizing-sheet slitting position defining a normal or defect-free polarizing sheet, and a roll of the continuous inspected optical film laminate which is provided with an identification means or indicia. The present invention is further related to a method and system for producing the information storage/readout device.

BACKGROUND ART

Taking a widescreen television having a diagonal screen size of 42 inches as an example, a liquid-crystal panel W therefor comprises a layered liquid-crystal panel which includes a pair of rectangular-shaped glass substrates each having a size of about 540 to 560 mm in length× about 950 to 970 mm in width× about 0.7 mm (700 μm) in thickness, and a liquid-crystal layer having a thickness of about 5 μm provided with a transparent electrode, a color filter etc., and sandwiched between the glass substrates, as shown in FIG. 1. The thickness of the liquid-crystal panel W itself is about 1.4 mm (1400 μm). The liquid-crystal display element is typically manufactured by laminating a polarizing composite film sheet 11" including a polarizer and a protective film to each of the front (viewing side) and back (backlight side) sides thereof. The polarizing composite film sheet 11" is formed, for example, to have a dimension shown in FIG. 1 from a polarizing composite film 11 which is provided in the form of a flexible optical film laminate 10 having a laminate structure.

For a liquid-crystal display element to function, the direction of orientation of liquid-crystal molecules and the direction of polarization of the polarizer are closely related each other. In liquid-crystal display element technologies, LCDs (Liquid-crystal Display) using a TN (Twisted Nematic) type liquid-crystal have first been put into practical use, and then LCDs using a VA (vertical Alignment) type liquid-crystal, an IPS (In-plane Switching) type liquid-crystal etc., have been put into practical use. Although a detailed technical explanation is omitted, in an LCD using such TN-type liquid-crystal panel, liquid-crystal molecules are provided between two upper and lower orientation films having respective rubbing directions on the inner surfaces of glass substrates of the liquid-crystal panel. This means that the liquid-crystal molecules are twisted by 90 degrees along the optical axis, so that when a voltage is applied, the liquid-crystal molecules are aligned in a direction perpendicular to the orientation of films. However, in the case where the LCD is designed to allow images as seen from right and left sides of a display screen as those view directly in front of the display screen, the direction of rubbing on the orientation film at the viewing-side must be 45 degrees (the rubbing direction of the other orientation film is 135 degrees). It is therefore necessary that sheets of the polarizing composite films to be laminated respectively on the front and back sides of the liquid-crystal panel must have polarizers respectively oriented in directions inclined by 45 degrees with respect to a lengthwise or widthwise direction of the display screen so as to conform to the rubbing directions.

Therefore, it is required that the optical film laminate is punched out or cut into a rectangular-shaped sheet having a long or short side determined in accordance with the size of the TN liquid-crystal panel, in such a manner that the long or short side inclined by 45 degrees with respect to the orientation direction of the polarizer. This procedure is described in Japanese Laid-Open Patent Publication JP 2003-161935A (Patent Document 1) or Japanese Patent 3616866 B (Patent Document 2), for example. The sheet of such rectangular shape has a width or a short side dimension which is smaller than the width of the optical film laminate. The rectangular-shaped sheets punched out or cut from the optical film laminate may be collectively referred as "individualized sheets."

In producing a liquid-crystal display element using such individualized sheets, each of the individualized sheets is punched out or cut in advance together with a separator adhered to an adhesive layer. The shaped individualized sheets are stored in a magazine in a liquid-crystal display element production system. The individualized sheets stored in the magazine are taken out and conveyed one-by-one by means of a suction conveyance unit to the lamination position for lamination with respective ones of the liquid-crystal panels W. Before being laminated to the liquid-crystal panel W, the separator releasably laminated to a formed adhesive layer is peeled from respective ones of the individualized sheets, and each of the individualized sheets is laminated to the liquid-crystal panel W via as such exposed adhesive layer. As the individualized sheets are flexible, they tend to be bowed or warped on their edges, and thus it is a serious technical impediment in lamination with liquid-crystal panels. Thus, in producing a liquid-crystal display element using individualized sheets, it has been required to adopt individualized sheets having four trimmed sides and a certain level of stiffness for less deflection or bend and which can be conveyed and laminated easily, to facilitate peeling respective ones of separators one-by-one and an accurate and swift positioning and laminating respective ones of the individualized sheets with liquid-crystal panels. For this reason, the individualized sheets have been laminated with a protective film, for example, of 40 to 80 μm thick not only to one surface but also to both surfaces of the polarizer to have stiffness induced by the thickness. During the initial period in the history of the manufacturing process of the liquid-crystal display elements, the optical film sheet or a polarizing sheet comprised in such optical film sheet was generally known as "polarizing plate" which is still used as a common name.

In the manufacturing process of TN-type liquid-crystal display elements, it is impossible to obtain finished liquid-crystal display elements simply by sequentially laminating the sheets formed in the sequential punching or cutting process to respective ones of a plurality of liquid-crystal panels in a subsequent process. This is because the sheet of the optical film laminate is cut from the web in such a manner that the sheet has a long or short side extending in a direction 45 degrees with respect to the orientation direction of the polarizer which is the longitudinal or stretching direction of the polarizer base film (i.e., with respect to the feed direction of the optical film laminate prior to the punching or cutting process), so that the sheet cannot be laminated to respective ones of the liquid-crystal panels with the orientation as it has been cut from the web. Therefore, to laminate the sheets to the liquid-crystal panel, each of the sheets need to be punched-out at an angled direction of 45 degrees from the continuous web of the optical film laminate having a width greater than a long side of the liquid-crystal panel with respect to the lengthwise direction of the optical film laminate, using, for example, a die wider than a long side of the liquid-crystal panel, and fed to the lamination station where the polarizing sheets are laminated with the liquid-crystal panels, as seen in the Patent Document 1 or 2. Alternatively, the continuous optical film laminate in use needs to be an elongated optical film laminate preliminarily punched or cut from the continuous web of the optical film laminate having a substantially large width in a direction 45 degrees inclined with respect to the lengthwise direction, or an elongated optical film laminate formed with a plurality of formed sheets connected into a continuous film configuration. At any rate, the above methods do not provide any noticeable improvement over the method of using individualized sheets.

The Patent Document 3 is the Japanese Patent Publication No. 62-14810B which discloses, prior to the VA-type liquid-crystal and the IPS-type liquid-crystal being brought into practical use, an apparatus to produce a liquid-crystal panel element. The apparatus is considered to be a type of labeler unit which produces an LCD using the TN-type liquid-crystal. There is taught to provide an optical film laminate in the form of an elongated continuous optical film laminate having substantially large width and slit it in a direction 45 degrees oblique to the stretching direction of the polarizing composite film with a width corresponding to the width of the liquid-crystal panel. Alternatively, a film-like elongated optical film laminate sheet may be formed by longitudinally connecting a plurality of optical film laminate sheets. Therefore, the method taught by the Patent Document 3 cannot be applied directly to a manufacturing process adapted to perform steps of continuously providing a plurality of polarizing composite film sheets from a continuous optical film laminate and laminating the respective sheets to respective ones of the liquid-crystal panels comprising VA-type or IPS-type liquid-crystal.

Automation of manufacturing process for liquid-crystal display elements using individualized sheets is disclosed, for example, in the Japanese Laid-Open Patent Publication JP 2002-23151A (Patent Document 4). Flexible individualized sheets tend to be bowed or warped due to curves or distortion of their edges, and thus it is a serious technical impediment to accuracy and speed in registration and lamination with liquid-crystal panels. Thus, it will be understood that the individualized sheet is required to have a certain level of thickness and stiffness to facilitate registration and lamination with liquid-crystal panels typically in transportation under suction. For example, the disclosures in the Japanese Laid-Open Patent Publication JP 2004-144913A (Patent Document 5), Japanese Laid-Open Patent Publication JP 2005-298208A (Patent Document 6) or Japanese Laid-Open Patent Publication JP 2006-58411A (Patent Document 7) disclose measures for addressing such technical problems.

In contrast to TN-type liquid-crystal panels, the VA-type and IPS-type liquid-crystal panels are not designed to arrange liquid-crystal molecules in twisted orientations. Thus, in the case of the liquid-crystal display element using these types of liquid-crystal panels, there is no need to have the polarization axis of the polarizing sheet oriented at 45 degrees in view of viewing angle characteristics inherent to the orientation of the liquid-crystal. Each of these liquid-crystal display elements using these liquid-crystal panels is formed by applying polarizing sheets to the opposite sides of the liquid-crystal display panel oriented with their polarization axes crossed at 90 degrees crossing angle. In the case of the VA-type and IPS-type liquid-crystal panels, with respect to the technical view point of symmetry of the viewing angle characteristics and visibility, maximum contrast can be obtained along the direction of the polarizing axis of the polarizing sheet, so that it is preferable that the sheets have polarizing axes oriented in parallel with the longitudinal or transverse direction of the liquid-crystal panel. Thus, it will be understood that these sheets to be applied to the liquid-crystal panel has a feature that the continuous optical film laminate including a polarizing composite film which has been subjected to a longitudinal or transverse stretching can be continuously fed out from a roll and cut along transverse lines with respect to the feed direction of the continuous optical film laminate to sequentially produce rectangular polarizing sheets having the same width as the optical film laminate width.

Because of the improved viewing angle characteristics, for liquid-crystal used in a display element for widescreen televisions, the VA-type liquid-crystal or the IPS-type liquid-crystal are more widely adopted than the TN type. In view of such trend in environments of technical developments, proposals to enhance the manufacturing efficiency using these types of liquid-crystal panels have been made such as the one described in Japanese Laid-Open Patent Publication JP 2004-361741A (Patent Document 8). This patent discloses steps of continuously feeding a continuous optical film laminate, cutting the continuous optical film laminate in conformity with the size of a liquid-crystal panel and sequentially laminating a plurality of optical film sheets which have been produced by the cutting step to respective ones of a plurality of the liquid-crystal panels.

However, the mainstream of manufacture of liquid-crystal display elements is still based on the manufacturing technology utilizing individualized sheets, due to the following technical problems. In manufacturing liquid-crystal display elements, a critical technical challenge is to detect any defect which may otherwise be retained in the display elements to be formed, and to prevent any defective product from being produced. Most of the product defects primarily arise from defects in the polarizing composite film contained in the continuous optical film laminate. However, it is not practical to provide the continuous optical film laminate after completely removing all defects contained in individual films which are to be laminated together to form the optical film laminate, because it is extremely difficult to produce a defect-free continuous optical film laminate under existing circumstances. To maintain quality of display elements, it is not permitted to use a polarizing composite film sheet having visible flaws or defects for a sheet for television display element even if such a flaw or defect is small. Given that the long side dimension of a polarizing sheet formed from the polarizing composite film is about 1 m, if a defective region cannot be preliminarily removed, 20 to 200 defective liquid-crystal display elements out of 1,000 products will be produced.

Proposals relating to preliminary inspection apparatus for a polarizing composite film have previously been made, as disclosed, for example, in Japanese Patent No. 3974400B (Patent Document 9), Japanese Laid-Open Patent Publications JP 2005-62165A (Patent Document 10) and JP 2007-64989A (Patent Document 11) for improving the production efficiency of manufacturing the individualized sheets. These proposals have disclosed technical means essential to improving yield in the manufacture of such individualized sheets.

Further, Japanese Laid-Open Patent Publications JP 2007-140046A (Patent Document 12) discloses a method comprising the steps of exposing a polarizing composite film having an adhesive layer by peeling a carrier film included in the continuous optical film laminate continuously fed out from a roll of continuous optical film laminate, detecting a defect or defects present in the polarizing composite film, punching only normal regions of the polarizing composite film in rectangular shape, appropriately avoiding defective regions, and conveying the punched normal polarizing sheets to the lamination position for lamination with the liquid-crystal panels by other conveying medium. It should however be noted that this process is not the one which makes it possible to feed the normal optical film sheets formed from a continuous optical film laminate to the lamination position for lamination with the liquid-crystal panel by means of the carrier film. This technique is a method for once laminating the cut individualized sheets to other conveying medium before conveying to the lamination position with the liquid-crystal panels, so this technique is not beyond the individualized sheet manufacturing system of liquid-crystal display element.

Japanese Laid-Open Patent Publications JP 2009-061498A (Patent Document 13) discloses a method for laminating the sheets of the optical film laminate with the liquid-crystal panels and an apparatus therefor. This invention contains an innovative proposal allowing for shifting from a liquid-crystal display element manufacturing system designed to carry a plurality of preliminary formed individualized sheets in the manufacturing process of the liquid-crystal display element, and laminate the individualized sheets one by one to respective ones of a plurality of liquid-crystal panels, to a continuous manufacturing system for liquid-crystal display element designed to continuously form a plurality of optical film sheets and directly laminate the formed sheets to respective ones of a plurality of liquid-crystal panels.

However, the method and system disclosed cause not only substantial complexity in the entire system for laminating but also an increase in the number of steps and difficulty in control for each step, and thus causes reduction in the manufacturing speed.

The present invention has been made in view of the aforementioned problems in the prior proposals and through intensive researches and considerations for enabling a continuous manufacturing of liquid-crystal display elements, provides a method and system for significantly enhancing product accuracy and manufacturing speed, and drastically improving manufacturing yield, in the manufacture of liquid-crystal display elements.

The prior art documents referred to in the above descriptions are listed below.
Patent Document 1: Japanese Laid-Open Patent Publication JP 2003-161935A
Patent Document 2: Japanese Patent No. 3616866B
Patent Document 3: Japanese Patent Publication 62-14810B
Patent Document 4: Japanese Laid-Open Patent Publication JP 2002-23151A
Patent Document 5: Japanese Laid-Open Patent Publication JP 2004-144913A
Patent Document 6: Japanese Laid-Open Patent Publication JP 2005-298208A
Patent Document 7: Japanese Laid-Open Patent Publication JP 2006-58411A
Patent Document 8: Japanese Laid-Open Patent Publication JP 2004-361741A
Patent Document 9: Japanese Patent No. 3974400B
Patent Document 10: Japanese Laid-Open Patent Publication JP 2005-62165A
Patent Document 11: Japanese Laid-Open Patent Publication JP 2007-64989A
Patent Document 12: Japanese Laid-Open Patent Publication JP 2007-140046A
Patent Document 13: Japanese Laid-Open Patent Publication JP 2009-061498A

DISCLOSURE OF THE INVENTION

Problem to be Solved by the Invention

The VA-type and IPS-type liquid-crystal panels are advantageous over TN-type liquid-crystal panels from the viewpoint of manufacture in that there is no restriction in the VA and IPS-types that two polarizing sheets are required to be laminated to respective ones of front and rear surfaces of the liquid-crystal panel in 45 degrees oblique with respect to the polarization axis of the polarizing sheet on the respective sides of the liquid-crystal display element, as experienced in the manufacture of TN-type liquid-crystal panels, due to the viewing angle characteristics inherent to the orientation of the liquid-crystal. Therefore, it is possible to carry out a process for continuously manufacturing liquid-crystal display elements using the VA-type and IPS-type liquid-crystal panels, while feeding a continuous optical film laminate, by continuously laminating the polarizing composite film sheets prepared by cutting the optical film laminate in the transverse direction with respect to the feed direction of the optical film laminate with the respective ones of a plurality of the liquid-crystal panels. In addition, during the feed of the optical film laminate, if normal polarizing sheets having no defect and defective or defect-containing polarizing sheets having defects detected through the preliminary inspection of a continuous polarizing composite film are being cut out, and if only the normal polarizing sheets are laminated to respective ones of a plurality of liquid-crystal panels to make liquid-crystal display elements, without interrupting the feed of the optical film laminate, it becomes possible to obtain enhanced product accuracy and manufacturing speed as well as significantly improved production yield in the manufacture of liquid-crystal display elements.

It is an object of the present invention to provide means for subjecting to a preliminary inspection, a continuous optical film laminate comprising a continuous polarizing composite film with an adhesive layer, and a continuous carrier film releasably laminated on the adhesive layer, to inspect the continuous polarizing sheet (the continuous optical film laminate subjected to the preliminary inspection will hereinafter be referred to as "continuous inspected optical film laminate), in such a manner as to allow a defective polarizing sheet containing a defect detected by the preliminary inspection, and a defect-free, normal polarizing sheet, to be continuously cut from the continuous inspected optical film laminate being fed toward a lamination station, and preventing the defective polarizing sheet from being laminated to a liquid-crystal panel, whereby means for continuously laminating only a plurality of the normal polarizing sheets to respective ones of a plurality of the liquid-crystal panels without interrupting the feeding of the continuous inspected optical film laminate is achieved to dramatically enhance product accuracy and manufacturing speed and drastically improve product yield, in a continuous manufacturing process for liquid-crystal display elements.

Means for Solving the Problem

The above object can be achieved by providing an information storage medium which stores therein slitting position information created based on a position of a defect detected by preliminarily inspecting a continuous polarizing composite film included in a continuous optical film laminate to indicate defective-polarizing-sheet slitting positions defining a defective or defect-containing polarizing sheet, and normal-polarizing-sheet slitting positions defining a normal or defect-free polarizing sheet, in a continuous inspected optical film laminate, and a roll of the continuous inspected optical film laminate which is provided with an identification means or indicia, in such a manner as to allow a plurality of the normal polarizing sheets to be cut from the continuous inspected optical film laminate being fed out from the roll, based on the slitting position information read out from the information storage medium in accordance with reading of the identification means or indicia from the continuous inspected optical film laminate, and laminated to respective ones of a plurality of liquid-crystal panels.

In one aspect of the present invention, there is provided an information storage/readout device for use in a continuous manufacturing system for liquid-crystal display elements, wherein the continuous manufacturing system is provided with a roll of a continuous optical film laminate which comprises a continuous polarizing composite film including an adhesive layer and having a width conforming to a long or short side of a liquid-crystal panel formed in a given size, and a continuous carrier film releasably laminated on the adhesive layer, and designed to form a plurality of slits in the continuous optical film laminate fed out from the roll, along a direction perpendicular to a longitudinal direction thereof, to allow a plurality of polarizing sheets each having a given length corresponding to the long or short side of the liquid-crystal panel to be sequentially cut from the continuous optical film laminate and laminated to respective ones of a plurality of the liquid-crystal panels so as to continuously manufacture liquid-crystal display elements. The information storage/readout device comprises an information storage medium which stores therein slitting position information created based on a position of a defect detected by an inspection of a continuous polarizing composite film included in a continuous optical film laminate to indicate defective-polarizing-sheet slitting positions defining a defective or defect-containing polarizing sheet, and normal-polarizing-sheet slitting positions defining a normal or defect-free polarizing sheet, in the continuous inspected optical film laminate, and a roll of the continuous inspected optical film laminate which is provided with an identification means or indicia, wherein the continuous manufacturing system is operable, based on the slitting position information read out from the information storage medium in accordance with reading of the identification means or indicia from the continuous inspected optical film laminate, and distance measurement data obtained from a feed distance of the continuous inspected optical film laminate from the roll, to form a plurality of slits in the continuous inspected optical film laminate from a surface opposite to the continuous carrier film to a depth reaching a surface of the continuous carrier film adjacent to the adhesive layer, to allow a plurality of the normal polarizing sheets each having a length corresponding to the long or short side of the liquid-crystal panel to be cut from the continuous inspected optical film laminate, and laminated to respective ones of a plurality of the liquid-crystal panels.

In one embodiment of the present invention, the continuous inspected optical film laminate further comprises a continuous surface protection film releasably laminated on the continuous polarizing composite film at a surface opposite to the adhesive layer.

According to another aspect of the present invention, there is provided a method for producing an information to be stored in a storage/readout device for use in a continuous manufacturing system for liquid-crystal display elements, wherein the continuous manufacturing system is provided with a roll of a continuous optical film laminate which comprises a continuous polarizing composite film including an adhesive layer and having a width conforming to a long or short side of a liquid-crystal panel formed in a given size, and a continuous carrier film releasably laminated on the adhesive layer, and designed to form a plurality of slits in the continuous optical film laminate fed out from the roll, along a direction perpendicular to a longitudinal direction thereof, to allow a plurality of polarizing sheets each having a given length corresponding to the long or short side of the liquid-crystal panel to be sequentially cut from the continuous optical film laminate and laminated to respective ones of a plurality of the liquid-crystal panels so as to continuously manufacture liquid-crystal display elements, and the information storage/readout device comprises an information storage medium which stores therein slitting position information created based on a position of a defect detected by an inspection of a continuous polarizing composite film included in a continuous optical film laminate to indicate a defective-polarizing-sheet slitting position defining a defective or defect-containing polarizing sheet, and a normal-polarizing-sheet slitting position defining a normal or defect-free polarizing sheet, in the continuous inspected optical film laminate; and a roll of the continuous inspected optical film laminate which is provided with an identification means or indicia. The method comprises the steps of laminating a continuous protective film on at least one of opposite surfaces of a continuous polarizer to form a continuous polarizing composite film on which the adhesive layer is not yet formed, inspecting the continuous polarizing composite film on which the adhesive layer is not yet formed to detect any defect contained in the continuous polarizing composite film on which the adhesive layer is not yet formed, creating, based on the position of the defect in the continuous polarizing composite film on which the adhesive layer is not yet formed, the slitting position information indicative of the normal polarizing sheet-slitting positions and the defective polarizing sheet-slitting positions defining respectively the normal polarizing sheet and the defective polarizing sheet in a direction perpendicular to the longitudinal direction of the continuous polarizing composite film, releasably laminating a continuous carrier film to the continuous inspected polarizing composite film through an adhesive layer to form the continuous inspected optical film laminate, storing the slitting position information in a storage medium, in a manner usable by the continuous manufacturing system to, during feeding of the continuous inspected optical film laminate, form a plurality of slits in the continuous inspected optical film laminate along a direction perpendicular to the longitudinal direction from a surface opposite to the continuous carrier film to a depth reaching a surface of the continuous carrier film adjacent to the adhesive layer so as to make it possible to cut the normal polarizing sheet and the defective polarizing composite film from the continuous inspected optical film laminate individually, creating the identification means or indicia in association with the slitting position information and providing the identification means or indicia on the continuous inspected optical film laminate, and winding the continuous inspected optical film laminate provided with the identification means or indicia, into a roll to provide the roll of the continuous optical film laminate In one embodiment of the present invention, the step of forming the continuous inspected optical film laminate includes a sub-step of releasably laminating a continuous surface protection film on the continuous inspected polarizing composite film at a surface opposite to the adhesive layer.

In another embodiment of the present invention, the step of detecting a defect contained in the continuous polarizing composite film includes one or a combination of sub-steps of primarily inspecting a surface of the continuous polarizing composite film on which the adhesive layer is not yet formed by means of reflected light, transmitting light irradiated from a light source through the continuous polarizing composite film on which the adhesive layer is not yet formed to detect any defect existing in the continuous polarizing composite film on which the adhesive layer is not yet formed as a shade, and arranging the continuous polarizing composite film and a polarization filter to have absorption axes thereof to be set in a cross-Nicol arrangement, projecting light from a light source thereto, and observing light transmitted therethrough to detect any defect in the continuous polarizing composite film as a bright spot.

According to still further aspect of the present invention, there is provided a method for producing an information storage/readout device for use in a continuous manufacturing system for liquid-crystal display elements, wherein the continuous manufacturing system is configured to work with a roll of a continuous optical film laminate which comprises a continuous polarizing composite film formed with an adhesive layer and having a width conforming to a long or short side of a liquid-crystal panel formed in a given size, and a continuous carrier film releasably laminated on the adhesive layer, and operate to form a plurality of slits in the continuous optical film laminate fed out from the roll, along a direction perpendicular to a longitudinal direction thereof, to allow a plurality of polarizing sheets each having a given length corresponding to the long or short side of the liquid-crystal panel to be sequentially cut from the continuous optical film laminate and laminated to respective ones of a plurality of liquid-crystal panels so as to continuously manufacture liquid-crystal display elements, and wherein the information storage/readout device comprises an information storage medium which stores therein slitting position information created based on the position of a defect detected by an inspection of a continuous polarizing composite film included in a continuous optical film laminate to indicate defective-polarizing-sheet slitting positions defining a defective or defect-containing polarizing sheet, and normal-polarizing-sheet slitting positions defining a normal or defect-free polarizing sheet, in the continuous inspected optical film laminate, and a roll of the continuous inspected optical film laminate which is provided with an identification means or indicia. The method comprises the steps of preparing a roll of a continuous provisional optical film laminate which comprises a continuous polarizing composite film formed with an adhesive layer, and a continuous provisional carrier film releasably laminated on the adhesive layer, peeling the continuous provisional carrier film while feeding the continuous provisional optical film laminate out from the roll, to expose the continuous polarizing composite film including adhesive layer, inspecting a surface and inside of the continuous polarizing composite film including exposed adhesive layer to detect any defect contained in the continuous polarizing composite film including adhesive layer, creating based on the position of the defect in the continuous polarizing composite film including adhesive layer, the slitting position information indicative of the normal polarizing sheet-slitting positions and the defective polarizing sheet-slitting positions defining respectively the normal polarizing sheet and the defective polarizing sheet in a direction perpendicular to a longitudinal direction of the continuous polarizing composite film including adhesive layer, releasably laminating a continuous carrier film on the exposed adhesive layer of the continuous inspected polarizing composite film to form the continuous inspected optical film laminate, storing the slitting position information in the information storage medium, in a manner usable by the continuous manufacturing system to, during feeding of the continuous inspected optical film laminate, form a plurality of slits in the continuous inspected optical film laminate along a direction perpendicular to the longitudinal direction from a surface opposite to the continuous carrier film to a depth reaching a surface of the continuous carrier film adjacent to the adhesive layer so as to make it possible to cut the normal polarizing sheet and the defective polarizing composite film from the continuous inspected optical film laminate individually, creating the identification means or indicia in association with the slitting position information and providing the identification means or indicia on the continuous inspected optical film laminate, and winding the continuous inspected optical film laminate provided with the identification means or indicia, into a roll to provide the roll of the continuous optical film laminate.

In one embodiment of the present invention, the continuous provisional carrier film has a transferable adhesive layer formed by subjecting one surface of the continuous provisional carrier film to a releasing treatment, applying a solvent containing an adhesive to the treated surface, and drying the solvent.

In another embodiment of the present invention, the surface of the continuous carrier film laminated on the exposed adhesive layer of the continuous inspected polarizing composite film is preliminarily subjected to a releasing treatment.

In yet another embodiment of the present invention, the step of forming the continuous inspected optical film laminate includes a sub-step of releasably laminating a continuous surface protection film on the continuous inspected polarizing composite film at a surface opposite to the adhesive layer.

In accordance with still another embodiment of the present invention, the step of detecting a defect contained in the continuous polarizing composite film includes one or a combination of sub-steps of primarily inspecting a surface of the continuous polarizing composite film including adhesive layer by means of reflected light, a sub-step of transmitting light irradiated from a light source through the continuous polarizing composite film with an adhesive layer provided thereon to detect a defect contained in the continuous polarizing composite film as a shade, and arranging the continuous polarizing composite film and a polarization filter to have absorption axes thereof to be set in a cross-Nicol arrangement, projecting light from a light source thereto, and observing light transmitted therethrough to detect any defect contained in the continuous polarizing composite film as a bright spot.

According to still further aspect of the present invention, there is provided a system for producing an information storage/readout device for use in a continuous manufacturing system for liquid-crystal display elements, wherein the continuous manufacturing system is configured to work with a roll of a continuous optical film laminate which comprises a continuous polarizing composite film having an adhesive layer provided on one surface thereof and having a width conforming to a long or short side of a liquid-crystal panel formed in a given size, and a continuous carrier film releasably laminated on the adhesive layer, and operates to form a plurality of slits in the continuous optical film laminate fed out from the roll, along a direction perpendicular to a longitudinal direction thereof, to make ti possible to sequentially cut a plurality of polarizing sheets each having a given length corresponding to the long or short side of the liquid-crystal panel from the continuous optical film laminate and to laminate to respective ones of a plurality of the liquid-crystal panels so as to continuously manufacture liquid-crystal display elements, and wherein the information storage/readout device comprises an information storage medium which stores therein slitting position information created based on the position of a defect detected by an inspection of a continuous polarizing composite film included in a continuous optical film laminate to indicate defective-polarizing-sheet slitting positions defining a defective or defect-containing polarizing sheet, and normal-polarizing-sheet slitting positions defining a normal or defect-free polarizing sheet, in the continuous inspected optical film laminate, and a roll of the continuous inspected optical film laminate which is provided with an identification means or indicia. The system comprises a polarizing composite film-forming unit adapted to laminate a continuous protective film on at least one of opposite surfaces of a continuous polarizer to form an continuous polarizing composite film on which the adhesive layer is not yet formed, an inspection unit adapted to inspect the continuous polarizing composite film on which the adhesive layer is not yet formed to detect any defect contained in the continuous polarizing composite film on which the adhesive layer is not yet formed, slitting position information-creating means adapted to, based on the position of the defect in the continuous polarizing composite film on which the adhesive layer is not yet formed, create the slitting position information indicative of the normal polarizing sheet-slitting positions and the defective polarizing sheet-slitting positions defining respective ones of the normal polarizing sheet and the defective polarizing sheet in a direction perpendicular to a longitudinal direction of the continuous polarizing composite film on which the adhesive layer is not yet formed, a continuous inspected optical film laminate forming unit adapted to releasably laminate a continuous carrier film to the continuous inspected polarizing composite film through an adhesive layer to form the continuous inspected optical film laminate, an information storage medium forming unit adapted to store the slitting position information in the information storage medium, in a manner usable by the continuous manufacturing system to, during feeding of the continuous inspected optical film laminate, form a plurality of slits in the continuous inspected optical film laminate along a direction perpendicular to the longitudinal direction from a surface opposite to the continuous carrier film to a depth reaching a surface of the continuous carrier film adjacent to the adhesive layer so as to make it possible to cut the normal polarizing sheet and the defective polarizing sheet from the continuous inspected optical film laminate individually, an identification providing unit adapted to create the identification means or indicia in association with the slitting position information and provide the identification means or indicia on the continuous inspected optical film laminate, a taking up unit adapted to wind the continuous inspected optical film laminate having the identification means or indicia, into a roll to form the roll of the continuous optical film laminate; and a control unit adapted control respective operations of at least the polarizing composite film forming unit, the inspection unit, the slitting position information creating means, the continuous inspected optical film laminate forming unit, the information storage medium forming unit, the identification providing unit and the taking up unit, in an inter-related manner.

In one embodiment of the present invention, the continuous inspected optical film laminate forming unit includes a surface protection film feed device adapted to releasably laminate a continuous surface protection film on the continuous inspected polarizing composite film at a surface opposite to the adhesive layer.

In another embodiment of the present invention, the inspection unit includes one or a combination of a first inspection device adapted to primarily inspect a surface of the continuous polarizing composite film on which the adhesive layer is not yet formed by means of reflected light, a second inspection device adapted to transmit light irradiated from a light source through the continuous polarizing composite film on which the adhesive layer is not yet formed to detect a defect contained in the continuous polarizing composite film as a shade, and a third inspection device adapted to arrange the continuous polarizing composite film on which the adhesive layer is not yet formed and a polarization filter to have absorption axes thereof to be set in a cross-Nicol arrangement, emitting light from a light source thereto, and observing light transmitted therethrough to detect a defect contained in the continuous polarizing composite film as a bright spot.

According to still further aspect of the present invention, there is provided a system for producing an information storage/readout device for use in a continuous manufacturing system for liquid-crystal display elements, wherein the continuous manufacturing system is configured to work with a roll of a continuous optical film laminate which comprises a continuous polarizing composite film having an adhesive layer provided on one surface thereof and having a width conforming to a long or short side of a liquid-crystal panel formed in a given size, and a continuous carrier film releasably laminated on the adhesive layer, and operate to form a plurality of slits in the continuous optical film laminate fed out from the roll, along a direction perpendicular to a longitudinal direction thereof, to make it possible to be sequentially cut a plurality of polarizing sheets each having a given length corresponding to the long or short side of the liquid-crystal panel from the continuous optical film laminate and laminate to respective ones of a plurality of the liquid-crystal panels so as to continuously manufacture liquid-crystal display elements, and wherein the information storage/readout device comprises an information storage medium which stores therein slitting position information created based on the position of a defect detected by an inspection of a continuous polarizing composite film included in a continuous optical film laminate to indicate defective-polarizing-sheet slitting positions defining a defective or defect-containing polarizing sheet, and normal-polarizing-sheet slitting positions defining a normal or defect-free polarizing sheet, in the continuous inspected optical film laminate, and a roll of the continuous inspected optical film laminate which is provided with an identification means or indicia. The system comprises a provisional optical film laminate feed unit provided with a roll of a continuous provisional optical film laminate which comprises a continuous polarizing composite film having an adhesive layer provided on one surface thereof, and a continuous provisional carrier film releasably laminated on the adhesive layer, and adapted to feed the continuous provisional optical film laminate out from the roll, a provisional carrier film peeling unit adapted to peel the continuous provisional carrier film from the continuous provisional optical film laminate being fed out from the roll, to have the adhesive layer on the continuous polarizing composite film exposed, an inspection unit adapted to inspect a surface and inside of the continuous polarizing composite film having the exposed adhesive layer to detect a defect contained in the continuous polarizing composite film including adhesive layer, slitting position information creating means adapted to, based on the position of the defect in the continuous polarizing composite film including adhesive layer, create the slitting position information indicative of the normal polarizing sheet-slitting positions and the defective polarizing sheet-slitting positions defining respective ones of the normal polarizing sheet and the defective polarizing sheet in a direction perpendicular to a longitudinal direction of the continuous polarizing composite film including the adhesive layer, a continuous inspected optical film laminate forming unit adapted to releasably laminate a continuous carrier film on the exposed adhesive layer of the continuous polarizing composite film to form the continuous inspected optical film laminate, an information storage medium forming unit adapted to store the slitting position information in the information storage medium, in a manner usable by the continuous manufacturing system to, during feeding of the continuous inspected optical film laminate, form a plurality of slits in the continuous inspected optical film laminate along a direction perpendicular to the longitudinal direction from a surface opposite to the continuous carrier film to a depth reaching a surface of the continuous carrier film adjacent to the adhesive layer so as to make it possible to cut the normal polarizing sheet and the defective polarizing sheet from the continuous inspected optical film laminate individually, an identification providing unit adapted to create the identification means or indicia in association with the slitting position information and provide the identification means or indicia on the continuous inspected optical film laminate, a taking up unit adapted to wind the continuous inspected optical film laminate provided with the identification means or indicia, into a roll to provide the roll of the continuous optical film laminate, and a control unit adapted control respective operations of at least the provisional optical film laminate feed unit, the provisional carrier film peeling unit, the inspection apparatus, the slitting position information creating means, the continuous inspected optical film laminate forming unit, the information storage medium forming unit, the identification providing unit and the taking up unit, in an inter-related manner.

In one embodiment of the present invention, the continuous provisional carrier film has a transferable adhesive layer formed by subjecting one surface of the provisional carrier film to a releasing treatment, applying a solvent containing an adhesive to the treated surface, and drying the solvent.

In another embodiment of the present invention, the continuous carrier film is subjected to a releasing treatment at a surface laminated on the exposed adhesive layer of the continuous inspected polarizing composite film In yet another embodiment of the present invention, the continuous inspected optical film laminate-forming unit includes a surface protection film feed device adapted to releasably laminate a continuous surface protection film on a surface of the continuous inspected polarizing composite film on an opposite side of the adhesive layer.

In still another embodiment of the present invention, the inspection unit includes one or any combination of a first inspection device adapted to primarily inspect a surface of the continuous polarizing composite film having an adhesive layer provided on one surface thereof by means of reflected light, a second inspection device adapted to transmit light irradiated from a light source through the continuous polarizing composite film having such adhesive layer to detect a defect contained in the continuous polarizing composite film as a shade, and a third inspection device adapted to arrange the continuous polarizing composite film having such adhesive layer and a polarization filter to have absorption axes thereof to be set in a cross-Nicol arrangement, emitting light from a light source thereto, and observing light transmitted therethrough to detect any defect contained in the continuous polarizing composite film as a bright spot.

BRIEF DESCRIPTION OF THE DRAWING

FIG. 14 is a schematic diagram showing a lamination unit which comprises a edge detection unit for detecting a leading edge of a normal polarizing sheet cut from the continuous inspected optical film laminate illustrated in FIG. 13 into a given length corresponding to that of a liquid-crystal panel, and straight ahead posture detection unit for detecting an alignment between a straight ahead posture of the normal polarizing sheet and a feed direction.

FIG. 15 is a table showing a type, contents, etc., of identification means or indicia to be provided on the continuous inspected optical film laminate.

FIG. 20 illustrates one example of the slitting position information, corresponding to a technique of storing defective polarizing sheet identification information $X\gamma$ in FIG. 17.

FIG. 21 illustrated one example of the slitting position information, corresponding to a technique of setting a distance to a next slitting position to $((x'+x_0))$, wherein $(x'>x_0)$, in FIG. 18.

FIG. 22 illustrates one example of the slitting position information, corresponding to a technique of setting a distance to a next slitting position to $[(x'+x_0)/m]$, wherein $m=\pm 2$ or more, in FIG. 19.

FIG. 23 is a table showing a defect inspection device, a type of defect and a defect detection method.

DESCRIPTION OF EMBODIMENTS

In the context of the description, a continuous film comprising a continuous polarizer laminated with a continuous protective film on one or each surface and formed with an adhesive layer on the surface to be laminated with a liquid-crystal panel is referred as "a continuous polarizing composite film," and a sheet having a rectangular shape and formed from the continuous polarizing composite film is referred as "a polarizing composite film sheet" or simply "a sheet," rather than the commonly called name "polarizing plate." In addition, when a sheet is formed from a continuous polarizing composite film having a continuous surface-protection film and a continuous carrier film attached thereto, and when this sheet has to be distinguished from "a polarizing composite film sheet", it is referred as "an optical film laminate sheet", and a sheet formed from the continuous surface-protection film or the continuous carrier film included in the continuous polarizing composite film is respectively referred as "a surface-protection film sheet" or "a carrier film sheet" respectively.

The present invention will now be described with reference to specific embodiments illustrated in the accompanying drawings.

Figure 4:
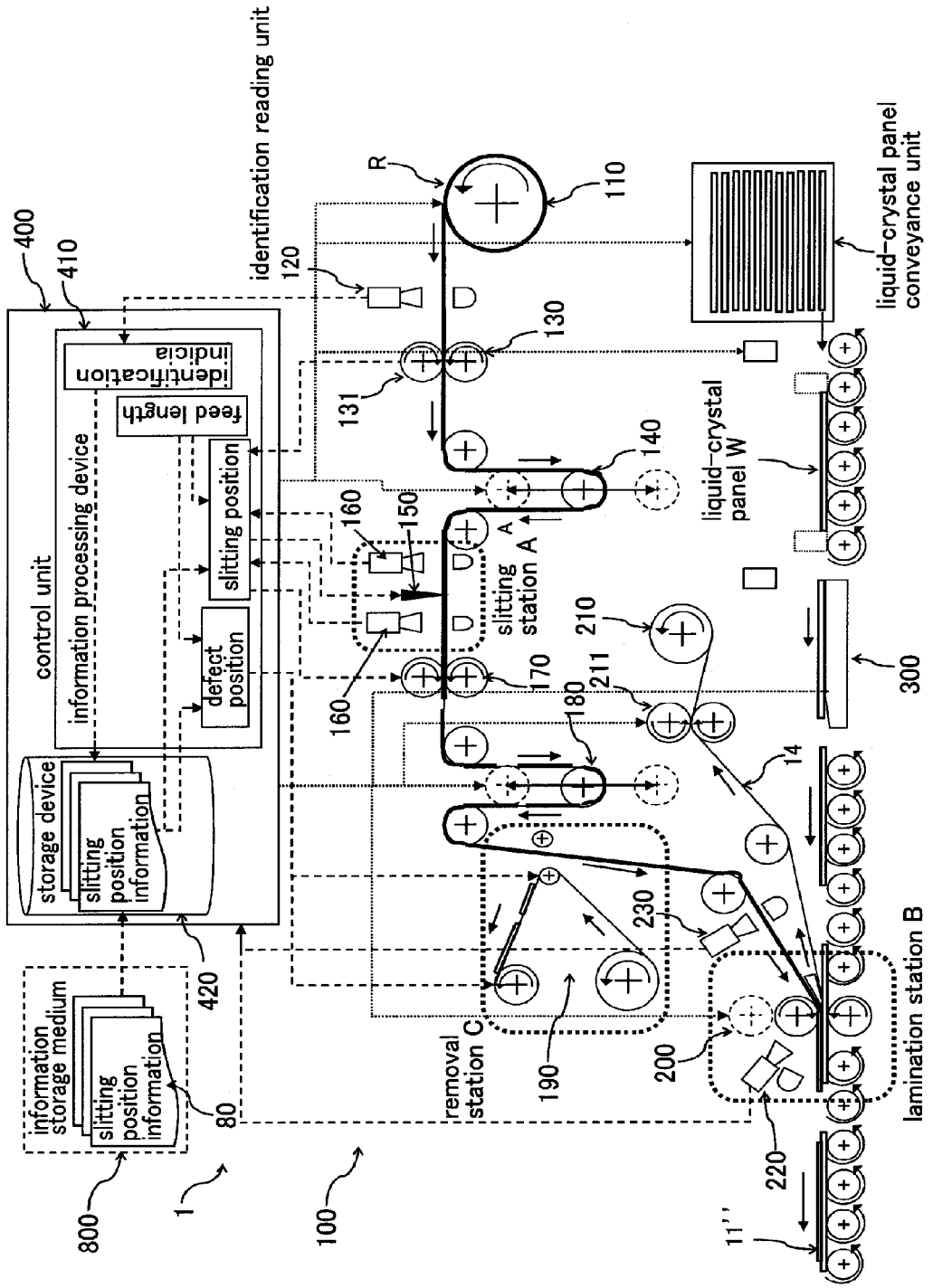
FIG. 4 is a conceptual diagram showing a continuous manufacturing system for liquid-crystal display element 1, in one embodiment of the present invention, wherein the system 1 comprises an optical film laminate feed unit 100 for feeding a continuous inspected optical film laminate from a roll R thereof provided therein, and a liquid-crystal panel conveyance unit 300 for conveying a liquid-crystal panel to be laminated with a normal polarizing sheet cut from the continuous inspected optical film laminate by forming slits in the continuous inspected optical film laminate based on slitting position information read out from an information storage medium.

1. Configuration of a System for Continuous Manufacturing Liquid-Crystal Display Elements FIG. 4 is a schematic diagram showing a system for continuous manufacturing liquid-crystal display element. The system 1 is provided with a roll R of a continuous inspected optical film laminate which comprises a continuous polarizing composite film having an adhesive layer provided on one surface thereof and having a width conforming to a long or short side of a liquid-crystal panel, and a continuous carrier film releasably laminated on the adhesive layer, wherein the continuous inspected optical film laminate is provided with an identification means or indicia 20 associated with slitting position information 80 which is created based on the position of a defect detected by an inspection of a continuous polarizing composite film before the adhesive layer is applied thereto or a continuous polarizing composite film having an adhesive layer provided on one surface thereof, and pre-stored in an information storage medium 800. The system 1 comprises an optical film laminate feed unit 100 for continuously feeding the continuous inspected optical film laminate from the roll R. The information storage medium 800 stores therein the slitting position information 80 which is created during a process of producing the continuous inspected optical film laminate provided with the identification means or indicia 20, based on a position of a defect detected by an inspection of a continuous polarizing composite film without the adhesive layer or a continuous polarizing composite film formed with the adhesive layer to indicate defective-polarizing-sheet slitting positions defining a defective or defect-containing polarizing sheet, and normal-polarizing-sheet slitting positions defining a normal or defect-free polarizing sheet, in the continuous inspected optical film laminate, as will be described later. The information storage medium 800 may be comprised of a flexible disk, a CD, a DVD, a flash memory or a hard disk. The slitting position information 80 created based on the position of a defect detected by an inspection of a continuous polarizing composite film may be transferred to a storage device 420 of the system 1 directly via the Internet or a dedicated line, without involving the information storage medium 800, just after the slitting position information 80 is created in a production system for the roll R which will be described later. In this case, the storage device 420 functions as "information storage medium" set forth in the appended claims. The system 1 further comprises a liquid-crystal panel conveyance unit 300 for sequentially conveying a plurality of liquid-crystal panels to be laminated with respective ones of a plurality of a normal polarizing sheets cut from the continuous inspected optical film laminate into a given length corresponding to a long or short side of the liquid-crystal panel by forming a plurality of slits in the continuous inspected optical film laminate based on the slitting position information 80 read out from the information storage medium 800 or the storage device 420. The system 1 further comprises a control unit 400 for generally controlling operations of the optical film laminate feed unit 100 and the liquid-crystal panel conveyance unit 300.

The optical film laminate feed unit 100 has a slitting station A for cutting a plurality of polarizing sheets 11" from the continuous inspected optical film laminate, a removal station C for removing one or more of the defective polarizing sheets 11", and a lamination station B for laminating normal ones of the cut polarizing sheets 11" to respective ones of a plurality of liquid-crystal panels. The optical film laminate feed unit 100 may have the removal station C and the lamination station B in an overlapped arrangement, as will be described later. The liquid-crystal panel conveyance unit 300 will be described later. The control unit 400 has a function of reading out the slitting position information 80 from the information storage medium 800 in accordance with reading of the identification means or indicia 20 by an identification means reading unit 120 which will be described later, and storing the readout information in the storage device 420.

Figure 5:
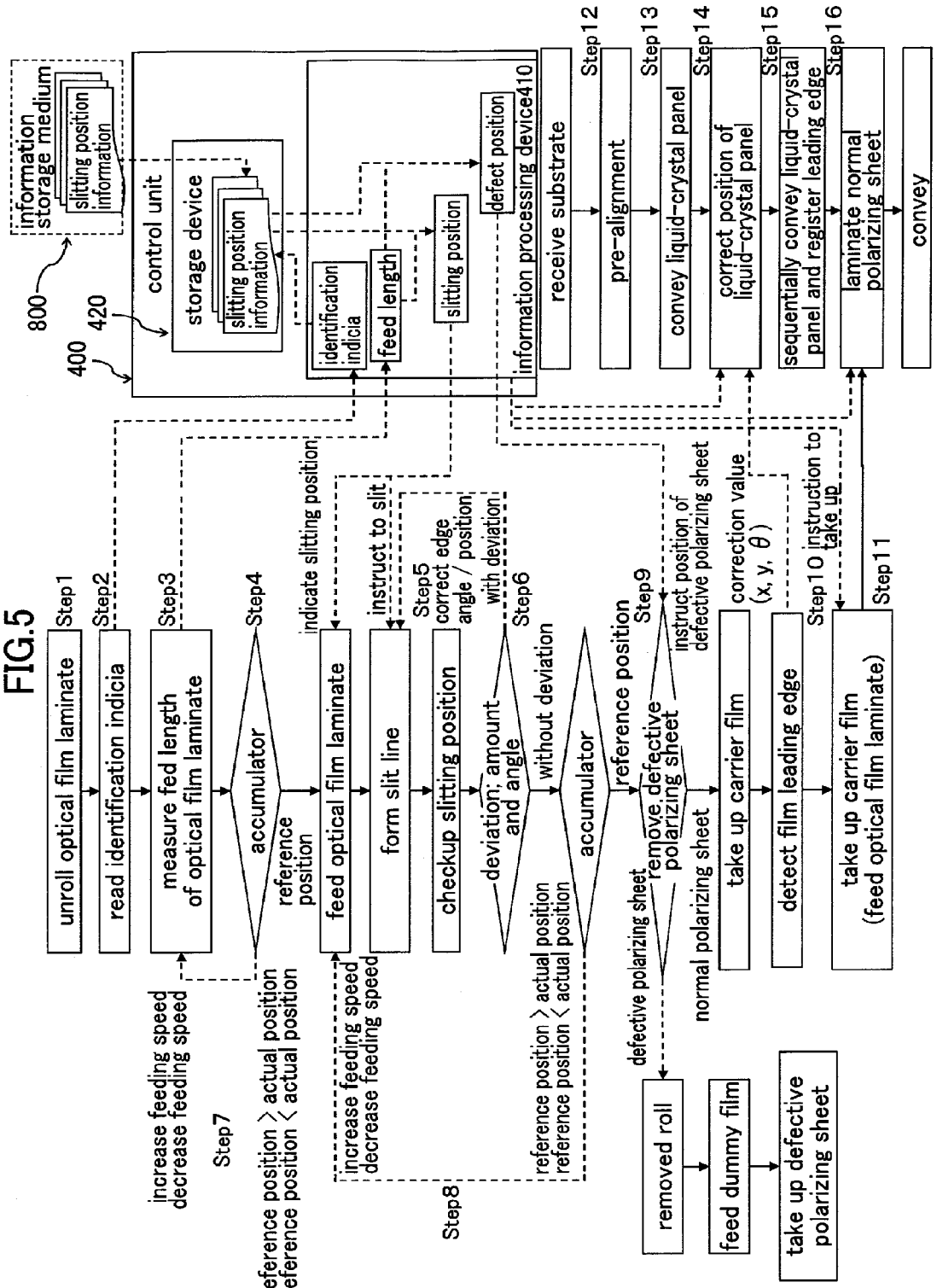
FIG. 5 is a flowchart showing a manufacturing process or process steps in the continuous manufacturing system illustrated in FIG. 4.

The optical film laminate feed unit 100 comprises a support rack 110 adapted to be provided with the roll R of the continuous inspected optical film laminate in a rotatable manner, an identification means reading unit 120 adapted to read the identification means or indicia 20, a first film feed unit 130 including a pair of feed rollers which incorporate an encoder 131 adapted to measure a feed distance of the continuous inspected optical film laminate, a first speed adjustment unit 140 including a dancer roller adapted to feed the continuous inspected optical film laminate at a constant speed, a slitting unit 150 provided in the slitting station A to form a plurality of slits in the continuous inspected optical film laminate along a direction perpendicular to a feed direction of the continuous inspected optical film laminate, based on distance measurement data obtained from the feed distance of the continuous inspected optical film measured by the encoder 131 and the slitting position information 80 read out from the information storage medium 800 or the storage device 420, a slitting position checkup unit 160 adapted to check a position of each of the slits formed in the slitting station A, a second film feed unit 170 including a pair of feed rollers; a second speed adjustment unit 180 including a dancer roller adapted to feed the continuous inspected optical film laminate at a constant speed, a defective polarizing sheet removal unit 190 adapted, based on an instruction from the control unit 400, to recognize the defective polarizing sheets and remove the defective polarizing sheets from the continuous carrier film; a lamination unit 200 provided in the lamination station B and including a pair of lamination rollers adapted to peel the normal polarizing sheets each cut into a give length corresponding to that of the liquid-crystal panel, from the continuous carrier film, and then laminate the normal polarizing sheets to respective ones of the liquid-crystal panels, a carrier film take up drive mechanism 210 adapted to take up the continuous carrier film, an edge detection unit 220 provided in the lamination station B to detect the leading edge of each of the normal polarizing sheet, and a position or straight-ahead-posture detection unit 230 adapted to detect a position or straight-ahead posture of each of the normal polarizing sheets. Details of the liquid-crystal panel conveyance unit 300 will be described later, based on FIG. 13. FIG. 5 is a flowchart showing a manufacturing process performed by the above components of the system 1.

2. Production of Roll R of Continuous Inspected Optical Film Laminate (Structure of Continuous Inspected Optical Film Laminate)

Figure 2:
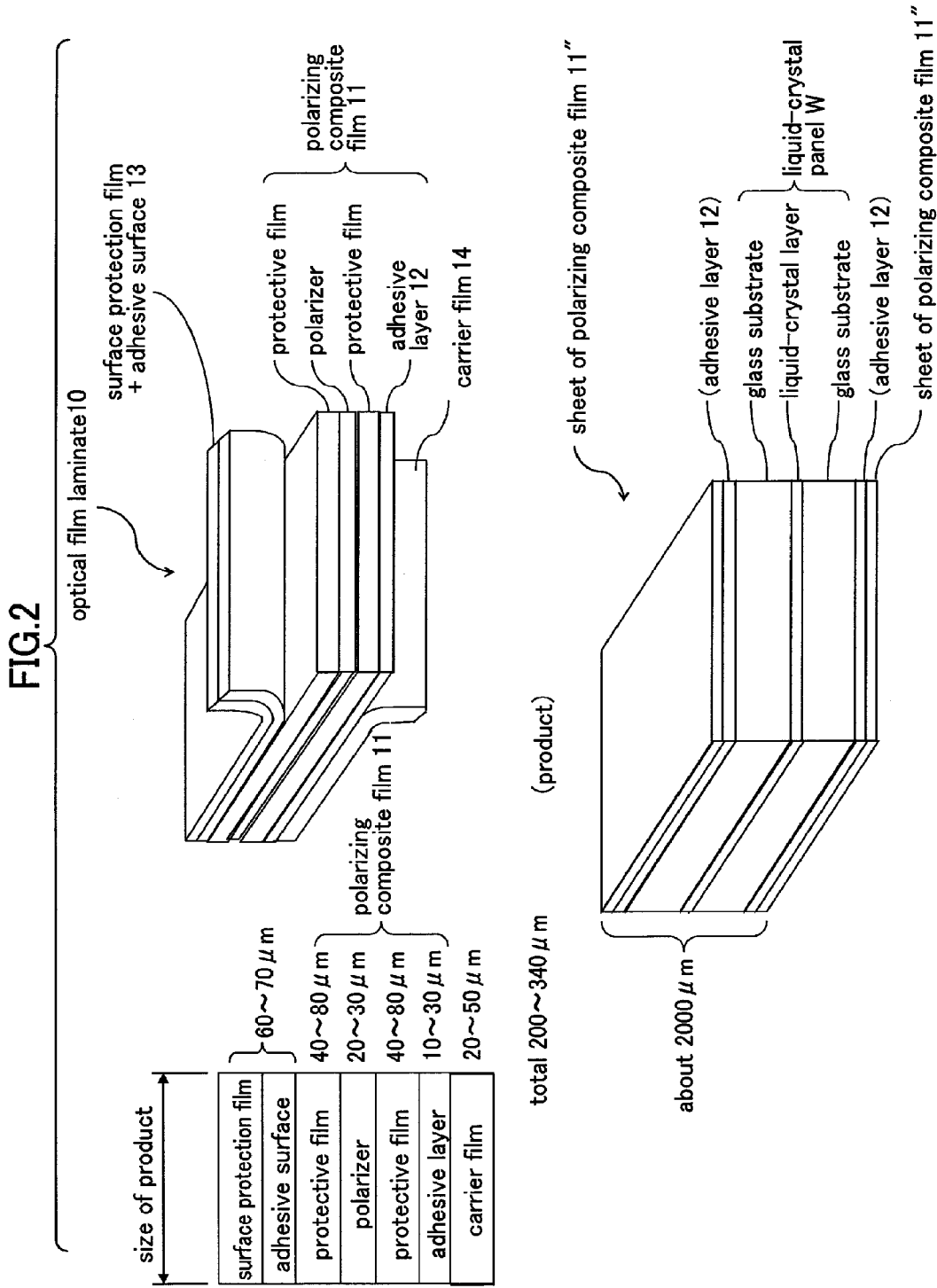
FIG. 2 is a schematic diagram showing a structure of a continuous optical film laminate for use in manufacturing of liquid-crystal display elements, in the present invention.
Figure 3:
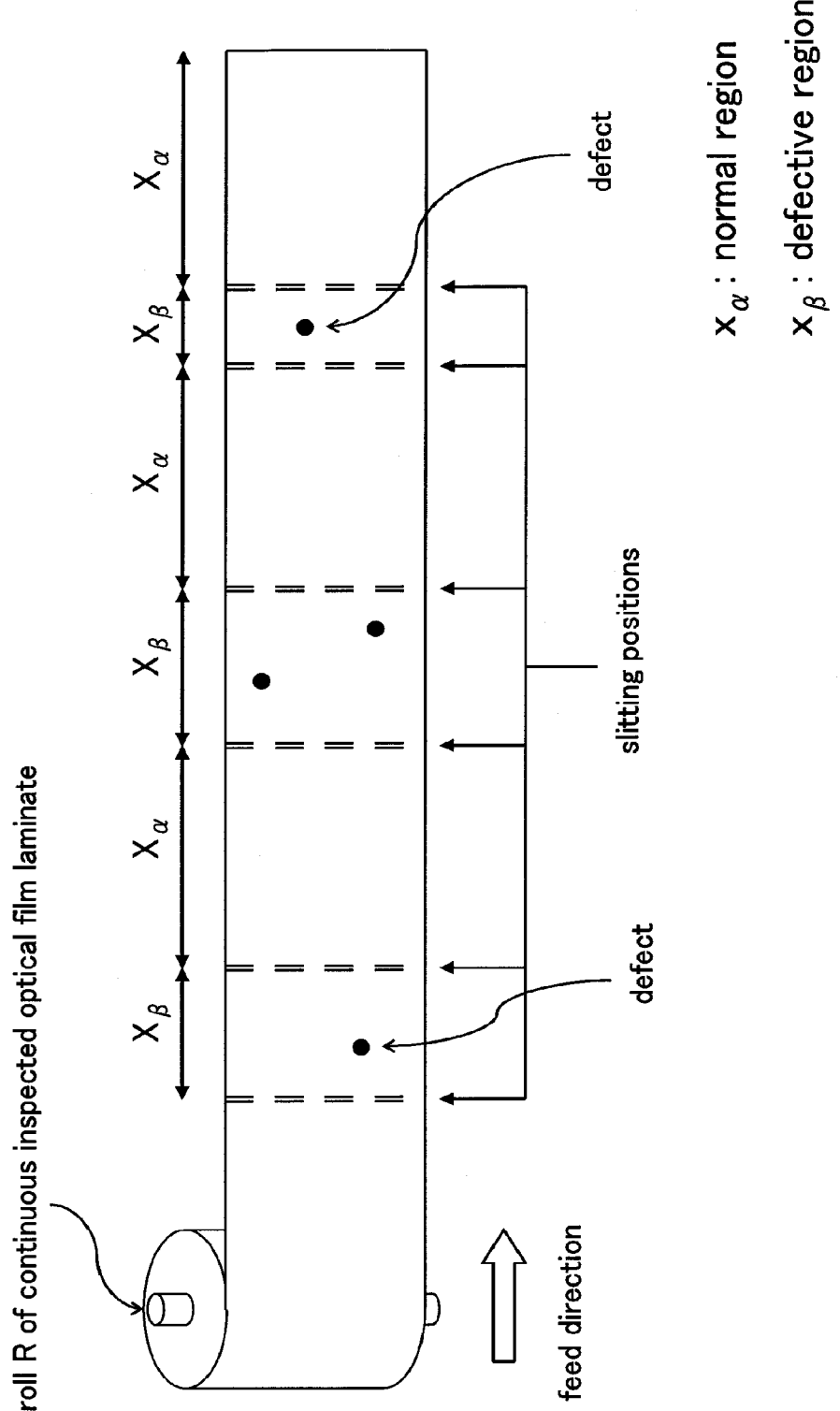
FIG. 3 is a schematic diagram showing a defect-free, normal region (corresponding to a normal-polarizing-sheet slitting position defining a normal polarizing sheet) and a defective region (corresponding to a defective-polarizing-sheet slitting position defining a defective polarizing sheet) containing a defect contained in a continuous polarizing composite film included in a continuous inspected optical film laminate for use in manufacturing of liquid-crystal display elements in the present invention.

The roll R loaded in the support rack 110 of the optical film laminate feed unit 100 is formed by winding a flexible, continuous inspected optical film laminate 10 which comprises a continuous polarizing composite film 11 including a continuous polarizer having a continuous protective film laminated on at least one of opposite surfaces thereof, and an adhesive layer 12 applied to one side of the continuous polarizer to be laminated to a liquid-crystal panel, a continuous surface protection film 13 having an adhesive surface laminated on the continuous polarizing composite film 11 at a surface opposite to the adhesive layer 12, and a continuous carrier film 14 releasably laminated on the adhesive layer 12 of the continuous polarizing composite film 11, as shown in FIG. 2. A continuous polarizing composite film which has not been applied with the adhesive layer 12 (referred as "continuous polarizing composite film on which the adhesive layer is not yet formed 11'" or "continuous polarizing composite film 11'''" to distinguish it from a continuous polarizing composite film 11 formed with the adhesive layer 12, i.e., "continuous polarizing composite film including adhesive layer 11") or the continuous polarizing composite film including adhesive layer 11 is preliminarily subjected to an inspection for determining the presence or absence of a defect contained therein, as shown in FIG. 3. In the process of producing the roll R of the continuous inspected optical film laminate 10, there are two inspection methods as described below.

One of the inspection techniques is designed to inspect a continuous polarizing composite film on which the adhesive layer is not yet formed 11' during a process of laminating a continuous protective film on a continuous polarizer formed from a PVA film to form the continuous polarizing composite film on which the adhesive layer is not yet formed 11'. The other inspection technique is designed to perform the inspection using a roll R' of a continuous provisional optical film laminate 10' which comprises a prepared continuous polarizing composite film 11 formed with an adhesive layer, and a continuous provisional carrier film 14 releasably laminated on the adhesive layer. More specifically, The other inspection technique is designed to peel the continuous provisional carrier film 14 from the continuous provisional optical film laminate 10' being fed out from the roll R' and inspect the continuous polarizing composite film including exposed adhesive layer 11. Preferably, the continuous inspected optical film laminate 10 has a width approximately equal to a long or short side of a liquid-crystal panel to which the laminate 10 is to be attached. Preferably, the continuous protective film to be laminated on one or each of the opposite surfaces of the continuous polarizer is formed of a transparent protective film. The continuous carrier film 14 is adapted, during a liquid-crystal display element manufacturing process, to protect the adhesive layer 12 of the continuous polarizing composite film 11, and, when a normal polarizing sheet is peeled from the continuous carrier film 14 and laminated to a liquid-crystal panel, it is separated from the polarizing sheet and taken up into a roll. The continuous carrier film 14 has a function of carrying a normal polarizing sheet cut into a given length corresponding to that of a liquid-crystal panel, to the lamination station B. Therefore, it is referred to as "carrier film" herein.

For example, the continuous polarizing composite film on which the adhesive layer is not yet formed 11' or the continuous polarizing composite film including adhesive layer 11 may be formed by the following process. A PVA film having a thickness of about 50 to 80 μm is subjected to a dyeing treatment using iodine and a cross-linking treatment, and then subjected to an orientation treatment by a process of drawing in a lengthwise or widthwise direction thereof. As a result, an iodine complex is arranged in a direction parallel to the drawing direction of the PVA film, so that a continuous polarizer having an absorption axis in a direction parallel to the drawing direction is formed to absorb polarization in this direction. Preferably, the drawing direction of the PVA film is aligned with the lengthwise or widthwise direction of the PVA film to form a continuous polarizer having excellent uniformity, accuracy and optical characteristics. Typically, the absorption axis of a polarizer or a continuous polarizing composite film on which the adhesive layer is not yet formed 11' including a polarizer therein is parallel to the longitudinal direction of the continuous polarizing composite film which the adhesive layer is not yet formed 11', and a polarization axis thereof is a widthwise direction perpendicular to the longitudinal direction. The thickness of the polarizer is in the range of 20 to 30 μm. Then, a continuous protective film for protecting the formed continuous polarizing composite film is laminated on one or both of opposite surfaces of the continuous polarizer through an adhesive layer. In many cases, a transparent TAC (triacetylcellulose) film having a thickness of about 40 to 80 μm is used for the continuous polarizing composite film. In order to reduce the thickness of a liquid-crystal display element, the continuous protective film is laminated on only one of the surfaces of the continuous polarizer, in some cases. Finally, an acryl-based adhesive layer is formed on one of opposite surfaces of the continuous protective film-laminated continuous polarizer to form the adhesive layer-formed polarizing composite film 11 for the purpose of attachment to a liquid crystal panel. As shown in FIG. 2, the thickness of the adhesive layer is in the range of 10 to 30 μm. Typically, the thickness of the continuous polarizing composite film including adhesive layer 11 is in the range of about 110 to 220 μm.

Typically, a PET (polyethylene terephthalate) film is used for each of the continuous surface protection film 13 and the continuous carrier film 14. Each of the continuous surface protection film 13 and the continuous carrier film 14 is a so-called "process material", which is peeled and removed before the final stage of the liquid-crystal display element manufacturing process. The continuous surface protection film 13 is used to protect the continuous polarizing composite film 11 devoid of the adhesive layer so as not to be contaminated and damaged during the liquid-crystal display element manufacturing process, and the continuous carrier film 14 is used to protect an exposed surface of the adhesive layer. The continuous provisional carrier film 14' may be of a type similar to the carrier film 14.

One of the protective films of continuous polarizing composite film which the adhesive layer is not yet formed 11' may be replaced with a phase difference film with a optical compensatory function, using a cycloolefin-based polymer, a TAC-based polymer or the like. The continuous polarizing composite film on which the adhesive layer is not yet formed 11' may further be provided with a fixed layer by applying and orienting a polymer material such as a polyester-based or polyimide-based polymer material on a TAC-based transparent substrate. Further, in cases where the continuous polarizing composite film which the adhesive layer is not yet formed 11' is used as a polarizing composite film to be laminated to the backlight side of a liquid-crystal display element, a brightness enhancement film may laminated to a continuous protective film on the backlight side of the liquid-crystal display element to provide an additional function. Further, as for a structure of the continuous polarizing composite film on which the adhesive layer is not yet formed 11', various variations, such as laminating a TAC film to one of opposite surfaces of the continuous polarizer and laminating a PET film to the other surface of the continuous polarizer, have been proposed.

One method for forming an adhesive layer for lamination to a liquid-crystal panel, on the continuous polarizing composite film on which the adhesive layer is not yet formed 11' having the continuous protective film laminated on one or both of the surfaces is to laminate a continuous carrier film 14 having an adhesive layer provided thereon in a transferable manner, to a surface of the continuous polarizing composite film on which the adhesive layer is not yet formed 11' to be laminated to the liquid-crystal panel. A specific transfer method will be described below. In forming the continuous carrier film 14, the continuous carrier film 14 is subjected to a releasing treatment at the surface which is to be laminated on the surface of the continuous polarizing composite film on which the adhesive layer is not yet formed 11' which is to be laminated to a liquid-crystal panel, and a solvent containing an adhesive is applied to the treated surface and dried to form an adhesive layer on the carrier film 14. Then, for example, the continuous carrier film 14 having the adhesive layer 12 is continuously fed and laminated to the continuous polarizing composite film on which the adhesive layer is not yet formed 11' while synchronously feeding the continuous polarizing composite film on which the adhesive layer is not yet formed 11', to transfer the adhesive layer of the continuous carrier film 14 to the continuous polarizing composite film 11' to form an adhesive layer 12 thereon. Instead of the adhesive layer formed in the above manner, an adhesive layer 12 may be formed by directly applying a solvent containing an adhesive to the surface of the continuous polarizing composite film on which the adhesive layer is not yet formed 11' at a surface which is to be laminated to a liquid-crystal panel, and drying the solvent.

Typically, the continuous surface protection film 13 has an adhesive surface. Differently from the adhesive layer 12 of the continuous polarizing composite film 11, when a surface protection sheet (not shown) is peeled from a continuous polarizing composite film including adhesive layer 11" during the liquid-crystal display element manufacturing process, the adhesive surface must be peeled together with the surface protection sheet. FIG. 2 (product) shows a state after the surface protection sheet is peeled and removed. The surface of the surface protection film of the continuous polarizing composite film 11 may be subjected to a hard coat treatment for protecting an outermost surface of the liquid-crystal display element, and/or a surface treatment providing an anti-glare effect or the like, such as an anti-glare treatment, irrespective of whether the continuous surface protection film 13 is laminated on the continuous polarizing composite film 11.

3. Production of Information Storage/Readout device for Use in a System for Continuously Manufacturing Liquid-Crystal Display Elements With reference to FIGS. 6 to 9, description will be made on the method and system for producing an information storage/readout device for use in the liquid-crystal display element manufacturing system, according to the first and second embodiments of the present invention, wherein the information storage/readout device comprises an information storage medium 800 which stores therein the slitting position information 80 for the continuous inspected optical film laminate, and operates with a roll R of the continuous inspected optical film laminate 10 which is provided with the identification means or indicia 20 associated with the slitting position information 80.

(Method and System for Information Storage/Readout Device According to First Embodiment)

Figure 6:
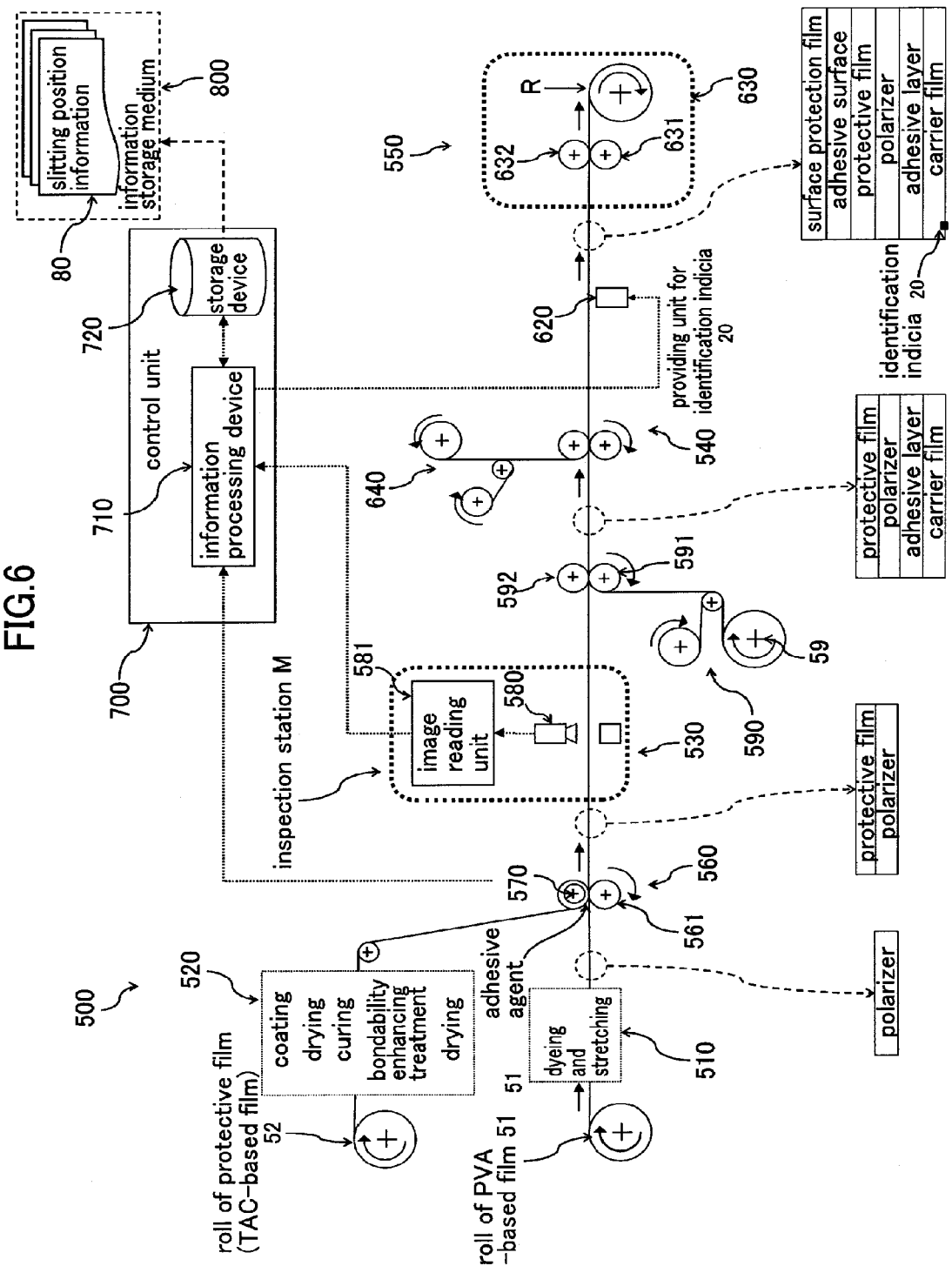
FIG. 6 is a schematic diagram showing a method and system for producing a roll R of a continuous inspected optical film laminate provided with an identification means or indicia associated with the slitting position information stored in the information storage medium, according to one embodiment of the present invention.
Figure 7:
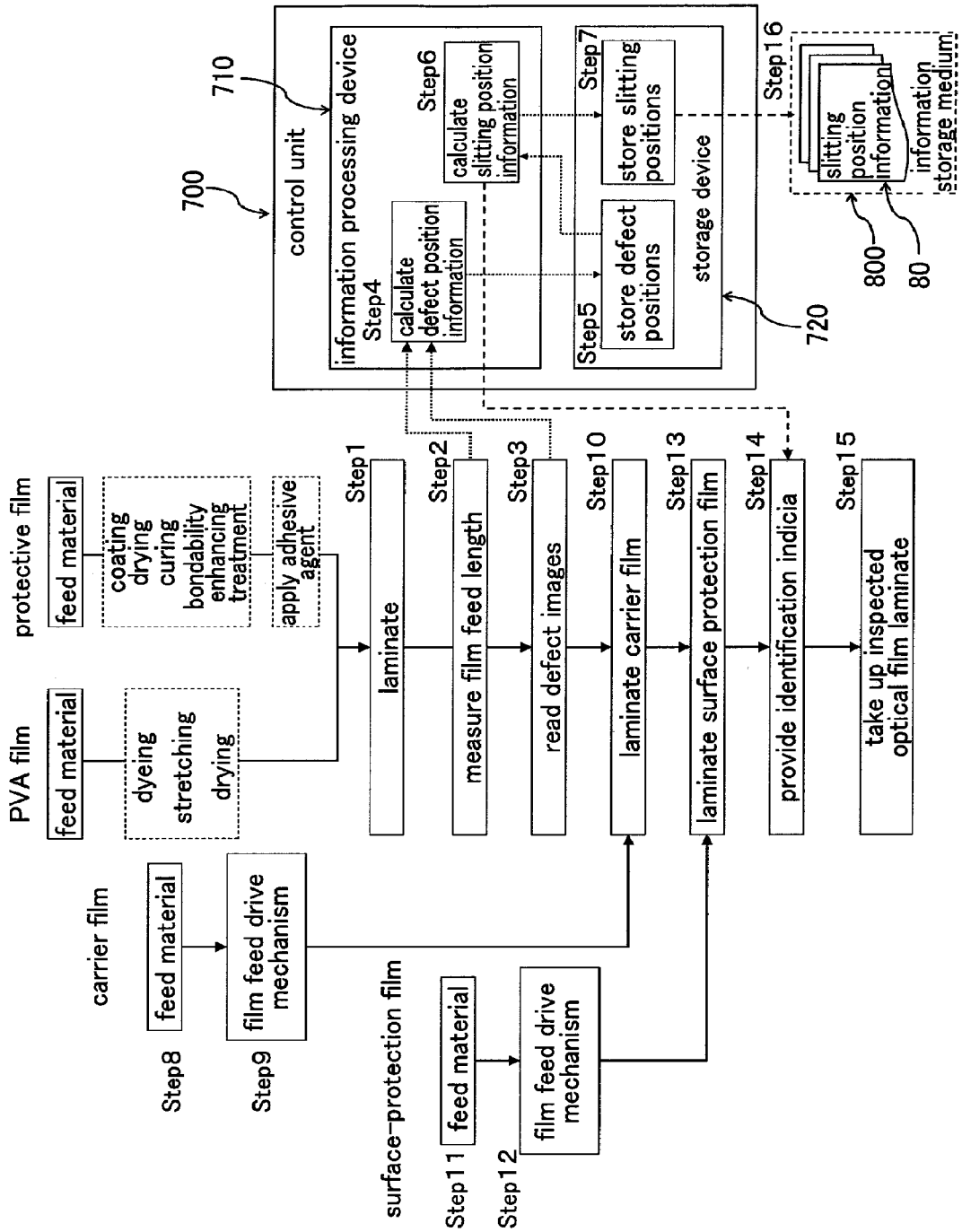
FIG. 7 is a flowchart showing a production process in the method and system for producing the roll R, illustrated in FIG. 6.

FIG. 6 is a schematic diagram showing a method and system for creating the slitting position information 80, and producing the roll R of the continuous inspected optical film laminate provided with the identification means or indicia 20 associated with the slitting position information 80 stored in the information storage medium 800. FIG. 7 is a flowchart showing the production process in the method and system for producing the roll R, illustrated in FIG. 6.

According to the first embodiment illustrated in FIG. 6, there is provided an information storage/readout device 500 which has a polarizer manufacturing line 510 for forming a continuous polarizer, a protective film manufacturing line 520 for forming a continuous protective film to be laminated on the continuous polarizer, a polarizing composite film manufacturing line 530 for laminating the continuous protective film on the continuous polarizer through an adhesive to form the continuous polarizing composite film which the adhesive layer is not yet formed 11', wherein the polarizing composite film manufacturing line includes an inspection station for performing an inspection for determining the presence or absence of a defect contained in the continuous polarizing composite film which the adhesive layer is not yet formed 11', an optical film laminate manufacturing line 540 for releasably laminating a continuous carrier film 14 formed with a transferable adhesive layer on one of the opposite surface of the continuous inspected polarizing composite film on which the adhesive layer is not yet formed 11', and optionally releasably laminating a continuous surface protection film 13 on the other surface of the continuous inspected polarizing composite film 11', to form the continuous inspected optical film laminate, and wherein the optical film laminate manufacturing line 540 includes an identification providing station for providing the identification means or indicia 20 on the continuous inspected optical film laminate, and a roll manufacturing line 550 for winding the continuous inspected optical film laminate provided with the identification means or indicia 20 to form the roll R.

As shown in FIG. 6, the polarizer manufacturing line 510 includes a station provided with a rotatably loaded roll 51 of a PVA film serving as a substrate of a continuous polarizer, and designed to subject the PVA film to dyeing, cross-linking and drawing treatment and then to drying, while feeding the PVA film from the roll 51 by a lamination drive mechanism 560 or other drive mechanism (not shown), to form a continuous polarizer. The protective film manufacturing line 520 includes a station provided with a rotatably loaded roll 52 of a film which provides a substrate of the continuous protective film, typically, a transparent TAC film, and designed to subject the transparent TAC film to a saponifying treatment and then to drying, while feeding the transparent TAC film from the roll 52 by the lamination drive mechanism 560 or other drive mechanism (not shown), to form a continuous protective film. The polarizing composite film manufacturing line 530 includes a station provided with the aforementioned lamination drive mechanism 560 having a pair of lamination rollers 561, 562, at a downstream side of the manufacturing lines 510, 520, and operates to apply an adhesive primarily consisting of a polyvinyl alcohol-based resin to an interface between the polarizer and the protective film, and drying the adhesive to bond them together through an adhesive layer having a thickness of only several μm by the lamination rollers, to form an continuous polarizing composite film on which the adhesive layer is not yet formed 11' (Step 1 in FIG. 7). The lamination drive mechanism 560 comprises a length measurement device having an encoder 570 incorporated in one of the lamination rollers to obtain distance measurement data based on a feed distance of the leading edge of the continuous polarizing composite film which the adhesive layer is not yet formed 11' just after being formed. Based on the length measurement device having the encoder 570 incorporated therein, the feed distance of the continuous polarizing composite film 11' can be measured. The lamination rollers 561, 562 are adapted to laminate the continuous polarizer and the continuous protective film to each other in a press bonding manner to form the continuous polarizing composite film 11'. The lamination rollers 561, 562 are also adapted to continuously feed the continuous polarizing composite film which the adhesive layer is not yet formed 11' in an inter-related manner with an optical film laminate take up drive mechanism 630 which will be described later.

As shown in FIG. 6 and Step 3 in FIG. 7, the polarizing composite film manufacturing line 530 further includes an inspection station M for inspecting a surface and inside of the continuous polarizing composite film which the adhesive layer is not yet formed 11' to detect any defect existing in the continuous polarizing composite film on which the adhesive layer is not yet formed 11'. The inspection station M comprises an inspection unit 580. For example, the inspection unit 580 is adapted to perform reflection inspection, transmission inspection, and/or cross-Nicol transmission inspection, as will be described later. In the inspection station M, based on the position of the detected defect in the continuous polarizing composite film which the adhesive layer is not yet formed 11', a control unit 700 associated with the inspection unit 580 operates to calculate and store a defect-free, normal region Xα and a defect-containing, defective region Xβ each delimited in a direction perpendicular to a longitudinal direction of the continuous polarizing composite film which the adhesive layer is not yet formed 11', by using an information processing device 710 and a storage device 720 (Steps 4 to 6 in FIG. 7). The control unit 700 further operates to create slitting position information which indicates normal-polarizing-sheet slitting positions defining a normal or defect-free polarizing sheet Xα corresponding to the normal region Xα, and defective-polarizing-sheet slitting positions defining a defective or defect-containing polarizing sheet Xβ corresponding to the defective region Xβ. Thus, the slitting position information 80 is provided in the continuous inspected optical film laminate which is then finally formed into the roll R (Step 7 in FIG. 7). Then, the control unit 700 operates to store the slitting position information in the storage device 720, and then store the slitting position information in the information storage medium 800. In order to backup the slitting position information 80, the slitting position information 80 may be stored in a plurality of information storage media 800. The control unit 700 may be configured to, after creating the slitting position information 80, directly transfer the slitting position information 80 to the storage device 420 of the continuous manufacturing system for liquid-crystal display element 1 via the Internet or a dedicated line, without involving the information storage medium 800. In this case, the storage device 420 functions as "information storage medium" in accordance with the present invention.

The relation between the inspection unit 580 and the control unit 700 will be described below. The inspection unit 560 comprises an image reading unit 581 such as a CCD camera. The image reading unit 581 is electrically connected to the information processing device 710 of the control unit 700. The information processing device 710 operates to process image data read by the image reading unit 581, in association with the distance measurement data obtained by the length measurement device having the encoder 570 which is electrically connected to the information processing device 710. The control unit 700 operates to cause the information processing device 710 and the storage device 720 to process the image data from the image reading unit 581 in association with the distance measurement data obtained by the length measurement device having the encoder 570 based on the feed distance of the continuous polarizing composite film on which the adhesive layer is not yet formed 11' (typically, a leading edge thereof) from an inspection position, to create position data indicative of the position of a defect contained in the continuous polarizing composite film 11', and then store the position information in the storage device 720 (Step 5 in FIG. 7). Then, the control unit 700 firstly operates to determine a normal region Xα and a defective region Xβ in the continuous polarizing composite film 11', based on the position data about the defect position (Step 6 in FIG. 7). As described in detail later, based on the normal region Xα and the defective region Xβ determined in the continuous polarizing composite film 11', the control unit 700 operates to create slitting position information 80 which indicates normal-polarizing-sheet slitting positions and defective-polarizing-sheet slitting positions each consisting of a downstream side slitting position and an adjacent and upstream side slitting position to define respective ones of a normal polarizing sheet Xα and a defective polarizing sheet Xβ, in the continuous inspected optical film laminate which is finally formed into the roll R to be used by the optical film laminate feed unit 100 in FIG. 4.

Then, the control unit 700 operates to store the slitting position information 80 in the storage device 720 (Step 7 in FIG. 7). The slitting information 80 is information indicative of positions where slits are to be formed in the continuous inspected optical film laminate along the direction perpendicular to the feed direction thereof. As described in detailed later, based on the slitting position information 80, when the continuous inspected optical film laminate is fed out from the roll R installed in the continuous manufacturing system for liquid-crystal display element (FIG. 4), in the slitting station A, a plurality of slits are formed in the continuous inspected optical film laminate along a direction perpendicular to a longitudinal direction of the continuous inspected optical film laminate from a surface opposite to the continuous carrier film to a depth reaching a surface of the continuous carrier film adjacent to the adhesive layer, to form a polarizing sheet 11" having the adhesive layer applied thereto, as shown in FIG. 2 (product). Then, the control unit 700 operates to store the slitting position information 80 in the information storage medium 800 via the storage device 720 (Step 16 in FIG. 7). In order to back up the slitting position information 80, the slitting position information 80 may be stored in a plurality of the information storage media 800. The identification means or indicia 20 created for reading out the slitting position information 80 from the information storage medium 800 or the storage device 420 is provided on the continuous inspected optical film laminate which is finally formed into the roll R (Step 14 in FIG. 7). Thus, the continuous inspected optical film laminate 10 provided with the identification means or indicia 20 is formed (Step 15 in FIG. 7). The identification means or indicia 20 may include information, such as manufacturing lot, a length (m) of the roll, or the like, associated with the slitting position information 80. Preferably, the identification means or indicia 20 is provided on the continuous inspected optical film laminate 10 at a position corresponding to a start position of the defect inspection for the continuous polarizing composite film on which the adhesive layer is not yet formed 11'.

Meanwhile, a polarizing sheet 11" formed by adjacent two slits is a normal polarizing sheet Xα having a given length determined by the length of a long or short side the liquid-crystal panel to which the sheet is to be attached, or a defective polarizing sheet Xβ having a length, typically, less than the given length xα. As shown in FIG. 4, during the liquid-crystal display element continuous manufacturing process, the control unit 400 operates to cause the identification reading unit 120 to read the identification means or indicia 20 of the continuous inspected optical film laminate 10, and to read out the slitting position information 80 from the information storage medium 800 or the storage device 420 based on the read identification means or indicia 20. Then, the control unit 400 operates to cause the slitting unit 150 to form adjacent two slits in the continuous inspected optical film laminate so as to cut a defective polarizing sheet Xβ, based on the slitting position information 80 read out from the information storage medium 800 or the storage device 420 in accordance with the results of reading of the identification means or indicia 20. Then, the control unit 400 operates to cause the defective polarizing sheet removal unit 190 in the removal station C to remove the defective polarizing sheet Xβ from the continuous carrier film 14. The control unit 400 also operates to cause the slitting unit 150 to form adjacent two slits to cut a normal polarizing sheet Xα of the given length corresponding to that of the liquid-crystal panel, and to cause the lamination unit 200 in the lamination station B to peel the normal polarizing sheet Xα from the continuous carrier film 14 and laminate the peeled normal polarizing sheet Xα to one side of the liquid-crystal panel.

Thus, the length xα of a normal polarizing sheet determined by the position data of a defect existing in the continuous polarizing composite film on which the adhesive layer is not yet formed 11' is set to a constant value determined by a length of a side of the liquid-crystal panel to which the sheet is to be attached, in any case. Differently, the length xβ of a defective polarizing sheet is determined by a downstream side slit and an upstream side slit. The upstream side slit is formed slightly upstream of the position of a defect, and the upstream side slit of an immediately preceding normal polarizing sheet may be used as the downstream side slit of the succeeding defective polarizing sheet, when viewed in the feed direction. The distance between the downstream side slit and the defect position varies when viewed in the feed direction, and thereby the length xβ of a defective polarizing sheet also varies. As described in detail later, preferably, the processing for the slitting position information 80 indicative of slitting positions is configured to allow the length xβ of the defective polarizing sheet to be set to a value different from the length xα of a normal polarizing sheet, for example, to a value satisfying the relation xβ<xα, in any case. However, if the length xα of a normal polarizing sheet is equal to the length xβ of the defective polarizing sheet, defective sheet-identification information Xγ has to be used to distinguish a normal polarizing sheet from a defective polarizing sheet. It will not be necessary to specifically mention that the defective sheet-identification information Xγ is stored in the information storage medium 800 together with the slitting position information 80 in association with the slitting position information 80. In the system 1 illustrated in FIG. 4, during the liquid-crystal display element manufacturing process, according to the slitting position information read out from the information storage medium 800 or the storage device 420, the slitting unit 150 in the slitting station A operates to form a normal polarizing sheet Xα and a defective polarizing sheet Xβ, and the defective polarizing sheet removal unit 190 in the removal station C operates to recognize and remove the defective polarizing sheet Xβ. In cases where the defective sheet-identification information Xγ is stored in the information storage medium 800 by being associated with the slitting position, the defective polarizing sheet removal unit 190 operates to recognize only the defective polarizing sheet Xβ based on the defective sheet-identification information Xγ, and remove the defective sheet Xβ. The process of creating the slitting position information is common to the first and second embodiments, and therefore will be described later, based on FIGS. 16 to 22.

After completion of the defect inspection for the continuous polarizing composite film on which the adhesive layer is not yet formed 11', it is necessary to form an adhesive layer 12 for lamination to the liquid-crystal panel, on one of the opposite surfaces of the continuous polarizing composite film on which the adhesive layer is not yet formed 11'. As shown in FIG. 6, the optical film laminate manufacturing line 540 includes a carrier film feed unit 590 provided with a roll 59 of a continuous carrier film 14 having an adhesive layer formed thereon in a transferable manner. The continuous carrier film 14 is preliminarily formed in a carrier film manufacturing line (not shown), using a PET (polyethylene terephthalate) film having a thickness of about 20 to 50 μm, as a substrate. Typically, one surface of the PET film is subjected to a releasing treatment, and then a solvent containing an acryl-based adhesive is applied to the treated surface and dried to form a transferable adhesive layer having a thickness of 10 to 30 μm, on one surface of the continuous carrier film 14. Then, a releasable film is releasably laminated on the adhesive layer. The continuous carrier film 14 is fed from the carrier film feed unit 590 while peeling off the releasable film, and releasably laminated on the continuous polarizing composite film on which the adhesive layer is not yet formed 11' by a pair of carrier film lamination rollers 591, 592. Through this operation, the adhesive layer formed on the continuous carrier film 14 is transferred to the continuous polarizing composite film 11' to form a continuous polarizing composite film including adhesive layer 11.

The optical film laminate manufacturing line 540 may include a surface protection film feed unit 640 for laminating a continuous surface protection film 13 having an adhesive surface, on the continuous polarizing composite film including adhesive layer 11 at a surface opposite to the continuous carrier film laminated thereon. The optical film laminate manufacturing line 540 further includes an identification providing unit 620 for, after forming the continuous inspected optical film laminate 10 by laminating the continuous surface protection film 13 and/or the continuous carrier film 14 on the continuous polarizing composite film including adhesive layer 11, providing the identification means or indicia 20 at a position corresponding to the position where the defect inspection is started on the continuous polarizing composite film which the adhesive layer is not yet formed 11'. The identification means or indicia 20 is created in association with the slitting position information 80 stored in the information storage medium 800. In the continuous manufacturing system for liquid-crystal display element 1 (FIG. 4) provided with the roll R of the continuous inspected optical film laminate 10 which has the identification means or indicia 20 provided thereon, the identification means or indicia 20 serves as means to allow the slitting position information 80 to be read out from the information storage medium 800 or the storage device 420, in accordance with the results of reading thereof from the continuous inspected optical film laminate 10 by the identification means reading unit 120.

The roll manufacturing line 550 includes an optical film laminate take up drive mechanism 630 having a pair of winding rollers 631, 632 adapted, after the identification means or indicia 20 is provided on the continuous inspected optical film laminate 10 by the providing unit 620, to wind the continuous inspected optical film laminate 10 to produce the roll R (Step 15 in FIG. 7). In cases where the continuous protective film is laminated on each of the surfaces of the continuous polarizer, the system 500 includes two protective film manufacturing lines 520, 520' (in this embodiment, the protective film manufacturing line 520' is omitted). Further, a treatment line may be added to the protective film manufacturing line 520 to subject a surface (non-lamination surface) of the continuous protective film to a hard coat treatment or an antidazzle or anti-glare treatment, before the continuous protective film is laminated on the continuous polarizer.

(Method and System for Producing Information Storage/Readout device according to Second Embodiment)

Figure 8:
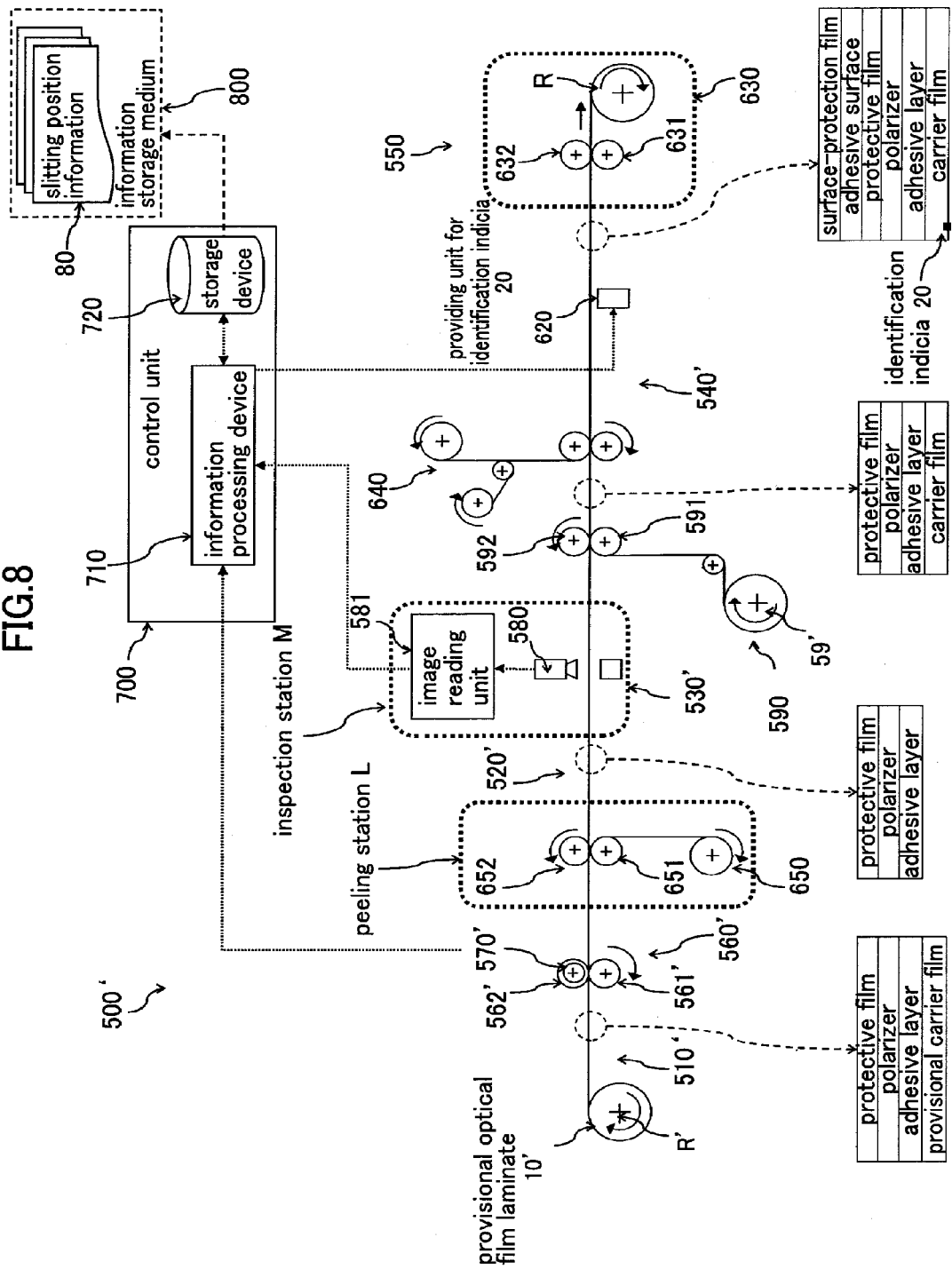
FIG. 8 is a schematic diagram showing a method and system for producing a roll R of a continuous inspected optical film laminate provided with an identification means or indicia associated with the slitting position information stored in the information storage medium, using a roll R' of a continuous provisional optical film laminate, according to another embodiment of the present invention.
Figure 9:
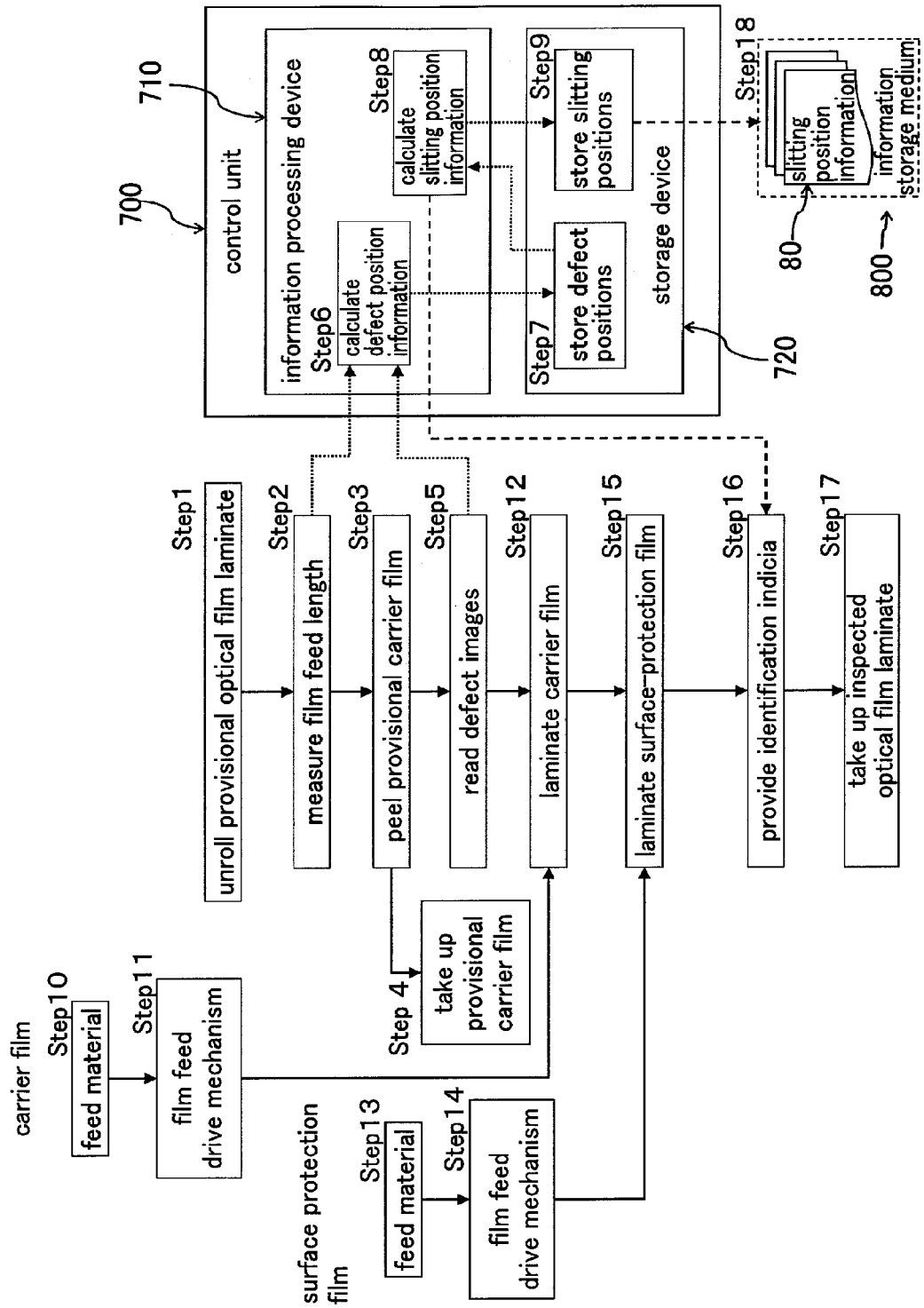
FIG. 9 is a flowchart showing a production process in the method and system for producing the roll R, illustrated in FIG. 8.

FIG. 8 is a schematic diagram showing a method and system for creating the slitting position information 80, and producing the roll R of the continuous inspected optical film laminate provided with the identification means or indicia 20 associated with the slitting position information 80 stored in the information storage medium 800, using a roll R' of a continuous provisional optical film laminate R'. FIG. 9 is a flowchart showing the production process in the method and system for producing the roll R, illustrated in FIG. 8.

An information storage/readout device 500' according to the second embodiment illustrated in FIG. 8 will be described by designating parts with identical reference characters to those in the system 500 according to the first embodiment except those different from the parts in the system 500. In the system 500' according to the second embodiment, a roll R' of a preliminarily produced and prepared continuous provisional optical film laminate 10' is used. The roll R' is formed by winding the continuous provisional optical film laminate 10' comprising a continuous polarizing composite film 11 with an adhesive layer and a continuous provisional carrier film 14' releasably laminated on the adhesive layer, into a roll. The continuous polarizing composite film 11 in the continuous provisional optical film laminate 10' consists of a continuous polarizing composite film before a defect inspection, i.e., before detecting a defect contained therein, and includes an adhesive layer and a continuous provisional carrier film 14' releasably laminated on the adhesive layer to protect the adhesive layer. Thus, the system 500' according to the second embodiment comprises a provisional optical film laminate feed line 510' for feeding the continuous provisional optical film laminate 10' from the roll R', and a polarizing composite film feed line 520' for peeling the continuous provisional carrier film 14' from the continuous provisional optical film laminate 10', and feeding the continuous polarizing composite film including adhesive layer 11 in an exposed state.

One feature of the system 500' according to the second embodiment is to subject the continuous polarizing composite film including exposed adhesive layer 11 to the defect inspection, differently from the system 500 according to the first embodiment where the continuous polarizing composite film on which the adhesive layer is not yet formed 11' itself is subjected to the defect inspection. While the two systems 500, 500' have a difference in whether or not the continuous polarizing composite film to be subjected to the defect inspection has an adhesive layer, each of the systems has a polarizing composite film manufacturing line (530, 530') for inspecting a defect contained in the continuous polarizing composite film, and an optical film laminate manufacturing line (540, 540') for releasably laminating a continuous surface protection film 13 and/or a continuous carrier film 14. In the polarizing composite film manufacturing line 530' in the second embodiment, image data of the continuous polarizing composite film including adhesive layer 11 to be laminated to a liquid-crystal panel is read by an image reading unit 581 such as a CCD camera. As in the system 500 according to the first embodiment, the image reading unit 581 is electrically connected to an information processing device 710 of a control unit 700. In the information processing device, the image data read by the image reading unit 581 is processed in association with distance measurement data obtained by a length measurement device having an incorporated encoder 570' electrically connected to the information processing device 710.

The optical film laminate manufacturing line 540' in the second embodiment includes a carrier film feed unit 590' provided with a roll 59' of a continuous carrier film 14 which has a surface subjected to a releasing treatment so that it can be releasably laminated on the exposed adhesive layer of the continuous polarizing composite film including adhesive layer 11. The continuous carrier film 14 is preliminarily formed in a carrier film manufacturing line (not shown), using a PET (polyethylene terephthalate) film having a thickness of about 20 to 50 μm, as a substrate. In the second embodiment, there is no need for a releasable film, because one surface of the PET film in the continuous carrier film 14 is subjected to a releasing treatment without forming a transferable adhesive layer as in the first embodiment. The continuous carrier film 14 is fed from the carrier film feed unit 590', and releasably laminated on the adhesive layer of the continuous polarizing composite film 11 by a pair of carrier film lamination rollers 591', 592'. The roll manufacturing line 550 of the system 500' according to the second embodiment has the same configuration and function as those of the roll manufacturing line 550 of the system 500 according to the first embodiment, and its description will be omitted.

Another feature of the system 500' according to the second embodiment is to use the roll R' of the preliminarily formed continuous provisional optical film laminate 10'. Thus, it is understood that the system 500' is devoid of the polarizing composite film manufacturing line and the protective film manufacturing line in the first embodiment. Further, there is no need for a station for applying an adhesive to the interface between the continuous polarizer and the continuous protective film, and drying the adhesive to bond them together using the pair of lamination rollers 561, 562 of the lamination drive mechanism 560 as in the polarizing composite film manufacturing line 530 in the first embodiment. Such a station corresponds to the provisional optical film laminate feed line 510' illustrated in FIG. 8 (Step 1 in FIG. 9). The provisional optical film laminate feed line 510' comprises a provisional optical film laminate feed drive mechanism 560' including a pair of feed rollers 561', 562' adapted to feed the continuous provisional optical film laminate 10' from the roll R' loaded in a support rack. The provisional optical film laminate feed drive mechanism 560' comprises a length measurement device having the encoder 570' incorporated in one of the lamination rollers and adapted to measure the feed distance of the leading edge of the continuous provisional optical film laminate 10' and create distance measurement data. Based on the length measurement device having an incorporated encoder 570', the feed distance of the continuous provisional optical film laminate 10' can be measured (Step 2 in FIG. 9). The feed rollers 561', 562' are adapted to continuously feed the continuous provisional optical film laminate 10' in inter-related manner with an optical film laminate take up drive mechanism 630 for winding a continuous inspected optical film laminate 10 to produce the roll R.

The provisional optical film laminate feed line 510' illustrated in FIG. 8 operates to feed the continuous provisional optical film laminate 10' including the continuous provisional carrier film 14', to a provisional carrier film peeling station L by the provisional optical film laminate feed drive mechanism 560'. In the provisional carrier film peeling station L of the polarizing composite film feed line 520', the continuous provisional carrier film 14' is peeled from the continuous provisional optical film laminate 10' to form an continuous polarizing composite film 11, and the continuous polarizing composite film 11 is fed with the adhesive layer in an exposed state (Steps 3 and 4 in FIG. 9). A polarizing composite film manufacturing line 530' operates to feed the continuous polarizing composite film 11 with the adhesive layer in the exposed state to an inspection station M for detecting a defect contained in the continuous polarizing composite film including exposed adhesive layer 11. In the information storage/readout device system 500 according to the second embodiment, a process of producing the continuous inspected optical film laminate 10 is substantially initiated at the polarizing composite film manufacturing line 530'.

Preferably, the roll R' of the continuous provisional optical film laminate 10' is preliminarily formed using a continuous provisional carrier film 14' formed with a transferable adhesive layer. This makes it possible to transfer the transferable adhesive layer on the continuous provisional carrier film 14' to the continuous polarizing composite film when the continuous provisional optical film laminate 10' is fed out from the roll R', and the continuous provisional carrier film 14' is peeled from the continuous provisional optical film laminate 10' in the system 500' according to the second embodiment, to form a continuous polarizing composite film including adhesive layer 11. Except that the continuous polarizing composite film 11 is subjected to the defect inspection with the adhesive layer provided thereon, the inspection station M of the polarizing composite film manufacturing line 530' is the same as the inspection station M of the polarizing composite film manufacturing line 530 in the first embodiment. The inspection station M comprises an inspection unit 580. For example, the inspection unit 580 is adapted to perform reflection inspection, transmission inspection, and/or cross-Nicol transmission inspection, as will be described later. In the inspection station M, there is provided a control unit 700 associated with the inspection unit 580 which operates, based on the position of the detected defect in the continuous polarizing composite film including adhesive layer 11, to conduct calculations to determine a defect-free, normal region Xα and a defect-containing, defective region Xβ each being defined in a direction perpendicular to the longitudinal direction of the continuous polarizing composite film including adhesive layer 11, by using the information processing device 710. There is further provided a storage device 720 for storing the results of calculations (Steps 5 to 8 in FIG. 9). The control unit 700 further operates to create slitting position information which indicates normal-polarizing-sheet slitting positions defining a normal or defect-free polarizing sheet Xα corresponding to the normal region Xα, and defective-polarizing-sheet slitting positions defining a defective or defect-containing polarizing sheet Xβ corresponding to the defective region Xβ, and finally serves as the slitting position information 80 for the continuous inspected optical film laminate finally formed into the roll R (Step 9 in FIG. 9). Then, the control unit 700 operates to store the slitting position information 80 in an information storage medium 800 via the storage device 720 (Step 18 in FIG. 9). In order to back up the slitting position information 80, the slitting position information 80 may be stored in a plurality of information storage media 800.

The relation between the inspection unit 580 and the control unit 700 is the same as that in the system 500 according to the first embodiment. The information processing device 710 operates to process image data read by the image reading unit 581, in association with distance measurement data obtained by the length measurement device having the encoder 570' electrically connected to the information processing device 710. The control unit 700 operates to cause the information processing device 710 and the storage device 720 to process the image data from the image reading unit 581 in association with the distance measurement data obtained by the length measurement device having the encoder 570' based on the feed distance of the continuous provisional optical film laminate 10' (typically, the leading edge thereof) from a position where it passes through the provisional optical film laminate feed drive mechanism 560', to create position data indicative of the position of a defect contained in the continuous polarizing composite film including adhesive layer 11' (Step 6 in FIG. 9), and then store the position information in the storage device 720 (Step 7 in FIG. 9). Then, the control unit 700 firstly operates to define a defect-free, normal region Xα and a defect-containing, defective region Xβ in the continuous polarizing composite film 11, based on the position data on the defect position (Step 8 in FIG. 9). As described in detail later, based on the normal region Xα and the defective region Xβ defined in the continuous polarizing composite film 11, the control unit 700 operates to create slitting position information 80 which indicates normal-polarizing-sheet slitting positions and defective-polarizing-sheet slitting positions each consisting of a downstream-side slitting position and an adjacent and upstream side slitting position to determine respective ones of a normal polarizing sheet Xα and a defective polarizing sheet Xβ, in the continuous inspected optical film laminate which is to be finally formed into the roll R for use with the optical film laminate feed unit 100 in FIG. 4.

Then, the control unit 700 operates to store the slitting position information 80 in the storage device 720 (Step 9 in FIG. 9). As in the first embodiment, the slitting information 80 includes information indicative of the position where a slit is to be formed in the continuous inspected optical film laminate finally formed into the roll R and being fed out from the roll R, along a direction perpendicular to the feed direction thereof. Based on the slitting position information 80, when the continuous inspected optical film laminate is fed out from the roll R installed in the continuous manufacturing system for liquid-crystal display element (FIG. 4), in the slitting station A, a plurality of slits are formed in the continuous inspected optical film laminate along a direction perpendicular to the longitudinal direction of the continuous inspected optical film laminate from a surface opposite to the continuous carrier film to a depth reaching a surface of the continuous carrier film adjacent to the adhesive layer, to form a polarizing sheet 11'' with the adhesive layer, as shown in FIG. 2 (product). Then, the control unit 700 operates to store the slitting position information 80 in the information storage medium 800 via the storage device 720 (Step 18 in FIG. 9). The identification means or indicia 20 is provided on the continuous inspected optical film laminate to allow the slitting position information 80 to be retrieved from the information storage medium 800 or the storage device 420 (Step 16 in FIG. 9). Thus, the continuous inspected optical film laminate 10 provided with the identification means or indicia 20 is formed (Step 17 in FIG. 9). Preferably, the identification means or indicia 20 is provided on the continuous inspected optical film laminate 10 at a position corresponding to the position where the defect inspection is started on the continuous polarizing composite film including adhesive layer 11. The identification means or indicia 20 may include information, such as manufacturing lot, a length (m) of the roll, or the like, associated with the slitting position information 80. Meanwhile, a polarizing sheet 11'' defined between adjacent two slits is a normal polarizing sheet Xα having a given length determined by the length of a long or short side of the liquid-crystal panel, or a defective polarizing sheet Xβ having a length, typically, less than the given length xα, as in the case of the first embodiment.

4. System for Continuously Manufacturing Liquid-Crystal Display Elements Using Information Storage/Readout Device (Feeding Continuous Inspected Optical Film Laminate Provided with Identification Means or Indicia)

Figure 10:
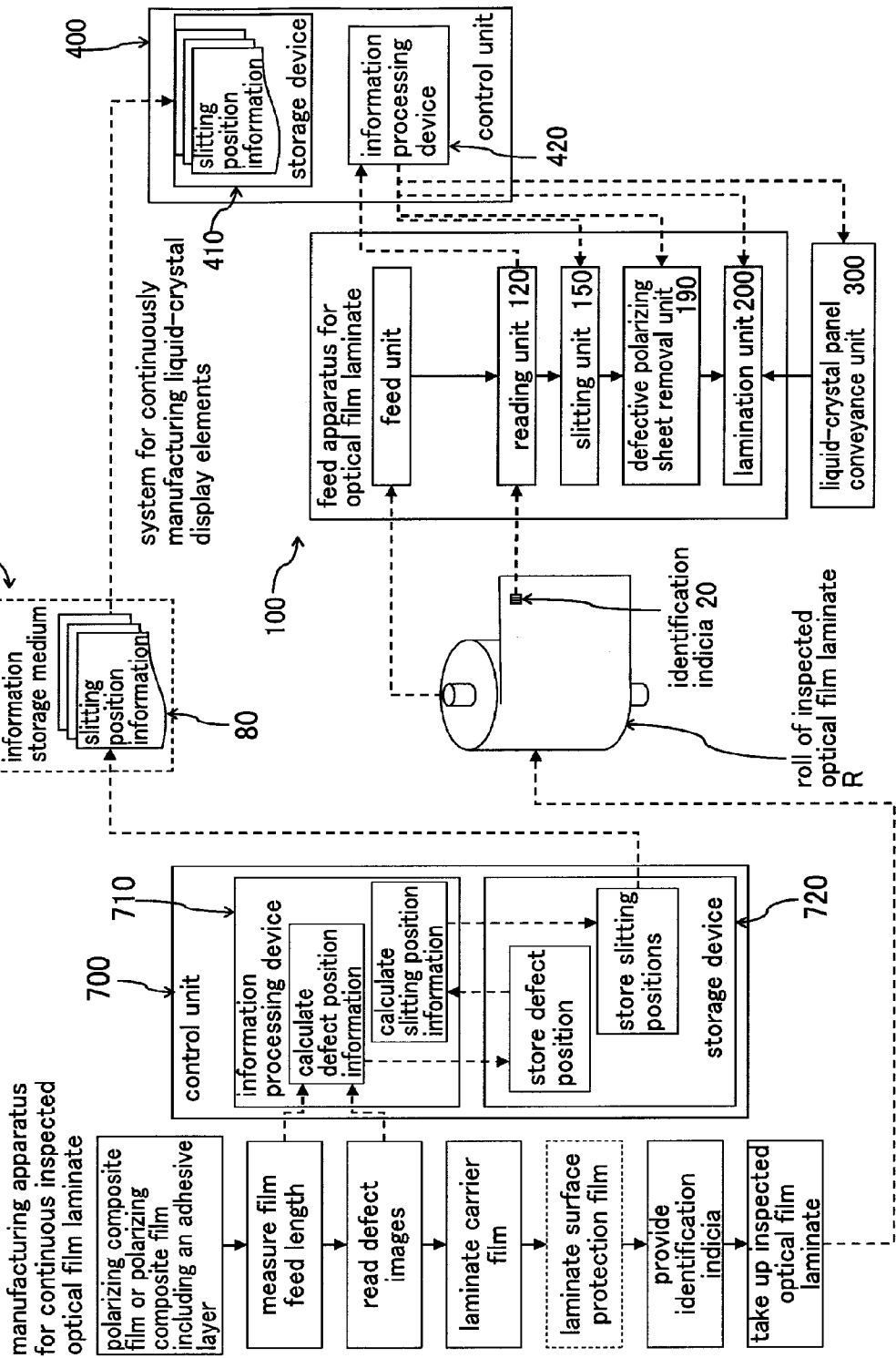
FIG. 10 is a schematic diagram showing a relationship between the identification means or indicia read from the continuous inspected optical film laminate, and the slitting position information read out from the information storage medium in accordance with reading of the identification means or indicia, in the system 1 illustrated in FIG. 4, using an information storage/readout device according to one embodiment of the present invention, which comprises the information storage medium storing therein the slitting position information created for the continuous inspected optical film laminate by the production system for the Roll R, illustrated in FIG. 6 or 8, and the roll of the continuous inspected optical film laminate provided with the identification means or indicia associated with the slitting position information.

FIG. 10 is a schematic diagram showing the relationship between the identification means or indicia 20 read by the identification reading unit 120 and the slitting position information 80 read out from the information storage medium 800 or the storage device 420 in accordance with the identification means or indicia 20, in the system for continuously manufacturing liquid-crystal display element illustrated in FIG. 4, using an information storage/readout device according to one embodiment of the present invention, which comprises the information storage medium 800 storing therein the slitting position information 80 created for the continuous inspected optical film laminate 10 by the production system for the roll R, illustrated in FIG. 6 or 8, and the roll R of the continuous inspected optical film laminate 10 provided with the identification means or indicia 20 associated with the slitting position information 80. As a third embodiment of the present invention, a method and system for continuously manufacturing liquid-crystal display elements, using the information storage/readout device, will be described with reference to the flowchart in FIG. 5.

(Recognition of Slitting Position)

In the third embodiment, the roll R of the continuous inspected optical film laminate 10 provided with the identification means or indicia 20 is rotably loaded in the support rack of the optical film laminate feed unit 100 of the continuous manufacturing system for liquid-crystal display element, and the continuous inspected optical film laminate 10 provided with the identification means or indicia 20 (hereinafter referred to simply as "continuous inspected optical film laminate 10") is continuously fed out from the roll R (Step 1 in FIG. 5). During the feeding, in Step 2 illustrated in FIG. 5, the identification means or indicia 20 provided on the continuous inspected optical film laminate 10 is read, and the slitting position information 80 is read out from the information storage medium 800 or the storage device 420 in accordance with reading of the identification means or indicia 20, and stored in the storage device 420. Further, in the information processing device 410, the read-out slitting position information is associated with distance measurement data about the feed distance of the continuous inspected optical film laminate 10 measured by the encoder 131 illustrated in FIG. 4, to determine normal-polarizing-sheet slitting positions defining a normal polarizing sheet Xα and defective-polarizing-sheet slitting positions defining a defective polarizing sheet Xβ, in Step 2 illustrated in FIG. 5. In Step 5 illustrated in FIG. 5, the slitting positions are sequentially acquired by the optical film laminate feed unit 100 illustrated in FIG. 4 for the continuous inspected optical film laminate 10.

As shown in FIG. 4, the control unit 400 operates to cause the first film feed unit 130 including the pair of feed rollers to feed the continuous inspected optical film laminate 10, based on the slitting position information and the distance measurement data about the feed distance, and then to cause the first speed adjustment unit 140 to temporarily stop the feeding of the continuous inspected optical film laminate 10 (Step 7 in FIG. 5). Then, the control unit 400 operates to cause the slitting unit 150 in the slitting station A to, based on the sequentially acquired slitting positions, form a plurality of slits in the continuous inspected optical film laminate 10 from a surface opposite to the continuous carrier film 14 to a depth reaching a surface of the continuous carrier film adjacent to the adhesive layer. Respective positions of the slits formed in the continuous inspected optical film laminate 10 are checked by the slitting position checkup unit 160 (Step 8 in FIG. 5). Then, in the removal station C, the normal polarizing sheet Xα and the defective polarizing sheet Xβ cut on the continuous carrier film 14 of the continuous inspected optical film laminate 10 are identified or discriminated in terms of a difference in length, and only the defective polarizing sheet Xβ is peeled and removed from the continuous carrier film 14, by the defective polarizing sheet removal unit 190 operated in inter-related manner with the second speed adjustment unit 180 and the second film feed unit 170 including the pair of feed rollers (Step 9 in FIG. 5). In cases where the continuous inspected optical film laminate 10 has the defective sheet-identification information Xγ associated with the slitting position information, the defective polarizing sheet removal unit 190 operates to peel and remove only the defective polarizing sheet Xβ from the continuous carrier film 14 based on the defective sheet-identification information Xγ. The continuous inspected optical film laminate 10 after removal of the defective polarizing sheet Xβ is fed to the lamination station B by the carrier film take up drive mechanism 210 in synchronization with each of a plurality of liquid-crystal panels W being sequentially conveyed to the lamination station B. The continuous carrier film 14 is taken up at a position where the leading edge of the normal polarizing sheet Xα cut into a given length corresponding to the liquid-crystal panel W reaches the leading edge of a corresponding one of the liquid-crystal panels W being sequentially conveyed (Step 11 in FIG. 5) to allow the normal polarizing sheet Xα to be peeled from the continuous carrier film 14, and an operation of laminating the normal polarizing sheet Xα to the liquid-crystal panel W by the lamination unit 200 including the pair of lamination rollers is initiated.

The operation of each of the devices, units and mechanisms under control by the control unit 400 in the liquid-crystal display panel manufacturing process will be more specifically described together with the operation of laminating the normal polarizing sheet Xα to the liquid-crystal panel W.

(Removal of Defective Polarizing Sheet Xβ)

Figure 11:
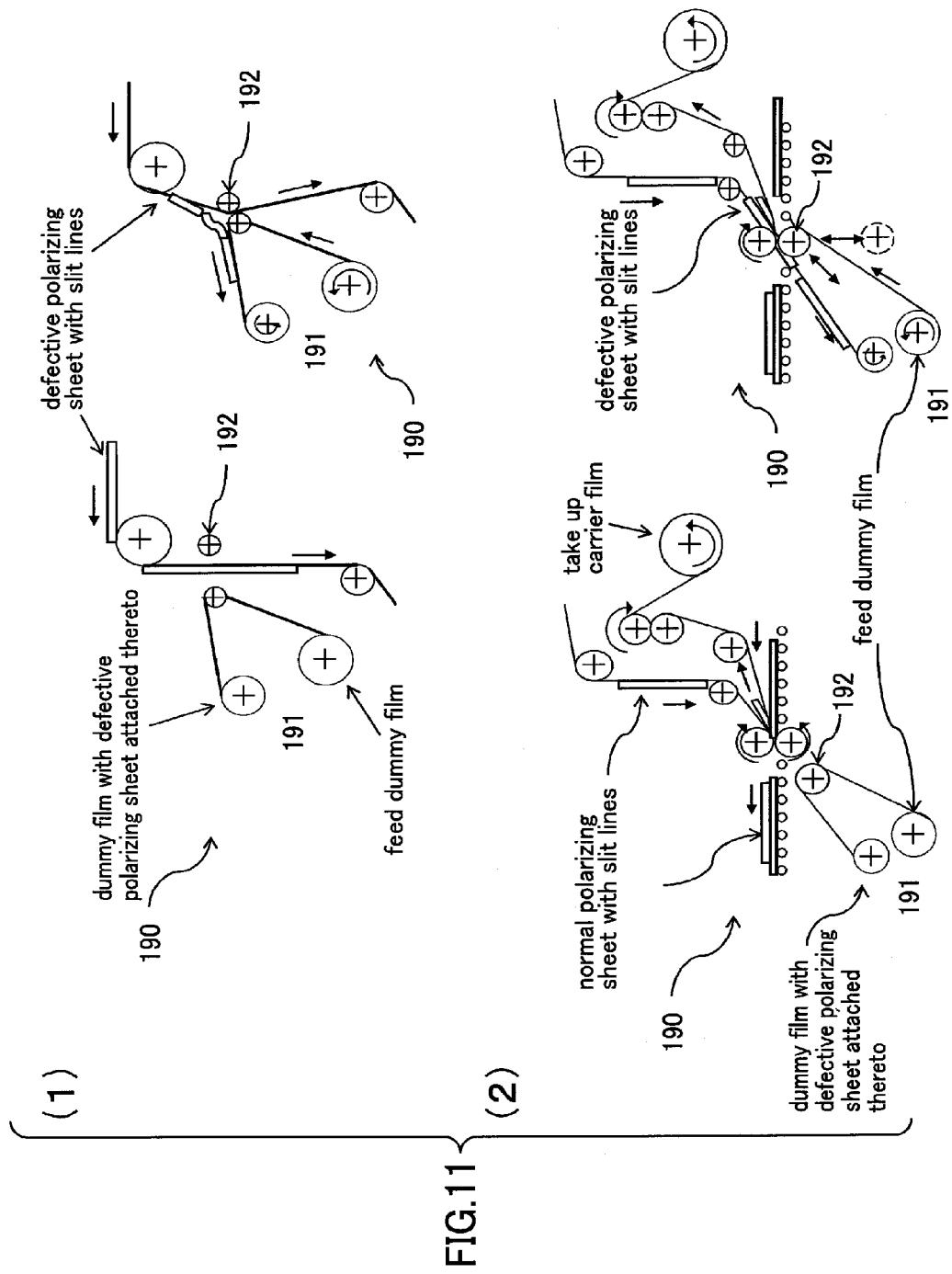
FIG. 11 is a schematic diagram showing a defective polarizing sheet removal unit of the system 1, wherein the defective polarizing sheet removal unit comprises (1) a dummy film drive mechanism disposed in a feed passage for an optical film laminate or (2) a dummy film drive mechanism adapted to be moved in and away from a gap between a pair of lamination rollers movable closer to and away from each other.

Under a condition wherein, in the continuous inspected optical film laminate 10, the normal polarizing sheet Xα and the defective polarizing sheet Xβ are cut along the slits and releasably retained on the continuous carrier film 14, the defective polarizing sheet removal unit 190 operates, under control of the control unit 400, to identify or discriminate only the defective polarizing sheet X having a length different from that of the normal polarizing sheet Xβ, or only the defective polarizing sheet Xβ associated with the defective sheet-identification information Xγ, and then peel and remove the identified defective polarizing sheet Xβ from the continuous carrier film 14. FIGS. 11(1) and 11(2) show a specific example of the defective polarizing sheet removal units 190 which is operable, under the control of the control unit 400, to identify or discriminate only the defective polarizing sheet Xβ.

A defective polarizing sheet removal unit 190 in FIG. 11(1) comprises a dummy film drive mechanism 191 having a function of allowing the defective polarizing sheet Xβ on the continuous carrier film 14 to be adhered thereto and peeled from the continuous carrier film 14, and a shifting mechanism 192 adapted, when the defective polarizing sheet Xβ reaches the start position of removal of the defective polarizing sheet Xβ in a feed path of the continuous inspected optical film laminate 10, to shift the feed path of the continuous inspected optical film laminate 10 in such a manner that it comes close to and moves away from a dummy film feed path of the dummy film drive mechanism 191.

In FIG. 11(2), there is shown a defective polarizing sheet removal unit 190 which is adapted, under control of the control unit 400, to be moved in an inter-related manner with the lamination unit 200 including the pair of lamination rollers, and comprises a dummy film drive mechanism 191 having a function of feeding a dummy film in such a manner that the defective polarizing sheet Xβ is adhered to the dummy film and peeled from the continuous carrier film 14, and a movable roller 192 defining a dummy film feed path of the dummy film drive mechanism 191. The defective polarizing sheet removal unit 190 in FIG. 11(2) is different from the defective polarizing sheet removal unit 190 in FIG. 11(1) in that the movable roller 192 defining the dummy film feed path of the dummy film drive mechanism 191 is disposed adjacent to the pair of lamination rollers of the lamination unit 200, and adapted to be moved to a position where it is paired with one of the lamination rollers. Specifically, in the lamination station B, when the defective polarizing sheet Xβ reaches an end of the feed path of the continuous inspected optical film laminate 10 (i.e., the start position of removal of the defective polarizing sheet Xβ), the control unit 400 operates to move the lamination rollers apart from each other, and move the movable roller 192 defining the dummy film feed path to a gap between the lamination rollers located in spaced-apart relation, so that the movable roller is paired with one of the other lamination rollers. At this timing, the continuous carrier film 14 is taken up by the carrier film take up drive mechanism 210, and the defective polarizing sheet Xβ is peeled from the continuous carrier film 14, so that the peeled defective polarizing sheet Xβ is adhered to the dummy film in the dummy film feed path by the movable roller 192 paired with the one lamination roller, and removed.

(Checkup of Slitting Position for the Continuous Optical Film Laminate)

In the production process of the roll R of the continuous inspected optical film laminate 10, the slitting positions (positions where slits are to be formed in the continuous inspected optical film laminate 10) are determined by the slitting position information 80 created based on the detected defect position in the continuous polarizing composite film on which the adhesive layer is not yet formed 11' or the continuous polarizing composite film including adhesive layer 11 to indicate the defective polarizing sheet-slitting position and the normal polarizing sheet-slitting position defining respective ones of the defective polarizing sheet Xβ and the defective polarizing sheet Xβ, and the distance measurement data about the feed distance of the continuous inspected optical film laminate 10. Then, during the liquid-crystal display element manufacturing process, the slitting positions are sequentially acquired by the slitting unit 150 according to an instruction of the control unit 400. Based on the slitting positions, the slitting unit 150 in the slitting station A sequentially forms a plurality of slits in the continuous inspected optical film laminate 10 along a direction perpendicular to the feed direction thereof. The slitting unit 150 operates according to an instruction of the control unit 400. If a slit formed by the slitting unit 150 based on the instruction is misaligned with the slitting positions defined by the slitting position information 80 associated with the distance measurement data of the continuous inspected optical film laminate 10, the operation of the control unit 400 for having the slitting unit 150 acquire the slitting position information 80 from the slitting unit 150 may become meaningless.

Figure 12:
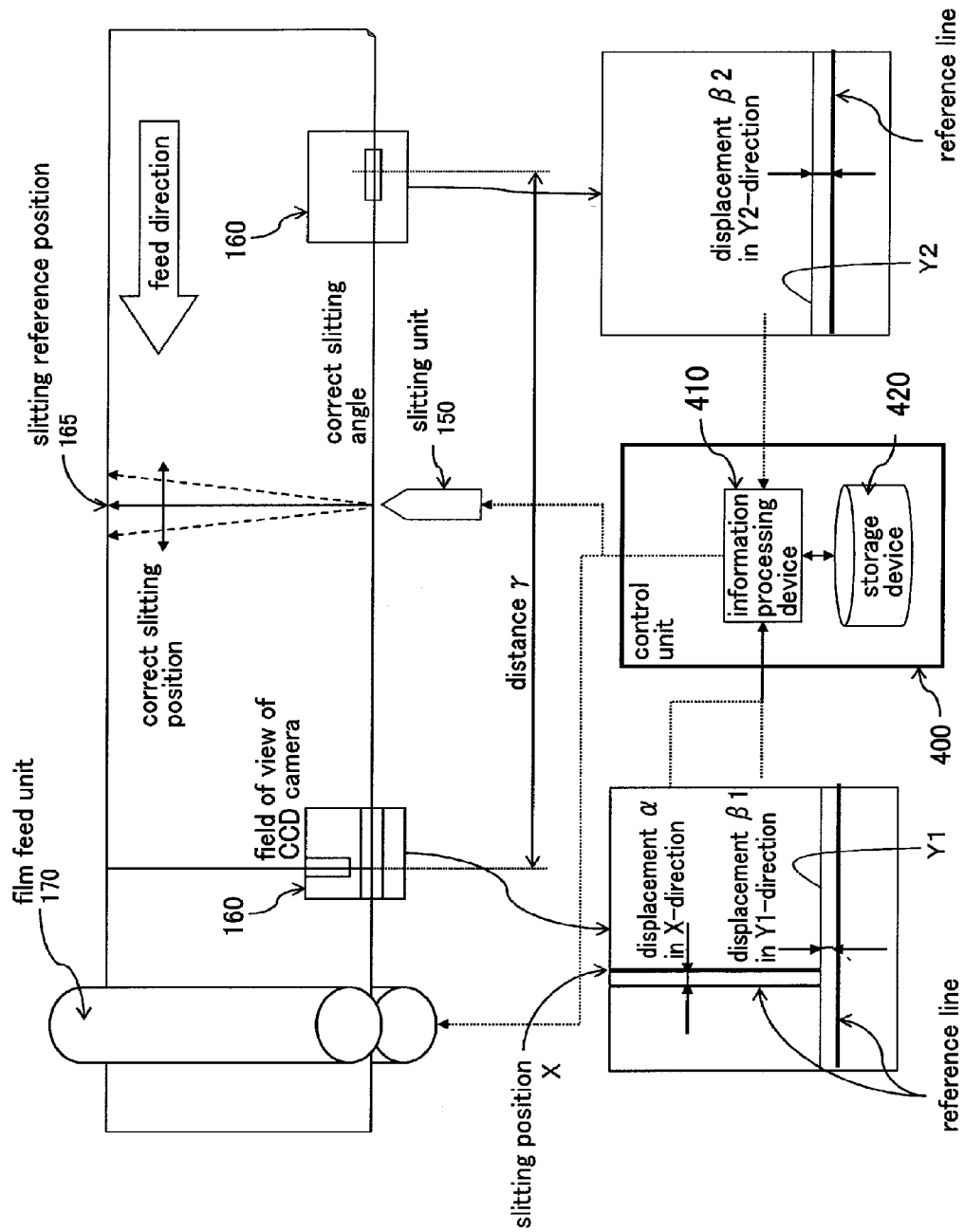
FIG. 12 is a schematic diagram showing an operation of a slitting position check-up unit of the system 1, wherein the slitting position check-up unit is adapted to check a position of a slit formed in the continuous inspected optical film laminate being fed, based on distance measurement data obtained from a feed distance of the continuous inspected optical film laminate, and the slitting position information read out in accordance with reading of the identification mean or indicia provided on the continuous inspected optical film laminate.

FIG. 12 is a schematic diagram showing the operation of a slitting position checkup unit 160 for checking a position of a slit formed in the continuous inspected optical film laminate 10 fed out from the roller R in the continuous manufacturing system, based on the distance measurement data about the feed distance of the continuous inspected optical film laminate 10, and the slitting position information read out by reading the identification means or indicia 20 provided on the continuous inspected optical film laminate 10. The slitting position checkup unit 160 is provided on each of upstream and downstream sides of the slitting unit 15 when viewed in the feed direction of the continuous inspected optical film laminate 10. There is provided a film feed unit 170 including a pair of feed rollers downstream of the downstream slitting position checkup unit 160 which functions to temporarily stop the feeding of the continuous inspected optical film laminate 10 during the period when slits are being formed therein and restart the feeding after the slits are formed. The first speed adjustment unit 140 including the dancer roll is disposed upstream of the upstream slitting position checkup unit 160 to maintain the feeding of the continuous inspected optical film laminate 10 by the first film feed unit 130 including the pair of feed rollers, even if the feeding of the continuous inspected optical film laminate 10 is temporarily stopped when slits are formed therein.

A checkup can be performed as to whether the position of a slit formed along a direction perpendicular to the feed direction of the continuous inspected optical film laminate 10 is aligned with the slitting position based on the slitting position information 80 and the distance measurement data about the feed distance of the continuous inspected optical film laminate 10 by determining accurate positions in the feed (traveling) direction (X-direction) and a crosswise direction (Y-direction) of the continuous inspected optical film laminate 10. Preferably, the checkup is performed by measuring a misalignment between respective positions of an actually formed-slit and a reference line in the X-direction, and a misalignment between respective positions of an edge (side edge) of the continuous inspected optical film laminate 10 in the Y-direction, at two positions on upstream and downstream sides of slitting positions where slits are to be formed in the continuous inspected optical film laminate 10 (position of the slitting unit 150). For example, each of the slitting position checkup units 160 may be provided with a CCD camera to pick up and process an image of an area of the actually formed-slit and the edge of the continuous inspected optical film laminate 10. The reference lines are preset in each of the image-pickup regions (camera field of view). Each of the positions of the actually formed-slit and the edge of the continuous inspected optical film laminate 10 is determined by a difference in contrast within the acquired image. Then, a distance (misalignment) between each of the positions of the actually formed-slit and the edge of the continuous inspected optical film laminate 10, and the position of a corresponding one of the preset reference lines is calculated, and a position and an inclination angle of the slitting unit 150 is corrected on the upstream or downstream side in the feed direction of the continuous inspected optical film laminate 10, based on the calculated distance (misalignment). More specifically, as shown in FIG. 5, Steps 3, 4 and 7 are performed under a condition that the continuous inspected optical film laminate 10 is fed in a tensioned state. Further, in Step 5, a slit is formed in the continuous inspected optical film laminate 10. Then, using the two slitting position checkup units 160, it is determined whether there is a misalignment between an actually formed slitting position in the continuous inspected optical film laminate 10 and a corresponding slitting position calculated by the control unit 400. If there is any misalignment, it is corrected in Steps 6 and 8, for example, in the following manner.

A misalignment between an actually formed slitting position in the continuous inspected optical film laminate 10 and a corresponding reference slitting position may be determined and corrected in the following process.

(1) Images of areas of an actually formed slit (X) and two edges (Y1, Y2) in the continuous inspected optical film laminate 10 are picked up by the CCD camera of the slitting position checkup unit 160, and the picked-up image is processed to measure respective positions of the actually formed slit (X) and the edges (Y1, Y2) based on a differences in contrast within the images.

(2) A reference slit formation position extending in the Y direction is pre-set at a position intermediate between an upstream reference line pre-set in an image pickup region of the upstream slitting position checkup unit 160 to extend in the Y-direction, and a downstream reference line pre-set in an image-pickup region of the downstream slitting position checkup unit 160 to extend in the Y direction, and data γ representing a distance between the upstream and downstream reference lines is pre-stored in the storage device 420 via the information processing device 410. Furthermore, two upstream and downstream reference lines each extending in the X direction are pre-set in respective ones of the image-pickup regions of the upstream and downstream slitting position checkup units 160.

(3) A correction value α of a slitting position and a correction value δ of a slitting angle are calculated based on the reference lines and the measured slitting position (X) and the measured edge positions (Y1, Y2) of the continuous inspected optical film laminate 10. The correction value α of the slitting position of the continuous inspected optical film laminate 10 is a measured misalignment α, i.e., a misalignment α between the actually formed slitting position (X) and the downstream reference line extending in the Y direction. The correction value δ of the slitting angle can be calculated according to the following formula, based on misalignments β1, β2) with respect to respective ones of the upstream and downstream reference lines each extending in the X direction, i.e., misalignments each measured in a respective one of the two image-pickup regions as a distance from the edge position of the continuous inspected optical film laminate 10 in the Y direction.

$$\delta = \cos^{-1}\left\{\frac{\gamma}{\sqrt{\gamma^2 + (\beta_1 - \beta_2)^2}}\right\}$$

(4) The correction values (α, δ) obtained based on the measured and calculated data to instruct the slitting unit 150 to perform an angular correction by δ and a positional correction by a in the X direction so as to be aligned with the reference slitting position extending in the Y direction are stored in the storage device 420.

(5) In advance of a next operation of forming a slit in the continuous inspected optical film laminate 10, based on the stored correction values (α, δ), the control unit 400 instructs the cutting unit 150 to perform a correction in the feed direction and an angler correction in a crosswise direction with respect to the feed direction.

(6) After the corrections, the cutting unit 150 operates to form a next slit in the continuous inspected optical film laminate 10.

(Lamination of Normal Polarizing Sheet Xα to Liquid-Crystal Panel)

A first feature of the system for continuously manufacturing liquid-crystal display element using the information storage/readout device according to the above embodiment, which comprises the roll R of the continuous inspected optical film laminate 10 provided with the identification means or indicia 20, and the information storage medium which stores therein the slitting position information 80 for the continuous inspected optical film laminate 10 to be read out therefrom in accordance with reading of the identification means or indicia 20, is in that, in advance of an operation of laminating to a liquid-crystal panel W the normal polarizing sheet Xα cut into a given length corresponding to the liquid-crystal panel W, from the continuous inspected optical film laminate 10 being fed, only the defective polarizing sheet Xβ cut from the continuous inspected optical film laminate 10 being fed can be removed by the removal unit 190, without interrupting the feeding of the continuous inspected optical film laminate 10. A second feature of the system for continuously manufacturing liquid-crystal display element using the information storage/readout device according to the above embodiment, is in that only the normal polarizing sheet Xα cut into the given length corresponding to the liquid-crystal panel W can be fed to the lamination unit 200 for lamination to the liquid-crystal panel W in the lamination station, by the carrier film take up drive mechanism 210, without interrupting the feeding of the continuous inspected optical film laminate 10, which is unimaginable in the discrete sheet or discrete sheet-based liquid-crystal display element manufacturing process. The use of the information storage/retrieval sub-system in a liquid-crystal display element production process undoubtedly makes it possible to drastically increase/enhance a speed and accuracy of lamination between the normal polarizing sheet Xα and the liquid-crystal panel W.

(Conveyance of Liquid-Crystal Panel)

Figure 1:
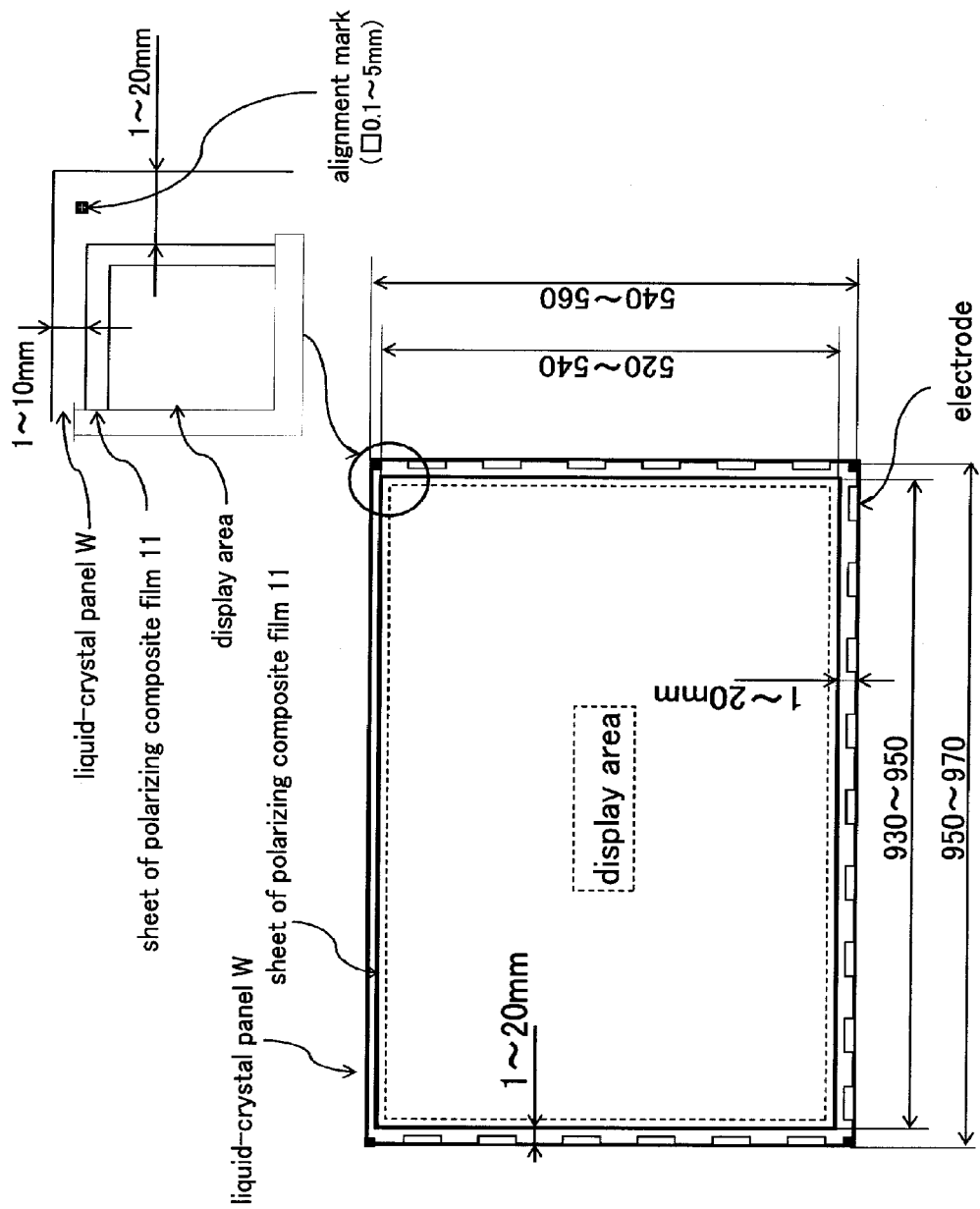
FIG. 1 illustrates a typical example of a liquid-crystal display element for a widescreen television having a diagonal screen size of 42 inches.
Figure 13:
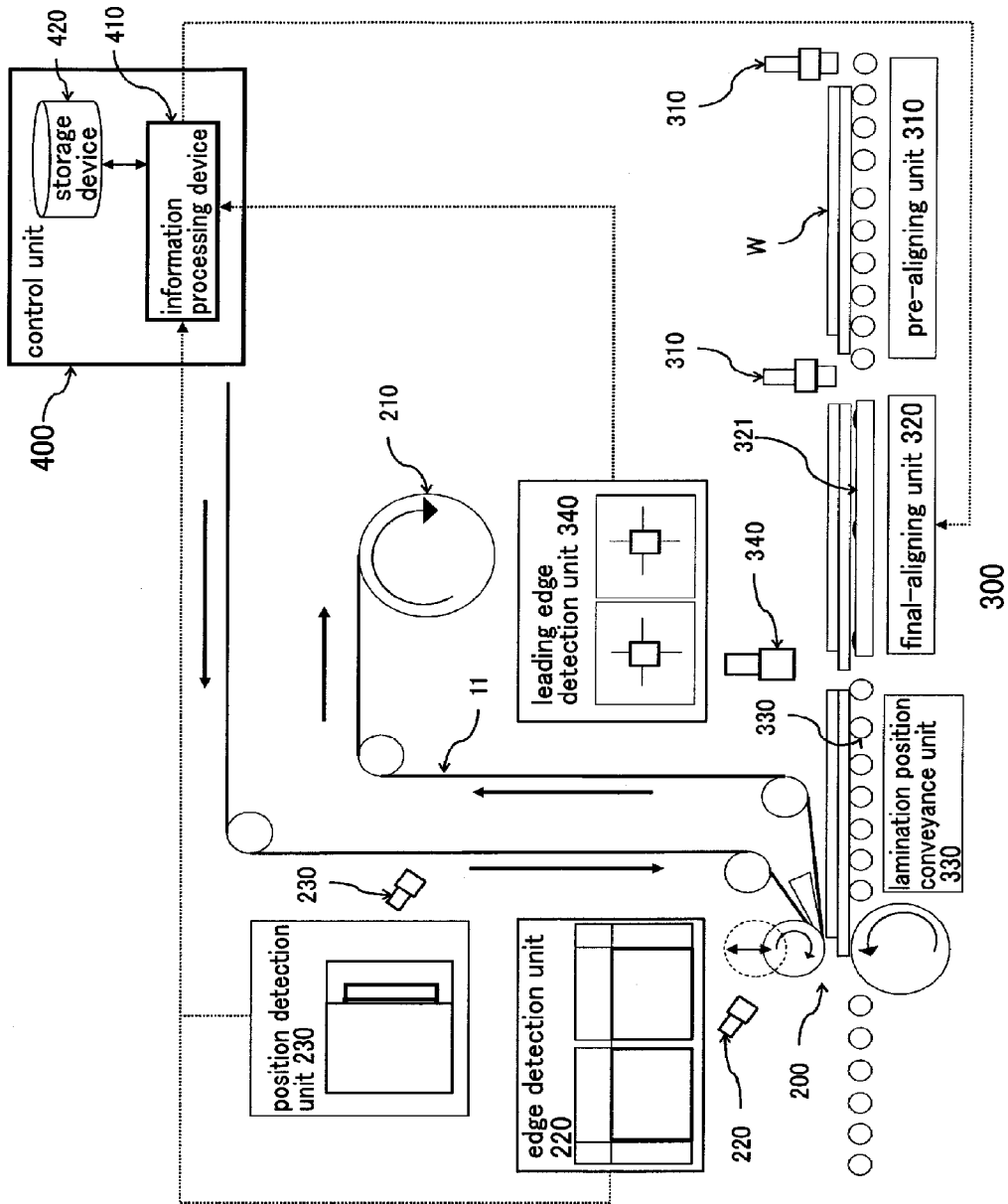
FIG. 13 is a schematic diagram showing an operation of conveying a liquid-crystal panel in a posture controlled by a pre-alignment unit, a final-alignment unit, a final conveyance unit and a panel-edge detection unit in the liquid-crystal panel conveyance unit, before laminating to the liquid-crystal panel a normal polarizing sheet cut into a given length corresponding to that of the liquid-crystal panel, in the system 1.

Before specifically describing the lamination unit 200 including the pair of lamination rollers adapted to be moved closer to and away from each other in vertical direction, so as to laminate the normal polarizing sheet Xα cut into a given length corresponding to a liquid-crystal panel W, to the liquid-crystal panel W, an outline of the liquid-crystal panel conveyance unit 300 for conveying the liquid-crystal panel W to be laminated with the normal polarizing sheet Xα cut into the given length corresponding to the liquid-crystal panel W, from the continuous inspected optical film laminate 10 being fed will be described below. For example, in a liquid-crystal display element for a widescreen television having a diagonal screen size of 42 inches, a rectangular-shaped liquid-crystal panel W has a size of 540 to 560 mm length×950 to 970 mm width, as shown in FIG. 1. In a liquid-crystal display element production process, an outer periphery of the liquid-crystal panel W is slightly cut in a wiring stage including mounting of electronic components. Alternatively, the liquid-crystal panel W may be in advance cut before it is conveyed to the lamination line. A plurality of the liquid-crystal panels W are taken out of a magazine having a large storage capacity, one-by-one, by a liquid-crystal-panel supply apparatus, and conveyed to the lamination unit 200 for lamination with respective ones of the normal polarizing sheets Xα, by the conveyance apparatus 300, while being adjusted at even intervals and a constant conveyance speed, for example, via a cleaning/polishing process. The normal polarizing sheet Xα is cut from the continuous inspected optical film laminate 10 to have a size slightly less than that of the liquid-crystal panel W. As shown in FIG. 13, in a final stage of sequential conveyance of a plurality of the liquid-crystal panels W to the lamination station B, in synchronization with feeding of the normal polarizing piece Xα, the liquid-crystal panel conveyance unit 300 has a position or panel-posture control mechanism which comprises a pre-alignment unit 310, a final-alignment unit 320, a final conveyance unit 330 for conveyance to the lamination unit, and a panel-edge detection unit 340 for detecting a reading edge of each of the liquid-crystal panels W.

FIG. 13 is a schematic diagram showing a part of the system for continuously manufacturing liquid-crystal display elements using the information storage/readout device according to the above embodiments, wherein, before the normal polarizing sheet Xα cut into the given length corresponding to the liquid-crystal panel W, from the continuous inspected optical film laminate 10, is laminated to the liquid-crystal panel W, and wherein the control unit 400 operates to control each of the pre-alignment unit 310, the final-alignment unit 320, the final conveyance unit 330 and the panel-edge detection unit 340 of the liquid-crystal panel conveyance unit 300 based on the encoded information read from the continuous web of optical film by the identification means reading unit 120, to convey the liquid-crystal panel W while adjusting the position or the posture thereof. FIG. 14 is a schematic diagram showing the lamination unit 200 for lamination of the polarizing sheets to the liquid crystal panel W, together with the edge detection unit 220 for detecting a leading edge of the normal polarizing sheet Xα cut into the given length corresponding to the liquid-crystal panel W, from the continuous inspected optical film laminate 10 illustrated in FIG. 13, and the position or straight-ahead-posture detection unit 230 for assuring that the normal polarizing sheet Xα is oriented in the feed direction.

Preferably, the normal polarizing sheet Xα is fed to the lamination unit 200 in the lamination station B at a constant speed by the continuous carrier film 14. As shown in FIG. 13 or 14, at the lamination station B, only the continuous carrier film 14 is peeled by having the carrier film bent at an acute angle, by the carrier film take up drive mechanism 210, via a peeling plate 211. By having the continuous carrier film bent at an acute angle, the adhesive layer of the normal polarizing sheet Xα can be gradually exposed. This makes it easy to align the leading edge of the liquid crystal panel W with the leading edge of the normal polarizing sheet Xα when the leading edge of the normal polarizing sheet Xα is slightly exposed. As shown in FIG. 13, the leading edge of the normal polarizing sheet Xα is fed to appear at the gap between the pair of lamination rollers of the lamination unit 200 located in spaced apart relation to each other, and detected by the edge detection unit 220. Although the normal polarizing sheet Xα is fed while being maintained on the continuous carrier film 14, the normal polarizing sheet Xα is less likely to be accurately fed with a posture where an angle θ of the feed direction with respect to a lengthwise direction of the continuous carrier film 14 becomes zero. Therefore, respective displacements of the normal polarizing sheet Xα in the feed direction and the direction perpendicular to the feed direction are measured, for example, by picking up and processing an image thereof using a CCD camera of the position or straight-ahead-posture detection unit 230. Then, the measured displacements are represented in terms of X, Y and θ, and the calculated data is stored in the storage device 420 by the control unit 400.

Then, the plurality of liquid-crystal panels are sequentially supplied from the liquid-crystal panel-supply apparatus including a magazine for liquid-crystal panels, illustrated in FIG. 4, at even intervals and a constant speed. The liquid-crystal panels supplied one-by-one are subjected to the posture control by the liquid-crystal panel conveyance unit 300 illustrated in FIG. 13. As for this posture control, refer to FIG. 10. Each of the liquid-crystal panels is positioned by the pre-alignment unit 310, in such a manner as to allow lengthwise and widthwise directions thereof to be aligned with respective ones of a conveyance direction of a conveyance path and a direction perpendicular to the conveyance direction. The positioned liquid-crystal panel is conveyed to and placed on the final-alignment unit 320. The final-alignment unit 320 includes an alignment table 321 adapted to be turned by a drive mechanism under a control of the control unit 400. The leading edge of the liquid-crystal panel placed on the alignment table is detected by the panel-edge detection unit 340. The position of the detected leading edge of the liquid-crystal panel is crosschecked with a reference lamination position stored in the storage device 420, specifically, the calculation data represented in terms of X, Y and θ to represent the posture of the normal polarizing sheet Xα to be laminated to the liquid-crystal panel. For example, the displacement between the leading edge of the liquid-crystal panel and the reference lamination position is measured using an alignment mark of the liquid-crystal panel illustrated in FIG. 1 to calculate an angular displacement θ, and the alignment table 321 having the liquid-crystal panel placed thereon is turned by the angular displacement θ. Then, the alignment table 321 is connected to the final conveyance unit 330 for conveyance to the lamination station B. The liquid-crystal panel is conveyed to the lamination station B while keeping the same posture, by the final conveyance unit 330. The leading edge of the liquid-crystal panel is aligned with the leading edge of the normal polarizing sheet Xα, and respective leading ends of the liquid-crystal panel and the normal polarizing sheet Xα are superimposed on each other. In a final stage, the normal polarizing sheet Xα and the liquid-crystal panel W in aligned relation with each other are conveyed by the pair of lamination rollers, while being nipped therebetween. In this manner, a liquid-crystal display element is completed.

Each of the normal polarizing sheets Xα is fed to the lamination unit 200 in integral relation with the continuous carrier film 14, with the continuous inspected optical film laminate 10 being fed in a tensioned manner, so that the peripheral edge of the normal polarizing sheet Xα is less likely to be bent or sagged. Thus, there is no risk of the occurrence of bowing and sagging in the normal polarizing sheet Xα. This makes it possible to facilitate an operation of adjusting a posture of the liquid-crystal panel to conform to that of the normal polarizing sheet Xα fed to the lamination station B, and manufacture liquid-crystal display elements at a higher speed with enhanced accuracy. The above method and system can hardly be applied to the discrete sheet-based liquid-crystal display element manufacturing process where, after peeling a releasable liner from each of a plurality of discrete sheets to expose an adhesive layer, and suction-feeding each of the discrete sheets to a lamination position, the discrete sheet is superimposed on a liquid-crystal panel while adjusting a position thereof with respect to a liquid-crystal panel, and laminated to the liquid-crystal panel to complete a liquid-crystal display element. As above, the system for continuously manufacturing liquid-crystal display element premised on the use of an information storage/readout device comprising an information storage medium 800 storing therein slitting position information 80 created based on a position of a defect detected by a preliminary inspection of an continuous polarizing composite film which the adhesive layer is not yet formed 11' or an continuous polarizing composite film including adhesive layer 11 to indicate defective-polarizing-sheet slitting positions defining a defective polarizing sheet, and normal-polarizing-sheet slitting positions defining a normal polarizing sheet, in the continuous inspected optical film laminate 10 comprising a continuous polarizing composite film 11 including an adhesive layer having a width conforming to a long or short side of a liquid-crystal panel formed in a given size, and a continuous carrier film 14 releasably laminated on the adhesive layer, wherein each of the defective polarizing sheet-slitting position and the normal polarizing sheet-slitting position is defined as a line extending in a widthwise direction of the continuous inspected optical film laminate 10; and roll R of the continuous inspected optical film laminate 10 which is provided with an identification means or indicia 20 associated with the slitting position information 80.

5. Creation of Slitting Position Information 80 for Continuous Inspected Optical Film Laminate 10

FIG. 15 is a table showing types and data content of the identification means or indicia 20 to be provided on the continuous inspected optical film laminate 10, in the embodiments of the present invention. The identification means or indicia 20 may be used in the form of one-dimensional or two-dimensional code, IC tag or the like, and may include data, such as a lot number, indicative of each continuous inspected optical film laminate 10 subjected to a defect inspection for an continuous polarizing composite film which the adhesive layer is not yet formed 11' or an continuous polarizing composite film including adhesive layer 11 thereof.

(Creation of Slitting Position Information 80)

Figure 16:
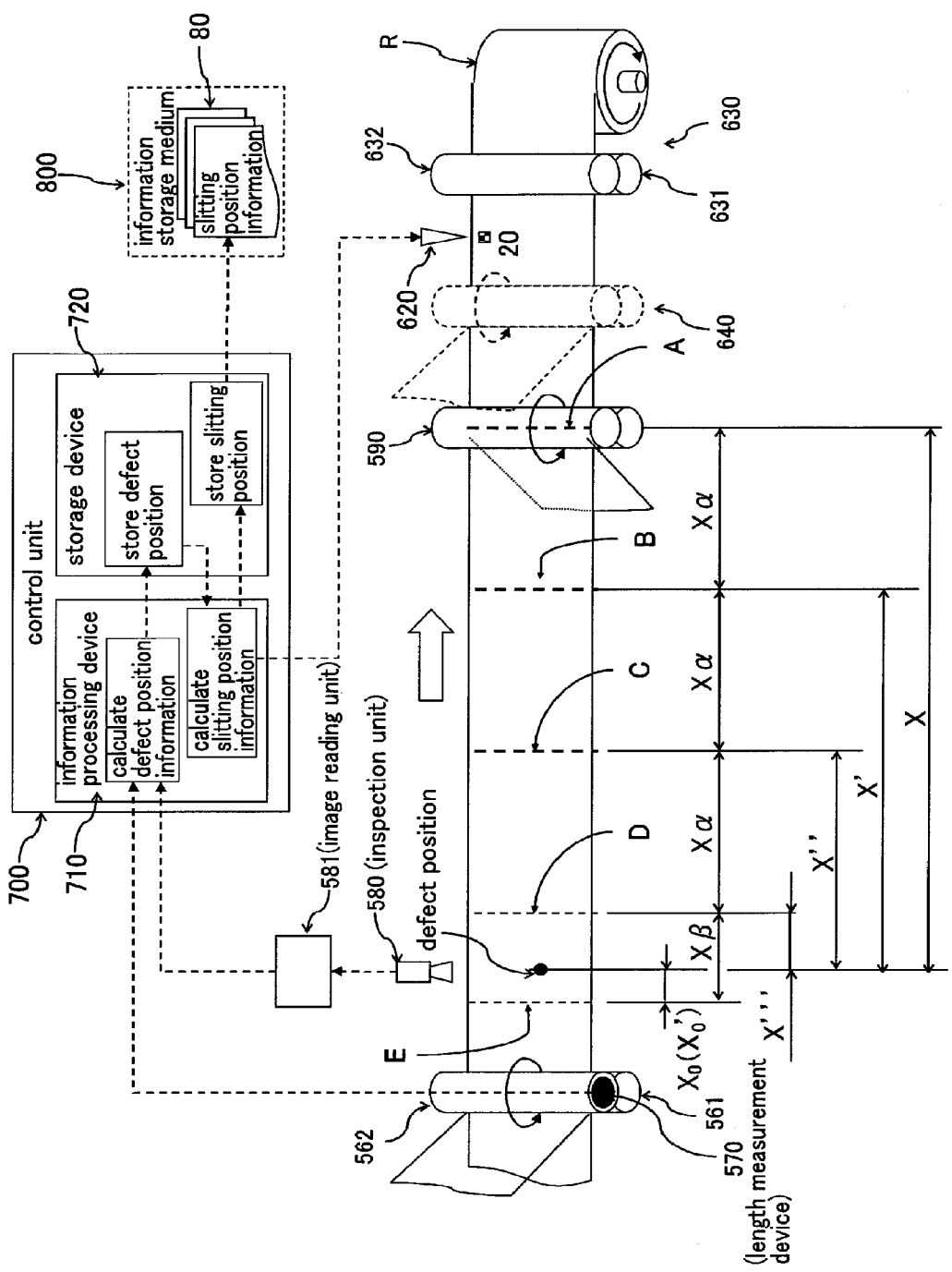
FIG. 16 is a schematic diagram showing a process of creating the slitting position information for the continuous inspected optical film laminate, by calculating a defective polarizing sheet slitting position defining a defective or defect-containing polarizing sheet and a normal polarizing sheet slitting position defining a normal or defect-free polarizing sheet, based on a position of a defect in the continuous inspected optical film laminate, in a method for producing the information storage/readout device, according to one embodiment of the present invention.
Figure 17:
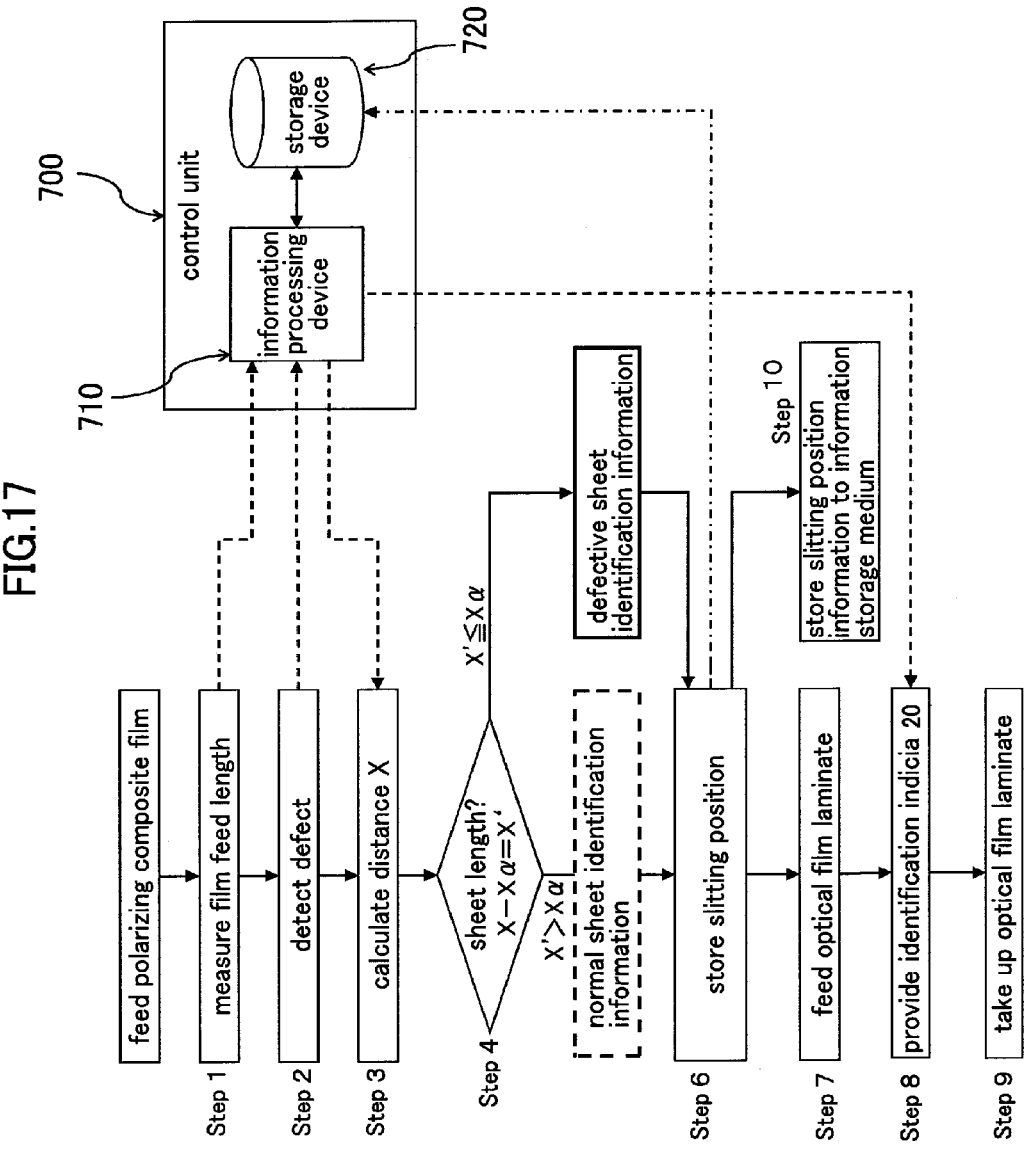
FIG. 17 is a flowchart showing a process of calculating a defective polarizing sheet slitting position defining a defective or defect-containing polarizing sheet and a normal polarizing sheet slitting position defining a normal or defect-free polarizing sheet, based on a position of a defect in the continuous inspected optical film laminate.
Figure 18:
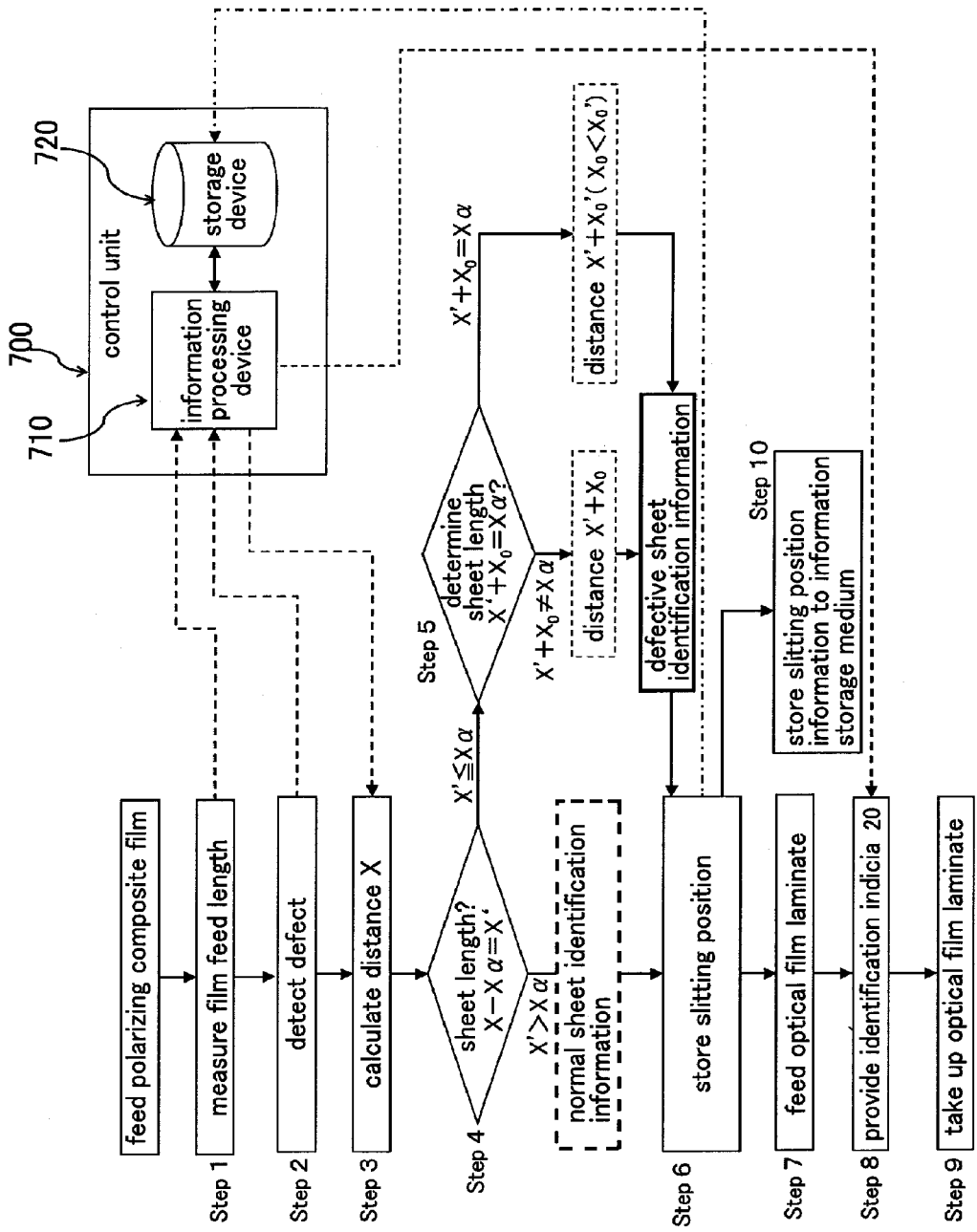
FIG. 18 is a flowchart showing another process of calculating a defective polarizing sheet slitting position defining a defective or defect-containing polarizing sheet and a normal polarizing sheet slitting position defining a normal or defect-free polarizing sheet, based on a position of a defect in the continuous inspected optical film laminate.
Figure 19:
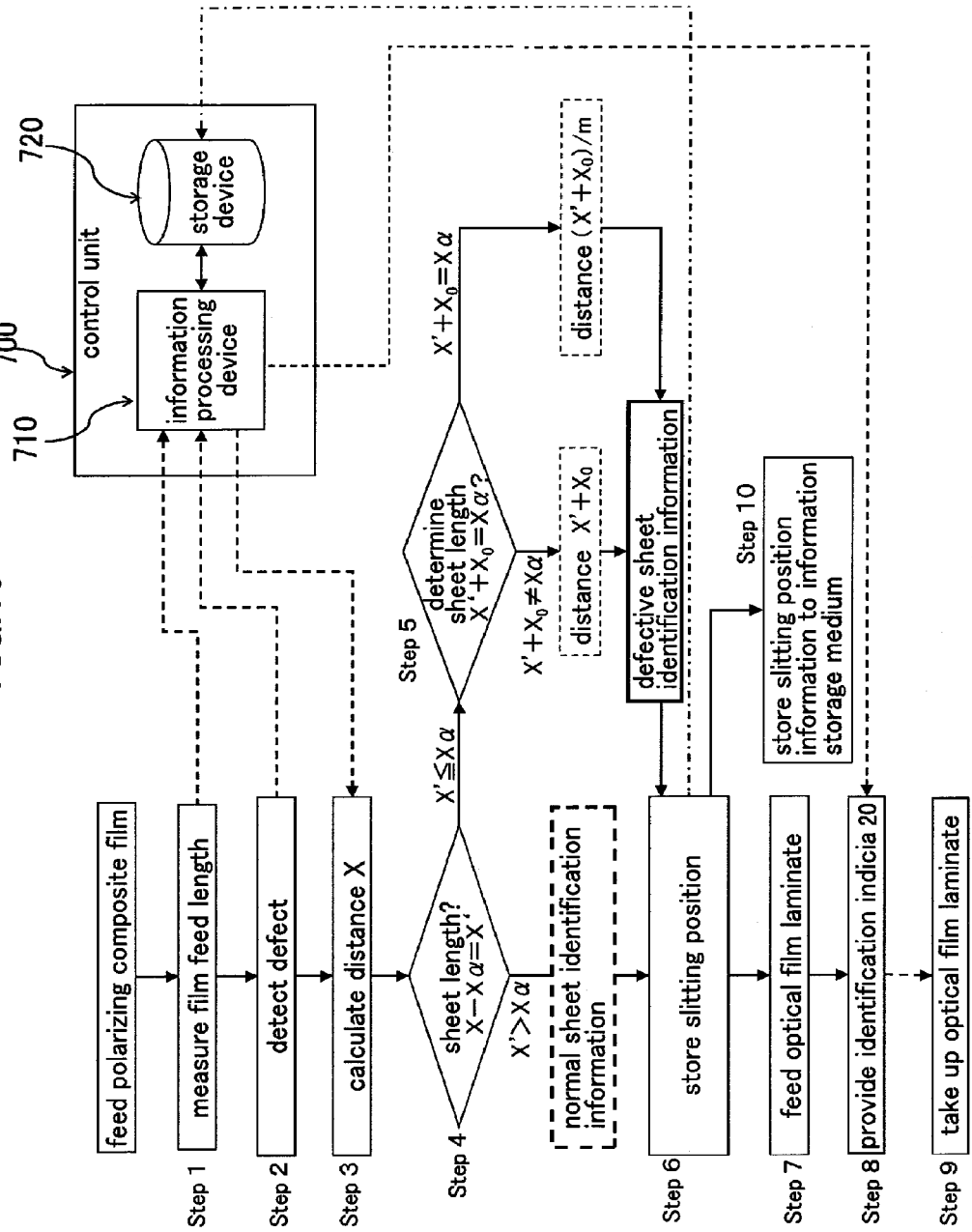
FIG. 19 is a flowchart showing yet another process of calculating a defective polarizing sheet slitting position defining a defective or defect-containing polarizing sheet and a normal polarizing sheet slitting position defining a normal or defect-free polarizing sheet, based on a position of a defect in the continuous inspected optical film laminate.

FIG. 16 is a schematic diagram showing a process of creating the slitting position information 80 for the continuous inspected optical film laminate 10, by calculating defective-polarizing-sheet slitting positions defining a defective or defect-containing polarizing sheet Xβ and normal-polarizing-sheet slitting positions defining a normal or defect-free polarizing sheet Xα, based on the position of a defect contained in the continuous polarizing composite film on which the adhesive layer is not yet formed 11' or the continuous polarizing composite film including adhesive layer 11, in a method for producing the information storage/readout device, according to one embodiment of the present invention. FIGS. 17 to 19 is a flowchart showing another process of creating the slitting position information 80 for the continuous inspected optical film laminate 10, by calculating defective-polarizing-sheet slitting positions defining a defective or defect-containing polarizing sheet and normal-polarizing-sheet slitting positions defining a normal or defect-free polarizing sheet, based on the position of a defect contained in the continuous polarizing composite film on which the adhesive layer is not yet formed 11' or the continuous polarizing composite film including adhesive layer 11. Preferably, the information storage medium 800 storing therein the slitting position information 80 may be comprised of a floppy disk, CD, DVD, a flash memory or a hard disk. While a single information storage medium may be enough, a plurality of information storage media may be used to backup the slitting position information 80 in consideration of a risk of data loss. It is to be noted that the embodiments in the schematic diagram of FIG. 16 and the flowcharts of FIGS. 17 to 19 are shown only by way of illustration.

The control unit 700 functions to operate the information processing device 710 and the storage device 720 to process image data from the image reading device 581 of the inspection unit 580 in association with the distance measurement data relating to the feed distance measured from the leading edge of the continuous polarizing composite film on which the adhesive layer is not yet formed 11' or the continuous polarizing composite film including adhesive layer 11 (the two type of continuous polarizing composite films will hereinafter be referred collectively as "continuous polarizing composite film 11") by the length measurement device having an incorporated encoder 570 or 570' incorporating the encoder, so as to create position data relating to the position of a defect contained in the continuous polarizing composite film, and then store the position data in the storage device 720. Then, the control unit 700 operates to determine a defective region Xβ and a normal region Xα in the continuous polarizing composite film 11, based on the position data relating to the detected defect position. Further, based on the defective and normal regions of the continuous polarizing composite film 11, the control unit 700 operates to create slitting position information 80 indicative of defective-polarizing-sheet slitting positions defining a defective polarizing sheet Xβ corresponding to the defective region Xβ, and normal-polarizing-sheet slitting positions defining a normal polarizing sheet Xα corresponding to the normal region Xα, in the continuous polarizing composite film 11. The slitting position information 80 is indicative of a plurality of positions at which respective ones of a plurality of slits are to be formed in the continuous inspected optical film laminate 10. In the system for continuously manufacturing liquid-crystal display elements 1, the slitting unit 150 operates to form the slits in the continuous inspected optical film laminate 10 being fed, along a direction perpendicular to the feed direction thereof from a surface opposite to the continuous carrier film 14 to a depth reaching a surface of the continuous carrier film 14 adjacent to the adhesive layer. Under the control of the control unit 700, the created slitting position information 80 is temporarily stored in the storage device 720, and then stored in the information storage medium 800. In order to backup the slitting position information 80, it may be stored in a plurality of information storage media. The slitting position information 80 is associated with the identification means or indicia 20 to be provided on the continuous inspected optical film laminate 10. In the system for continuously manufacturing liquid-crystal display elements 1 illustrated in FIG. 4, the slitting position information 80 is read out from the information storage medium 800 or the storage device 420 in accordance with the results of reading the identification means or indicia 20 by the identification means reading unit 120, and processed by the information processing device 410 of the control unit 400.

The description will now be made based on the schematic diagram of FIG. 16 and the flowcharts of FIGS. 17 to 19. The schematic diagram of FIG. 16 shows a state when the continuous inspected optical film laminate 10 is being continuously fed in a rightward direction by the feed rollers 591, 592 of the carrier film feed unit 590. The flowcharts of FIGS. 17 to 19 show specific steps from an initial step of, before the continuous carrier film 14 is releasably laminated on one of opposite surfaces of the continuous polarizing composite film 11, and, optionally, the continuous surface protection film 13 is releasably laminated on the other surface of the continuous polarizing composite film 11, under the control of the control unit 700, detecting a defect contained in the continuous polarizing composite film 11 by the inspection unit, to create the slitting position information 80 for the continuous inspected optical film laminate 10, based on the defect position, to a final step of, under the control of the control unit 700, winding the continuous inspected optical film laminate 10 provided with the identification means or indicia 20 by the optical film laminate take up drive mechanism 630 to form the roll R of the continuous inspected optical film laminate 10.

In either process, in Step 1, the control unit 700 operates to cause the lamination drive mechanism 560/the provisional optical film laminate feed drive mechanism 560' and the optical film laminate take up drive mechanism 630 to feed the continuous polarizing composite film 11. In Step 2, the control unit 700 operates to cause the inspection unit 560 including the image reading device 580 to detect the position of a defect contained in the continuous polarizing composite film, and store the detected defect position in the storage device 720 together with the type and size of the detected defect. In Steps 3 and 4, the control unit 700 operates to determine the relationship between the length of the polarizing sheet and the length (xα) corresponding to that of a normal region. The technique of determining the relationship is as follows.

In Step 3, the control unit 700 operates to cause the information processing device 710 to calculate the distance X between the reference position and the defect position in the continuous polarizing composite film 11 being fed, and store the calculated distance X in the storage device 720. For example, as shown in FIG. 16, the distance X is a distance between the position of the carrier film feed unit 590 (the reference position of the continuous polarizing composite film 11) and the position of the inspection unit 580/image-reading device 581 (the defect position).

In Step 4, the control unit 700 further operates to cause the information processing device 710 to subtract a length (xα) corresponding to that of the normal region from the distance X to obtain a distance (x−xα)=x', and then store the distance x' in the storage device 70. The length (xα) corresponding to that of the normal region of the continuous optical film is set based on the size of a liquid-crystal panel, and pre-stored in the storage device 670, by a system manager. Then, the control unit 700 operates to cause the information processing device 710 to determine whether the calculated distance x' is greater or less than the length (xα) corresponding to that of the normal region of the continuous polarizing composite film 11.

Specifically, if x' (or x") in FIG. 16>xα, it means that the normal region (Xα) of the continuous polarizing composite film 11 can be ensured. Thus, the control unit 700 operates to determine a position B spaced apart from the reference position A (first slitting position) on an upstream side by the length (xα), as a next slitting position for cutting a normal polarizing sheet Xα corresponding to the normal region, and then instructs the lamination drive mechanism 560/the provisional optical film laminate feed drive mechanism 560' and the optical film laminate take up drive mechanism 630 to feed the continuous polarizing composite film 11 in a tensioned manner by the length (xα) of the normal region. The value of the length (xα) constitutes as a part of the slitting position information for forming a normal polarizing sheet Xα corresponding to the normal region in the continuous polarizing composite film 11. After determining the second slitting position (position B), a third slitting position (position C) is determined in the same manner, and the continuous polarizing composite film 11 is fed under tension by the length (xα) of the normal region.

On the contrary, if x'≦xα, i.e., X''' in FIG. 16≦xα, it means that the normal region (Xα) of the continuous polarizing composite film 11 cannot be ensured. In this case, the region which can be taken in the continuous polarizing composite film 11 having a length (xβ) is a defective region. Thus, the control unit 700 operates to cause the information processing device 710 to add a certain distance x0 to x' (x''' in FIG. 16) so as to derive a length (x'+x0)=xβ corresponding to the defective region Xβ. Specifically, a position E spaced apart from the position D on the upstream side by the length xβ is a defective region corresponding to the defective region. The control unit 700 instructs the lamination drive mechanism 560/the provisional optical film laminate feed drive mechanism 560' and the optical film laminate take up drive mechanism 630 to feed the continuous polarizing composite film 11 under tension by the length (xβ) of the defective region. The value of the length (xβ) constitutes a part of the slitting position information for forming a defective polarizing sheet Xβ corresponding to the defective region in the continuous polarizing composite film 11.

Specifically, the control unit 700 operates to calculate the following (a) and (b) to create slitting position information 80 indicative of a plurality of positions at which respective ones of a plurality of slits are to be formed to allow normal polarizing sheets Xα and defective polarizing sheets Xβ to be formed in the continuous inspected optical film laminate 10 which is fed during the liquid-crystal display element manufacturing process:

(a) a distance (Xα) to a next slitting position, if x'>xα; and
(b) a distance (x'+x0=Xβ) to a position for forming a next cut line, if x<xα, and then operates to store the slitting position information in the storage device 720.

If a length (x'+x0=xβ) corresponding to the defective region becomes equal to the length (xα) corresponding to the normal region, i.e., if (x'+x0)=(xα), the control unit 700 cannot identify or discriminate the normal region (Xα) from the defective region (Xβ). This means that the defective region (Xβ) cannot be recognized by the length (xβ) thereof. Thus, for example, in the system for continuously manufacturing liquid-crystal display element illustrated in FIG. 4, each of the normal region (Xα) and the defective region (Xβ) cannot be discriminated from each other based on the distance measurement data as the feed distance of the continuous inspected optical film laminate 10, so that the slitting position information 80 created based on the distance measurement data (x'+x0) inevitably becomes imperfect. It is assumed that such a situation occurs when the position of a defect contained in the continuous polarizer film is infinitely close to a next slitting position in the continuous inspected optical film laminate 10, or when various defects are distributed over a length (xα) corresponding to the normal region.

Therefore, in Step 5, if (x'+x0) becomes equal to (xα), the control unit 700 functions to have the information processing device 710 perform a calculation based on at least one of the following techniques to create information for identifying or discriminating the normal region (Xα) over the defective region (Xβ).

In Step 5 illustrated in FIG. 17, even if, as a result of calculation of the information processing device 710, the distance (x'+x0) to a next slitting position becomes equal to the length (xα) corresponding to the normal region, the region between the two position is not a normal region (Xα). In order to allow such a region to be recognized as the defective region, there is provided defective-sheet identification information Xγ as illustrated in FIG. 20 in the form of, for example, a value "0" and a value "1" which may be associated, respectively, with the slitting position information indicative of a next slitting position corresponding to the normal region, and slitting position information indicative of a next slitting position corresponding to the defective region. Alternatively, in Step 5 illustrated in FIG. 18, a processing algorithm of the information processing device 710 may be configured, if, as a result of calculation of the information processing device 710, a distance (x'+x0) to a next slitting position becomes equal to the length (xα) corresponding to the normal region, to allow the distance to the next slitting position to become (x'+x0'), wherein x0'>x0, and store the distance (x'+x0') in the storage device 720. As shown in FIG. 21, this processing algorithm is configured to calculate the next slitting position as (x'+x0') different from xα to allow a region having the length (x'+x0') to be identified or discriminated against the normal region (Xα). In Step 5 illustrated in FIG. 19, a processing algorithm of the information processing device 710 is configured if, as a result of calculation of the information processing device 710, a distance (x'+x0) to a next slitting position becomes equal to the length (xα) corresponding to the normal region, to allow the distance to the next slitting position to become [(x'+x0) /m], wherein m=2 or more, preferably 2 or 3, and store the distance [(x'+x0)/m] in the storage device 720. As with the process shown in FIG. 18, the processing algorithm in FIG. 22 is configured to calculate the next slitting position as [(x'+x0)/m] different from xα to allow a region having the length [(x'+x0)/m] to be identified or discriminated against the normal region (Xα).

The above processes are summarized as follows. As a process of creating information for identifying or discriminating the defective and the normal polarizing sheets Xα, Xβ one from the other, any one of the following processes may be employed:

(1) To create defective-sheet identification information Xγ as information for identifying or discriminating a region having a length (x'+x0) calculated by the information processing device 710 and the normal region (Xα);

(2) To calculate a distance to a next slitting position by the information processing device 710, as a distance (X'+x0') (wherein x0'>x0) which is different from the length of the normal polarizing sheet (Xα); and (3) To calculate a distance to a next slitting position by the information processing device 610, as a distance [(x'+x0)/m] (wherein m=2 or more) which is different from Xα.

Particularly, in cases where the process (2) or (3) is employed, (x'+x0)=(xα) is changed to (x'+x0')≠xα or [(x'+x0)/m] xα through the processing illustrated in FIG. 18 or 19. Thus, the next slitting position can be used as information indicative of the defective polarizing sheet Xβ identifiable or discriminatable from the normal region.

Then, in either process, in Step 6, the control unit 700 functions to operate the information processing device 710 to determine a length between the reference position A and the next slitting position, based on the calculation result in Steps 4 and 5. In the process (2) or (3), the control unit 700 operates to cause the information processing device 710 to store the length to the next slitting position determined in Step 7, in the storage device 720. Differently, in the process (1), the control unit 700 operates to cause the information processing device 710 to store the length to the next slitting position in association with the defective-sheet identification information Xγ. In either process, in Step 6, the control unit 700 operates to cause the information processing device 710 to, based on the next slitting position stored in the storage device 720 in Step 7, create slitting position information 80 indicative of slitting positions with respect to the leading edge of the continuous inspected optical film laminate 10, in sequence. In either process, in Step 10, the slitting position information is stored in the information storage medium 800 via the storage device 720.

In either process, as shown in FIG. 16, in Step 7, the continuous carrier film 14 is releasably laminated on one of opposite surfaces of the continuous polarizer film 11 by the carrier film feed unit 590, and, optionally, the continuous surface protection film 13 is releasably laminated on the other surface of the continuous polarizer film 11 by the surface protection film feed unit 640, to form a continuous inspected optical film laminate 10. In either process, in Step 8, the control unit 700 operates to cause the providing device 720 to mark the identification means or indicia 20 created by the information processing device 710 in association with the slitting position information 800 in Step 6, on the continuous inspected optical film laminate 10 produced in a certain production lot, etc. Through the above process, the continuous inspected optical film laminate 10 provided with the identification means or indicia 20 is produced.

Finally, in Step 9, the control unit 700 functions to operate the lamination drive mechanism 560 and the optical film laminate take up drive mechanism 630 to wind the continuous inspected optical film laminate 10 provided with the identification means or indicia 20 to produce the roll R. Examples of the slitting position information 80 and the identification means or indicia 20 are shown in FIGS. 20 to 22.

6. Outline of Inspection Method and Device

FIG. 23 is a table showing an inspection device for inspecting a defect contained in an continuous polarizing composite film which the adhesive layer is not yet formed 11' or an continuous polarizing composite film including adhesive layer 11, a type of defect and a detection method, in one embodiment of the present invention. Typically, a defect contained in a continuous polarizing composite film which the adhesive layer is not yet formed 11' or a continuous polarizing composite film including adhesive layer 11 is inspected in the inspection station M, while continuously feeding the continuous polarizing composite film. The inspection station may include at least the following three types of inspection devices.

A first inspection unit is a defect inspection device designed to detect a surface of a continuous polarizing composite film 11' or a continuous polarizing composite film 11, by means of reflected light. As shown in FIG. 23, a detectable defect is limited to irregularities and flaw/undulation in a surface detectable by a CCD camera.

A second inspection device is a defect inspection device designed to detect a light which has transmitted through the continuous polarizing composite film 11' or a continuous polarizing composite film 11. The light from a light source is projected at a right angle to the surface of the film 11 or 11', and the light transmitted through the film is received by an optical inspection unit to detect a defect existing in the continuous polarizing composite film 11' or the continuous polarizing composite film 11, as a shade. As shown in FIG. 23, a detectable defect is internal foreign substances, internal pores, etc.

A third inspection device is a defect inspection device operable under cross-Nicol conditions. Along with the practical use of this defect inspection device, accuracy in defect inspection of continuous polarizing composite films has been drastically improved. Generally, there is a strong tendency to accept only such continuous polarizing composite films which has passed defect inspection under the cross-Nicol conditions, for large-size liquid-crystal display elements. An inspection process is as follows. Firstly, the continuous polarizing composite film on which the adhesive layer is not yet formed 11' or the continuous polarizing composite film including adhesive layer 11 which is a subject for inspection, and a corresponding polarization filter, are arranged to have absorption axes thereof set in a cross-Nicol arrangement. Then, the light is projected thereto from a light source, and transmitted light is observed. Through the observation, a defect contained in the continuous polarizing composite film 11' or the continuous polarizing composite film 11 is detected as a bright spot. More specifically, the third inspection device is a defect inspection device designed such that a polarization filter is disposed just before an optical sensor unit in such a manner as to allow an absorption axis thereof to extend at a right angle with respect to an absorption axis of the continuous polarizing composite film which the adhesive layer is not yet formed 11' or the continuous polarizing composite film including adhesive layer 11, and light is emitted from a light source to the optical sensor unit while passing through the continuous polarizing composite film 11' or the continuous polarizing composite film 11 at an incidence angle perpendicular or oblique thereto, to detect any defect existing in the continuous polarizing composite film on which the adhesive layer is not yet formed 11' or the continuous polarizing composite film including adhesive layer 11, as a bright spot. As shown in FIG. 23, the inspection method can detect substantially all defects, except surface irregularities.

Although the present invention has been described in connection with preferred embodiments thereof, it will be appreciated that various changes and modifications will be made by those skilled in the art without departing from the spirit and scope of the invention, defined in the appended claims, and legal equivalents of the appended claims may be substituted for elements thereof. Accordingly, the present invention is not limited to the specific embodiments disclosed as the best mode for carrying out the invention, but intended to cover all embodiments included within the scope thereof.

What is claimed is:

1. A system for producing an information storage/readout device for use in a system for continuously manufacturing liquid-crystal display elements, the system for continuously manufacturing liquid-crystal display elements being configured to work with a roll of a continuous optical film laminate which comprises a continuous polarizing composite film including an adhesive layer and having a width conforming to a long or short side of a liquid-crystal panel formed in a given size, and a continuous carrier film releasably laminated on the adhesive layer, the system for continuously manufacturing liquid-crystal display elements being configured to form a plurality of slits in the continuous optical film laminate fed out from the roll, along a direction perpendicular to a longitudinal direction thereof, to make it possible to sequentially cut a plurality of polarizing sheets each having a given length corresponding to the long or short side of the liquid-crystal panel from the continuous optical film laminate and to laminate the sheets to respective ones of a plurality of the liquid-crystal panels so as to continuously manufacture liquid-crystal display elements, the information storage/readout device comprising an information storage medium which stores therein slitting position information created based on the position of a defect detected by an inspection of a continuous polarizing composite film included in a continuous optical film laminate to indicate defective-polarizing-sheet slitting positions defining a defective or defect-containing polarizing sheet, and normal-polarizing-sheet slitting positions defining a normal or defect-free polarizing sheet, in the continuous inspected optical film laminate, and a roll of the continuous inspected optical film laminate which is provided with an identification indicia, wherein the continuous optical film laminate includes the defect-containing polarizing sheet and the defect-free polarizing sheet, the system for producing an information storage/readout device comprising:

a polarizing composite film forming unit configured to laminate a continuous protective film on at least one of opposite surfaces of a continuous polarizer to form an continuous polarizing composite film on which the adhesive layer is not yet formed;

an inspection unit configured to inspect the continuous polarizing composite film which the adhesive layer is not yet formed to detect a defect contained in the continuous polarizing composite film on which the adhesive layer is not yet formed;

slitting position information creating means configured to, based on the position of the defect in the continuous polarizing composite film on which the adhesive layer is not yet formed, create the slitting position information indicative of the normal polarizing sheet-slitting positions and the defective polarizing sheet-slitting positions defining respective ones of the normal polarizing sheet and the defective polarizing sheet in a direction perpendicular to a longitudinal direction of the continuous polarizing composite film on which the adhesive layer is not yet formed;

a continuous inspected optical film laminate forming unit configured to releasably laminate a continuous carrier film to the continuous inspected polarizing composite film on which the adhesive layer is not yet formed through an adhesive layer to form the continuous inspected optical film laminate;

an information storage medium forming unit configured to store the slitting position information in a storage medium to thereby form the information storage medium, in a manner usable by the system for continuously manufacturing liquid-crystal display elements to, during feeding of the continuous inspected optical film laminate, form a plurality of slits in the continuous inspected optical film laminate along a direction perpendicular to the longitudinal direction from a surface opposite to the continuous carrier film to a depth reaching a surface of the continuous carrier film adjacent to the adhesive layer so as to make it possible to cut the normal polarizing sheet and the defective polarizing sheet from the continuous inspected optical film laminate individually;

an identification providing unit configured to create the identification indicia in association with the slitting position information and provide the identification indicia on the continuous inspected optical film laminate;

a taking up unit configured to wind the continuous inspected optical film laminate provided with the identification indicia, into a roll to provide the roll of the continuous optical film laminate, wherein the continuous optical film laminate includes the defect-containing polarizing sheet and the defect-free polarizing sheet, and the taking up unit is configured to wind the continuous inspected optical film laminate without separating the defect-containing polarizing sheet from the defect-free polarizing sheet; and a control unit configured to control respective operations of at least the polarizing composite film forming unit, the inspection unit, the slitting position information creating means, the continuous inspected optical film laminate forming unit, the information storage medium forming unit, the identification providing unit and the taking up unit, in an inter-related manner.

2. The system for producing an information storage/readout device as defined in claim 1, wherein the continuous inspected optical film laminate forming unit includes a surface protection film feed device configured to releasably laminate a continuous surface protection film on the continuous inspected polarizing composite film at a surface opposite to the adhesive layer.

3. The system as defined in claim 1, wherein the inspection unit includes one or a combination of one or more of a first inspection device configured to primarily inspect a surface of the continuous polarizing composite film on which the adhesive layer is not yet formed by means of reflected light, a second inspection device configured to inspect a light projected from a light source and transmitted through the continuous polarizing composite film on which the adhesive layer is not yet formed to detect any defect existing in the continuous polarizing composite film on which the adhesive layer is not yet formed as a shade, and a third inspection device configured to arrange the continuous polarizing composite film on which the adhesive layer is not yet formed and a polarization filter to have absorption axes thereof set in a cross-Nicol arrangement, emitting light from a light source thereto, and observing light transmitted therethrough to detect any defect contained in the continuous polarizing composite film on which the adhesive layer is not yet formed as a bright spot.

4. A system for producing an information storage/readout device for use in a system for continuously manufacturing liquid-crystal display elements, the system for continuously manufacturing liquid-crystal display elements being configured to work with a roll of a continuous optical film laminate which comprises a continuous polarizing composite film including an adhesive layer and having a width conforming to a long or short side of a liquid-crystal panel formed in a given size, and a continuous carrier film releasably laminated on the adhesive layer, the system for continuously manufacturing liquid-crystal display elements being configured to form a plurality of slits in the continuous optical film laminate fed out from the roll, along a direction perpendicular to a longitudinal direction thereof, to make it possible to sequentially cut a plurality of polarizing sheets each having a given length corresponding to the long or short side of the liquid-crystal panel from the continuous optical film laminate and to laminate the sheets to respective ones of a plurality of the liquid-crystal panels so as to continuously manufacture liquid-crystal display elements, the information storage/readout device comprising an information storage medium which stores therein slitting position information created based on a position of a defect detected by an inspection of a continuous polarizing composite film included in a continuous optical film laminate to indicate defective-polarizing-sheet slitting positions defining a defective or defect-containing polarizing sheet, and normal-polarizing-sheet slitting positions defining a normal or defect-free polarizing sheet, in the continuous inspected optical film laminate, and a roll of the continuous inspected optical film laminate which is provided with an identification indicia, wherein the continuous optical film laminate includes the defect-containing polarizing sheet and the defect-free polarizing sheet, the system for producing an information storage/readout device comprising:

a provisional optical film laminate feed unit configured to work with a roll of a continuous provisional optical film laminate which comprises a continuous polarizing composite film formed with an adhesive layer, and a continuous provisional carrier film releasably laminated on the adhesive layer, and configured to feed the continuous provisional optical film laminate out from the roll;

a provisional carrier film peeling unit configured to peel the continuous provisional carrier film from the continuous provisional optical film laminate being fed out from the roll, to have the adhesive layer on the continuous polarizing composite film exposed;

an inspection unit configured to inspect a surface and inside of the continuous polarizing composite film having the exposed adhesive layer to detect any defect contained in the continuous polarizing composite film including adhesive layer;

slitting position information creating means configured to, based on the position of the defect in the continuous polarizing composite film having the adhesive layer, create the slitting position information indicative of the normal polarizing sheet-slitting positions and the defective polarizing sheet-slitting positions defining respective ones of the normal polarizing sheet and the defective polarizing sheet in a direction perpendicular to a longitudinal direction of the continuous polarizing composite film having the adhesive layer;

a continuous inspected optical film laminate forming unit configured to releasably laminate a continuous carrier film on the exposed adhesive layer of the continuous inspected polarizing composite film to form the continuous inspected optical film laminate;

an information storage medium forming unit configured to store the slitting position information in a storage medium to form the information storage medium, in a manner usable by the system for continuously manufacturing liquid-crystal display elements to, during feeding of the continuous inspected optical film laminate, form a plurality of slits in the continuous inspected optical film laminate along a direction perpendicular to the longitudinal direction from a surface opposite to the continuous carrier film to a depth reaching a surface of the continuous carrier film adjacent to the adhesive layer so as to make it possible to cut the normal polarizing sheet and the defective polarizing sheet from the continuous inspected optical film laminate individually;

an identification providing unit configured to create the identification indicia in association with the slitting position information and provide the identification indicia on the continuous inspected optical film laminate;

a taking up unit configured to wind the continuous inspected optical film laminate provided with the identification indicia, into a roll to provide the roll of the continuous optical film laminate, wherein the continuous optical film laminate includes the defect-containing polarizing sheet and the defect-free polarizing sheet, wherein the taking up unit is configured to wind the continuous inspected optical film laminate without separating the defect-containing polarizing sheet from the defect-free polarizing sheet; and a control unit configured to control respective operations of at least the provisional optical film laminate feed unit, the provisional carrier film peeling unit, the inspection apparatus, the slitting position information creating means, the continuous inspected optical film laminate forming unit, the information storage medium forming unit, the identification providing unit and the taking up unit, in an inter-related manner.

5. The system for producing an information storage/readout device as defined in claim 4, wherein the continuous provisional carrier film has a transferable adhesive layer formed by subjecting one surface of the provisional carrier film to a releasing treatment, applying a solvent containing an adhesive to the treated surface, and drying the solvent.

6. The system for producing an information storage/readout device as defined in claim 4, wherein the continuous carrier film is subjected to a releasing treatment at a surface which is to be laminated on the exposed adhesive layer of the continuous inspected polarizing composite film.

7. The system for producing an information storage/readout device as defined in claim 4, wherein the inspected optical film laminate forming unit includes a surface protection film feed device configured to releasably laminate a continuous surface protection film on the continuous inspected polarizing composite film at a surface opposite to the adhesive layer.

8. The system for producing an information storage/readout device as defined in claim 4, wherein the inspection unit includes one or a combination of one or more of a first inspection device configured to primarily inspect a surface of the continuous polarizing composite film including adhesive layer by means of reflected light, a second inspection device configured to inspect light which has been projected from a light source and transmitted through the continuous polarizing composite film including adhesive layer to detect any defect existing in the continuous polarizing composite film including adhesive layer as a shade, and a third inspection device configured to arrange the continuous polarizing composite film including adhesive layer and a polarization filter to have absorption axes thereof set in a cross-Nicol arrangement, emitting light from a light source thereto, and observing light transmitted therethrough to detect any defect existing in the continuous polarizing composite film including adhesive layer as a bright spot.

* * * * *